United States Patent
Peterson et al.

(10) Patent No.: US 12,011,349 B2
(45) Date of Patent: Jun. 18, 2024

(54) BALLOON EXPANDABLE STENT WITH LENGTHENED COMMISSURE POSTS FOR TRANSCATHETER IMPLANTATION OF A CARDIAC VALVE PROSTHESIS

(71) Applicant: MEDTRONIC, INC., Minneapolis, MN (US)

(72) Inventors: Justin Peterson, Santa Rosa, CA (US); Stuart Kari, Windsor, CA (US); Shahnaz Javani, Santa Rosa, CA (US); Genevieve Farrar, Novato, CA (US); Syed Askari, San Jose, CA (US); Alkindi Kibria, Anaheim, CA (US); Karl Olney, Irvine, CA (US); Kshitija Garde, Fullerton, CA (US); Justin Goshgarian, Santa Rosa, CA (US); Tracey Tien, Tustin, CA (US); Ethan Korngold, Portland, OR (US); Mark Casley, Santa Rosa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 252 days.

(21) Appl. No.: 17/186,485

(22) Filed: Feb. 26, 2021

(65) Prior Publication Data
US 2021/0275298 A1 Sep. 9, 2021

Related U.S. Application Data

(60) Provisional application No. 62/985,131, filed on Mar. 4, 2020.

(51) Int. Cl.
*A61F 2/24* (2006.01)
*A61F 2/95* (2013.01)

(52) U.S. Cl.
CPC .......... *A61F 2/2418* (2013.01); *A61F 2/9522* (2020.05); *A61F 2/2433* (2013.01); *A61F 2250/001* (2013.01)

(58) Field of Classification Search
CPC .. A61F 2/24; A61F 2/2418; A61F 2250/0039; A61F 2/2409; A61F 2/07;
(Continued)

(56) References Cited

U.S. PATENT DOCUMENTS

| 5,330,500 A | 7/1994 | Song |
| 5,411,552 A | 5/1995 | Andersen et al. |

(Continued)

FOREIGN PATENT DOCUMENTS

| EP | 2621408 B1 | 4/2016 |
| EP | 3494928 B1 | 6/2019 |

(Continued)

OTHER PUBLICATIONS

International Search Report and Written Opinion dated Jun. 23, 2021 in Intl Appl No. PCT/US2021/020684.

*Primary Examiner* — Seema Mathew
(74) *Attorney, Agent, or Firm* — MEDLER FERRO WOODHOUSE & MILLS PLLC

(57) ABSTRACT

A transcatheter valve prosthesis includes a stent and a prosthetic valve. The stent includes an inflow portion, an outflow portion, and a transition portion extending between the inflow portion and the outflow portion. The transition portion includes a plurality of axial frame members, and three of the plurality of axial frame members are commissure posts. At least two of the plurality of the axial frame members are commissure posts having a first end connected to a crown of the inflow portion and an unattached second end disposed within the outflow portion such that a pair of struts of the outflow portion intersect each commis-
(Continued)

sure post at a mid-portion thereof. The prosthetic valve is configured to substantially block blood flow in one direction to regulate blood flow through a central lumen of the stent.

24 Claims, 45 Drawing Sheets

(58) Field of Classification Search
CPC ...... A61F 2/82; A61F 2/89; A61F 2/90; A61F 2230/0054; A61F 2/2412; A61F 2210/0014; A61F 2220/0091; A61F 2250/0063; A61F 2/2439; A61F 2/2463; A61F 2/246; A61F 2/88
See application file for complete search history.

(56) References Cited

U.S. PATENT DOCUMENTS

| | | | |
|---|---|---|---|
| 5,840,081 A | 11/1998 | Andersen et al. | |
| 5,931,969 A | 8/1999 | Carpentier et al. | |
| 6,168,614 B1 | 1/2001 | Andersen et al. | |
| 6,210,957 B1 | 4/2001 | Carpentier et al. | |
| 6,214,054 B1 | 4/2001 | Cunanan et al. | |
| 6,458,153 B1 | 10/2002 | Bailey et al. | |
| 6,547,827 B2 | 4/2003 | Carpentier et al. | |
| 6,561,970 B1 | 5/2003 | Carpentier et al. | |
| 6,582,462 B1 | 6/2003 | Andersen et al. | |
| 6,730,118 B2 | 5/2004 | Spenser et al. | |
| 6,830,584 B1 | 12/2004 | Sequin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,198,646 B2 | 4/2007 | Figulla et al. | |
| 7,201,772 B2 | 4/2007 | Schwammenthal et al. | |
| 7,214,344 B2 | 5/2007 | Carpentier et al. | |
| 7,252,682 B2 | 8/2007 | Seguin | |
| 7,329,278 B2 | 2/2008 | Seguin et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| RE40,570 E | 11/2008 | Carpentier et al. | |
| 7,470,285 B2 | 12/2008 | Nugent | |
| 7,510,575 B2 | 3/2009 | Spenser et al. | |
| 7,530,253 B2 | 5/2009 | Spenser et al. | |
| 7,585,321 B2 | 9/2009 | Cribier | |
| 7,618,446 B2 | 11/2009 | Andersen et al. | |
| 7,682,390 B2 | 3/2010 | Seguin | |
| 7,780,723 B2 | 8/2010 | Taylor | |
| 7,780,726 B2 | 8/2010 | Seguin | |
| 7,789,909 B2 | 9/2010 | Andersen et al. | |
| 7,846,203 B2 | 12/2010 | Cribier | |
| 7,993,394 B2 | 8/2011 | Hariton et al. | |
| 8,163,011 B2 | 4/2012 | Rankin | |
| 8,236,045 B2 | 8/2012 | Benichou et al. | |
| 8,454,685 B2 | 6/2013 | Hariton et al. | |
| 8,454,686 B2* | 6/2013 | Alkhatib | A61F 2/2418 623/2.18 |
| 8,747,461 B2 | 6/2014 | Centola | |
| 8,926,694 B2* | 1/2015 | Costello | A61F 2/2436 623/2.11 |
| 9,089,422 B2 | 7/2015 | Ryan et al. | |
| 9,161,835 B2 | 10/2015 | Rankin et al. | |
| 9,168,131 B2 | 10/2015 | Yohanan et al. | |
| 9,226,820 B2 | 1/2016 | Braido et al. | |
| 9,364,321 B2 | 6/2016 | Alkhatib et al. | |
| 9,414,911 B2 | 8/2016 | Braido et al. | |
| 9,474,604 B2 | 10/2016 | Centola et al. | |
| 9,532,868 B2 | 1/2017 | Braido | |
| 9,572,660 B2 | 2/2017 | Braido et al. | |
| 9,585,752 B2 | 3/2017 | Chang et al. | |
| 9,610,157 B2* | 4/2017 | Braido | A61F 2/2418 |
| 9,707,075 B2 | 7/2017 | Straubinger et al. | |
| 9,901,447 B2* | 2/2018 | Braido | A61F 2/2418 |
| 9,943,407 B2 | 4/2018 | Tuval et al. | |
| 9,949,826 B2 | 4/2018 | Alkhatib | |
| 10,058,420 B2 | 8/2018 | Levi | |
| 10,080,653 B2 | 9/2018 | Conklin et al. | |
| 10,321,993 B2 | 6/2019 | Li et al. | |
| 10,426,611 B2 | 10/2019 | Hariton et al. | |
| 10,456,246 B2 | 10/2019 | Conklin et al. | |
| 10,478,292 B2 | 11/2019 | Levi et al. | |
| 10,537,423 B2 | 1/2020 | Levi et al. | |
| 10,695,170 B2 | 6/2020 | Conklin et al. | |
| 10,709,555 B2* | 7/2020 | Schreck | A61F 2/2418 |
| 10,856,970 B2* | 12/2020 | Tuval | A61F 2/2433 |
| 10,973,631 B2* | 4/2021 | Scheinblum | A61F 2/2412 |
| 10,993,804 B2* | 5/2021 | Braido | A61F 2/2418 |
| 11,083,575 B2* | 8/2021 | Gao | A61F 2/2418 |
| 11,147,667 B2* | 10/2021 | Yohanan | A61F 2/2418 |
| 11,185,405 B2* | 11/2021 | Girard | A61F 2/2469 |
| 11,207,178 B2 | 12/2021 | Conklin | |
| 11,284,999 B2* | 3/2022 | Tabor | A61F 2/2418 |
| 11,357,624 B2* | 6/2022 | Guyenot | A61F 2/2442 |
| 11,399,934 B2 | 8/2022 | Delgado et al. | |
| 11,504,231 B2* | 11/2022 | Carlino | A61F 2/2409 |
| 11,596,515 B2 | 3/2023 | Benichou et al. | |
| 11,602,428 B2 | 3/2023 | Chuter et al. | |
| 11,648,109 B2* | 5/2023 | Peterson | A61F 2/2433 623/2.18 |
| 11,690,710 B2 | 7/2023 | Yohanan et al. | |
| 11,690,718 B2 | 7/2023 | Alon et al. | |
| 11,696,826 B2 | 7/2023 | Hariton et al. | |
| 11,806,233 B2 | 11/2023 | Clapp et al. | |
| 11,877,927 B2* | 1/2024 | Lyer | A61F 2/2418 |
| 2002/0198594 A1* | 12/2002 | Schreck | A61F 2/2436 623/2.11 |
| 2003/0114913 A1 | 6/2003 | Spenser et al. | |
| 2006/0025857 A1* | 2/2006 | Bergheim | A61L 27/50 623/2.18 |
| 2006/0122692 A1* | 6/2006 | Gilad | A61F 2/2418 623/1.35 |
| 2006/0178740 A1 | 8/2006 | Stacchino et al. | |
| 2006/0235505 A1 | 10/2006 | Oepen et al. | |
| 2006/0259137 A1* | 11/2006 | Artof | A61F 2/243 623/2.11 |
| 2007/0078510 A1 | 4/2007 | Ryan | |
| 2007/0270944 A1 | 11/2007 | Bergheim et al. | |
| 2008/0004688 A1* | 1/2008 | Spenser | A61F 2/9524 623/2.14 |
| 2008/0071369 A1* | 3/2008 | Tuval | A61F 2/2436 623/2.38 |
| 2008/0154355 A1* | 6/2008 | Benichou | A61F 2/2418 623/1.26 |
| 2009/0099653 A1* | 4/2009 | Suri | A61F 2/2418 623/2.11 |
| 2009/0157175 A1* | 6/2009 | Benichou | A61F 2/2418 623/2.18 |
| 2009/0164006 A1* | 6/2009 | Seguin | A61F 2/2433 623/2.38 |
| 2009/0192591 A1 | 7/2009 | Ryan et al. | |
| 2009/0216310 A1* | 8/2009 | Straubinger | A61F 2/2418 623/1.26 |
| 2009/0216312 A1* | 8/2009 | Straubinger | A61F 2/82 623/1.36 |
| 2009/0287296 A1* | 11/2009 | Manasse | A61F 2/2418 623/1.26 |
| 2009/0287299 A1 | 11/2009 | Tabor et al. | |
| 2010/0036484 A1* | 2/2010 | Hariton | A61F 2/2412 623/2.18 |
| 2010/0094411 A1* | 4/2010 | Tuval | A61F 2/2427 623/2.11 |
| 2010/0100176 A1* | 4/2010 | Elizondo | A61F 2/2418 623/2.38 |
| 2010/0121436 A1* | 5/2010 | Tuval | A61B 34/20 623/2.17 |
| 2010/0168839 A1* | 7/2010 | Braido | A61L 27/3604 623/2.18 |
| 2010/0204781 A1* | 8/2010 | Alkhatib | A61F 2/2445 623/1.26 |
| 2010/0249908 A1* | 9/2010 | Chau | A61F 2/2418 623/1.26 |
| 2010/0268332 A1 | 10/2010 | Tuval et al. | |

(56) References Cited

U.S. PATENT DOCUMENTS

| | | | |
|---|---|---|---|
| 2011/0015729 A1 | 1/2011 | Jimenez et al. | |
| 2011/0022157 A1* | 1/2011 | Essinger | A61F 2/2436 623/1.11 |
| 2011/0098800 A1* | 4/2011 | Braido | A61F 2/2418 623/1.26 |
| 2011/0166636 A1 | 7/2011 | Rowe | |
| 2011/0224780 A1* | 9/2011 | Tabor | A61F 2/2418 623/1.24 |
| 2011/0264196 A1 | 10/2011 | Savage et al. | |
| 2011/0295363 A1* | 12/2011 | Girard | A61F 2/2412 623/1.26 |
| 2011/0301700 A1 | 12/2011 | Fish et al. | |
| 2011/0313515 A1 | 12/2011 | Quadri et al. | |
| 2011/0319991 A1* | 12/2011 | Hariton | A61F 2/2433 623/2.14 |
| 2012/0053681 A1 | 3/2012 | Alkhatib et al. | |
| 2012/0071969 A1 | 3/2012 | Li et al. | |
| 2012/0078347 A1* | 3/2012 | Braido | A61F 2/915 623/1.26 |
| 2012/0078356 A1 | 3/2012 | Fish et al. | |
| 2012/0078357 A1* | 3/2012 | Conklin | A61F 2/2412 623/2.18 |
| 2012/0123529 A1 | 5/2012 | Levi et al. | |
| 2012/0271398 A1* | 10/2012 | Essinger | A61F 2/2412 623/1.11 |
| 2013/0018458 A1* | 1/2013 | Yohanan | A61F 2/2436 623/2.38 |
| 2013/0023984 A1* | 1/2013 | Conklin | A61F 2/2418 623/2.14 |
| 2013/0058556 A1 | 3/2013 | Ohishi et al. | |
| 2013/0150956 A1* | 6/2013 | Yohanan | A61F 2/2418 623/2.14 |
| 2013/0325107 A1 | 12/2013 | Wu | |
| 2013/0325114 A1* | 12/2013 | McLean | A61F 2/2418 623/2.12 |
| 2014/0081383 A1* | 3/2014 | Eberhardt | A61F 2/2418 623/1.24 |
| 2014/0155997 A1* | 6/2014 | Braido | A61F 2/2409 623/2.37 |
| 2014/0172082 A1* | 6/2014 | Bruchman | A61F 2/2418 156/185 |
| 2014/0277389 A1 | 9/2014 | Braido et al. | |
| 2014/0330372 A1* | 11/2014 | Weston | A61F 2/2418 623/2.37 |
| 2014/0343671 A1* | 11/2014 | Yohanan | A61F 2/2418 623/2.18 |
| 2014/0350667 A1* | 11/2014 | Braido | A61F 2/2427 623/2.11 |
| 2015/0018944 A1* | 1/2015 | O'Connell | A61F 2/2427 623/2.42 |
| 2015/0073546 A1* | 3/2015 | Braido | A61L 27/3604 623/2.18 |
| 2015/0157455 A1* | 6/2015 | Hoang | A61M 25/01 264/269 |
| 2015/0230923 A1* | 8/2015 | Levi | A61F 2/2418 623/2.36 |
| 2015/0320556 A1* | 11/2015 | Levi | A61F 2/2412 29/515 |
| 2016/0296324 A1 | 10/2016 | Bapat et al. | |
| 2016/0296328 A1* | 10/2016 | Tabor | A61F 2/07 |
| 2016/0354205 A1* | 12/2016 | Essinger | A61F 2/2436 |
| 2017/0014229 A1* | 1/2017 | Nguyen-Thien-Nhon | A61F 2/2418 |
| 2017/0042673 A1* | 2/2017 | Vietmeier | A61F 2/2418 |
| 2018/0021127 A1* | 1/2018 | Yohanan | A61F 2/2412 623/1.13 |
| 2018/0344458 A1* | 12/2018 | Spenser | A61F 2/2427 |
| 2019/0076245 A1* | 3/2019 | Arcaro | A61F 2/2418 |
| 2019/0117424 A1 | 4/2019 | Berra | |
| 2019/0192275 A1 | 6/2019 | Kim et al. | |
| 2019/0247177 A1 | 8/2019 | Kim | |
| 2019/0262507 A1 | 8/2019 | Adamek-Bowers et al. | |
| 2019/0336283 A1 | 11/2019 | Le Cerf et al. | |
| 2020/0306040 A1* | 10/2020 | Fung | A61F 2/2436 |
| 2020/0360134 A1* | 11/2020 | Peterson | A61F 2/2433 |
| 2021/0275298 A1* | 9/2021 | Peterson | A61F 2/2418 |
| 2022/0054260 A1 | 2/2022 | Koop et al. | |
| 2022/0061985 A1* | 3/2022 | Peterson | A61F 2/2418 |
| 2022/0160502 A1* | 5/2022 | Jin | A61F 2/90 |
| 2022/0175521 A1* | 6/2022 | Baldwin | A61F 2/2418 |
| 2022/0211493 A1* | 7/2022 | Benichou | A61F 2/2412 |
| 2022/0218468 A1* | 7/2022 | Hoang | A61F 2/2412 |
| 2023/0017818 A1 | 1/2023 | Essinger et al. | |
| 2023/0028648 A1* | 1/2023 | Neuberger | A61F 2/2418 |
| 2023/0038809 A1* | 2/2023 | Clapp | A61F 2/2427 |
| 2023/0111680 A1* | 4/2023 | Leichner | A61F 2/2418 623/2.11 |
| 2023/0113881 A1 | 4/2023 | Essinger et al. | |
| 2023/0165678 A1* | 6/2023 | Nir | A61F 2/9517 623/2.17 |
| 2023/0263623 A1* | 8/2023 | Peterson | A61F 2/2418 623/2.1 |
| 2024/0008981 A1* | 1/2024 | O'Connor | A61F 2/2442 |
| 2024/0024101 A1* | 1/2024 | Levi | A61F 2/2418 |

FOREIGN PATENT DOCUMENTS

| | | |
|---|---|---|
| EP | 3501455 B1 | 12/2019 |
| WO | 2003011195 A2 | 2/2003 |
| WO | 20060127765 A1 | 11/2006 |
| WO | 2008150529 A1 | 12/2008 |
| WO | 2010141847 A1 | 12/2010 |
| WO | WO2011137531 A1 | 11/2011 |
| WO | 2012032187 A1 | 3/2012 |
| WO | WO2015126711 A1 | 8/2015 |
| WO | WO2017103830 A1 | 6/2017 |
| WO | WO2021040547 A1 | 3/2021 |

* cited by examiner

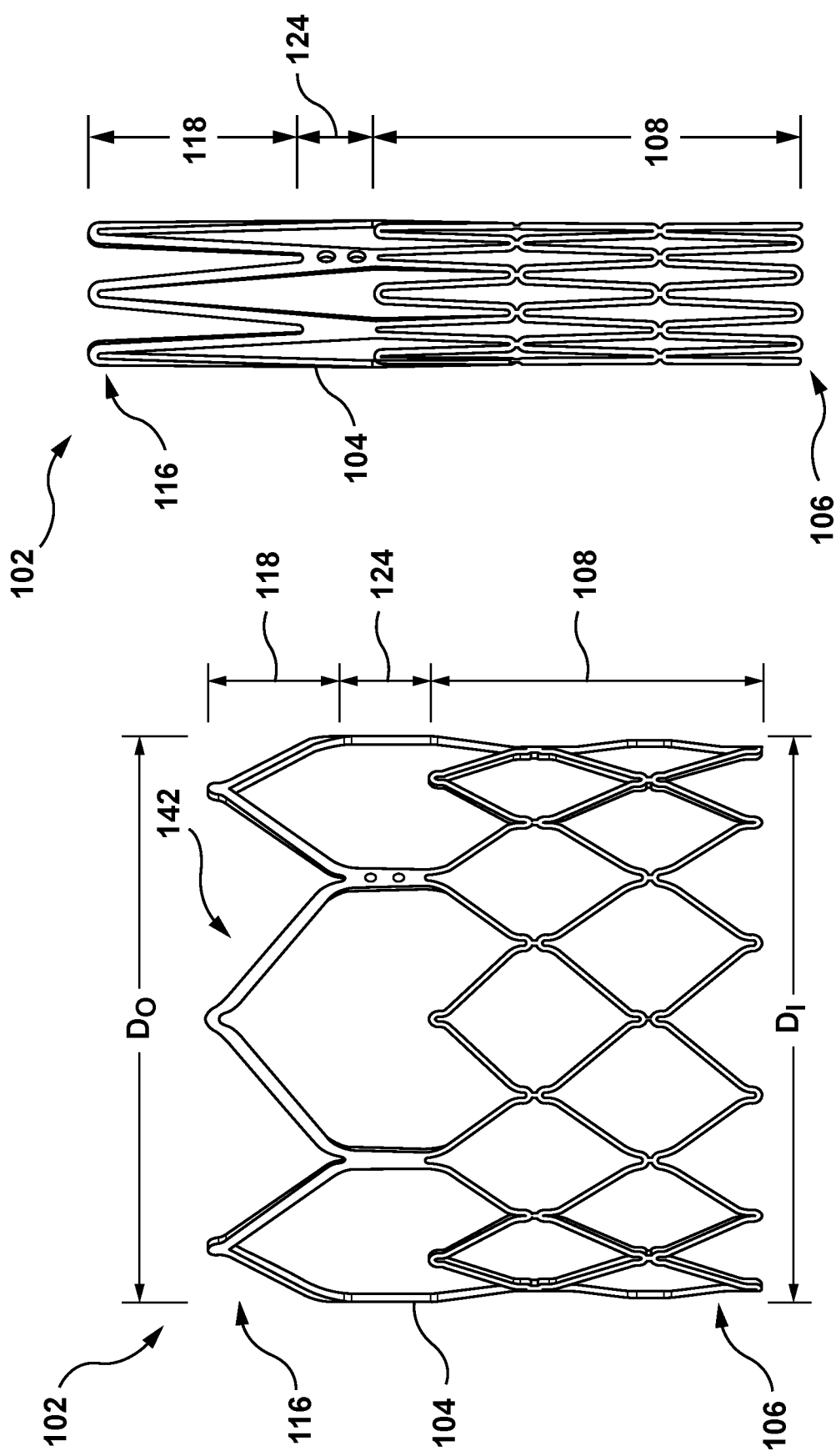

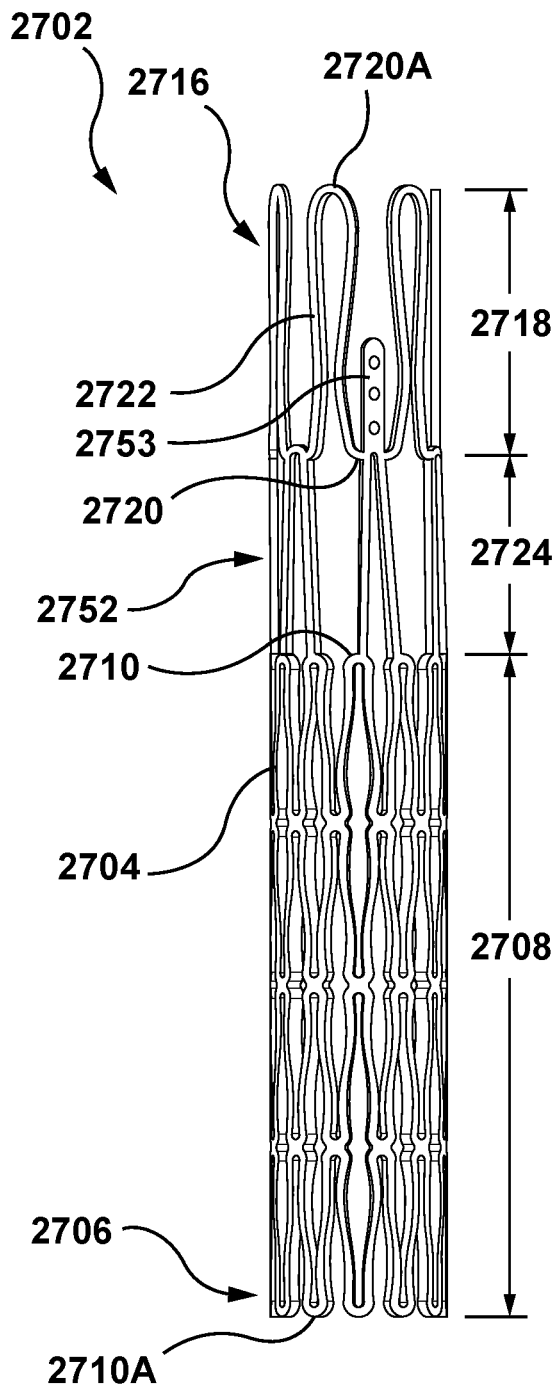
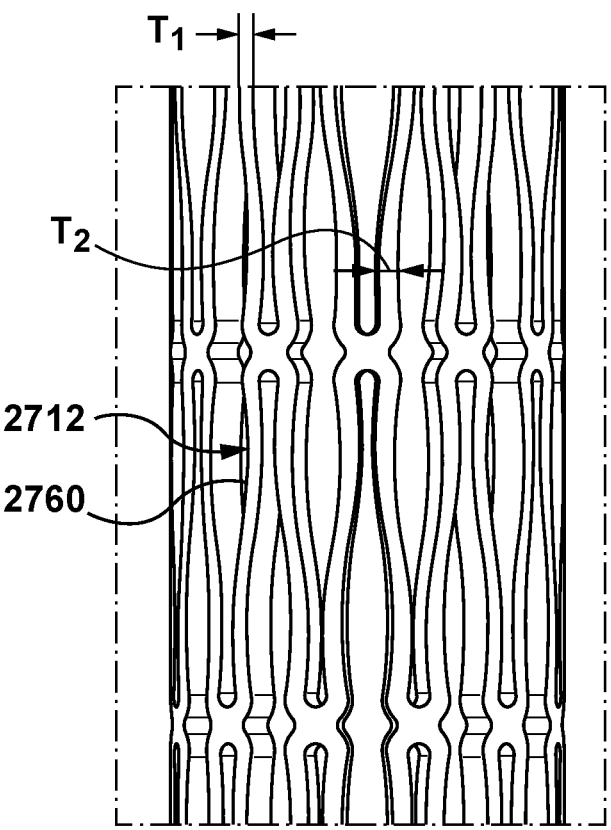
FIG. 27
FIG. 27A

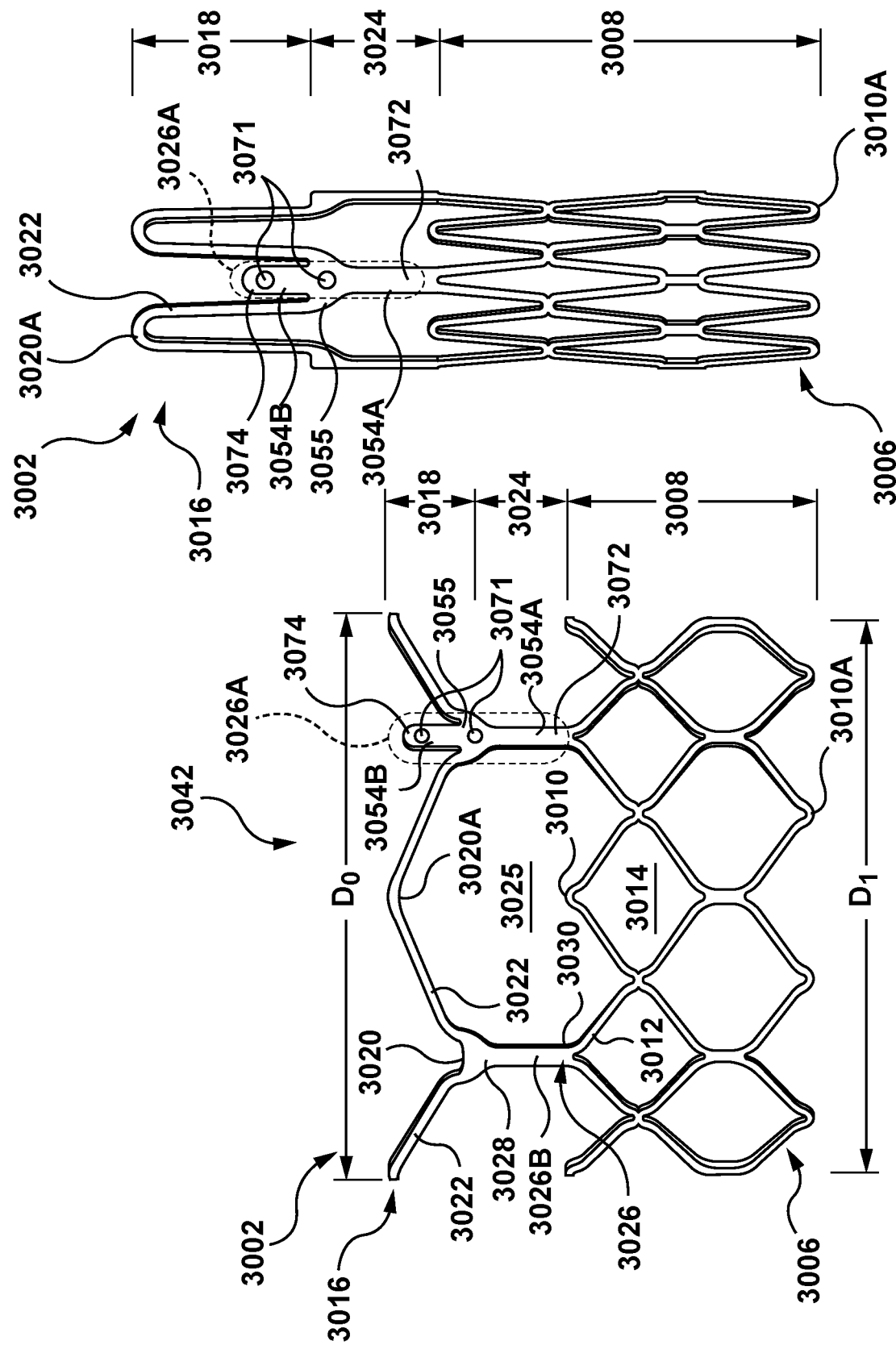

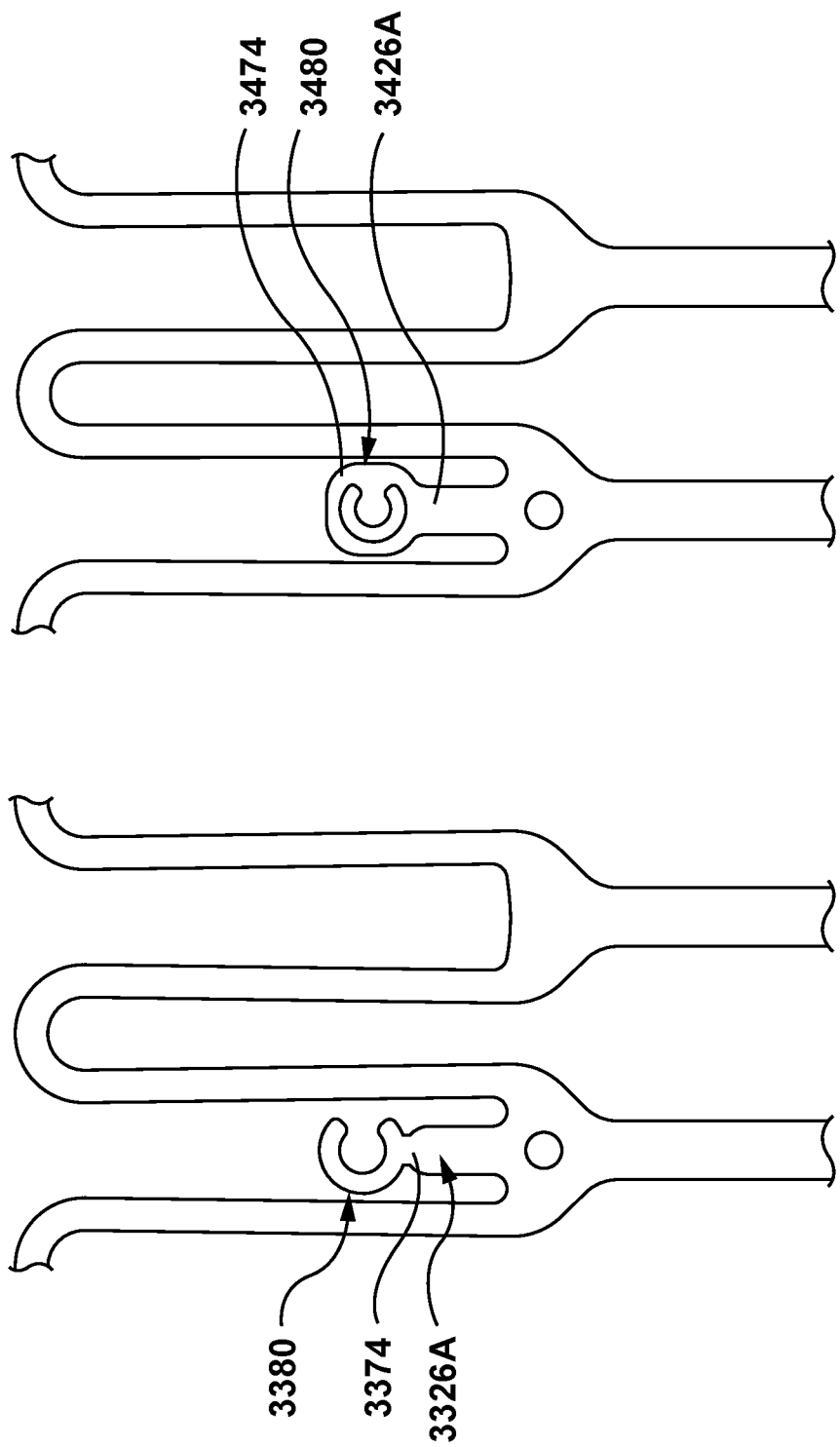

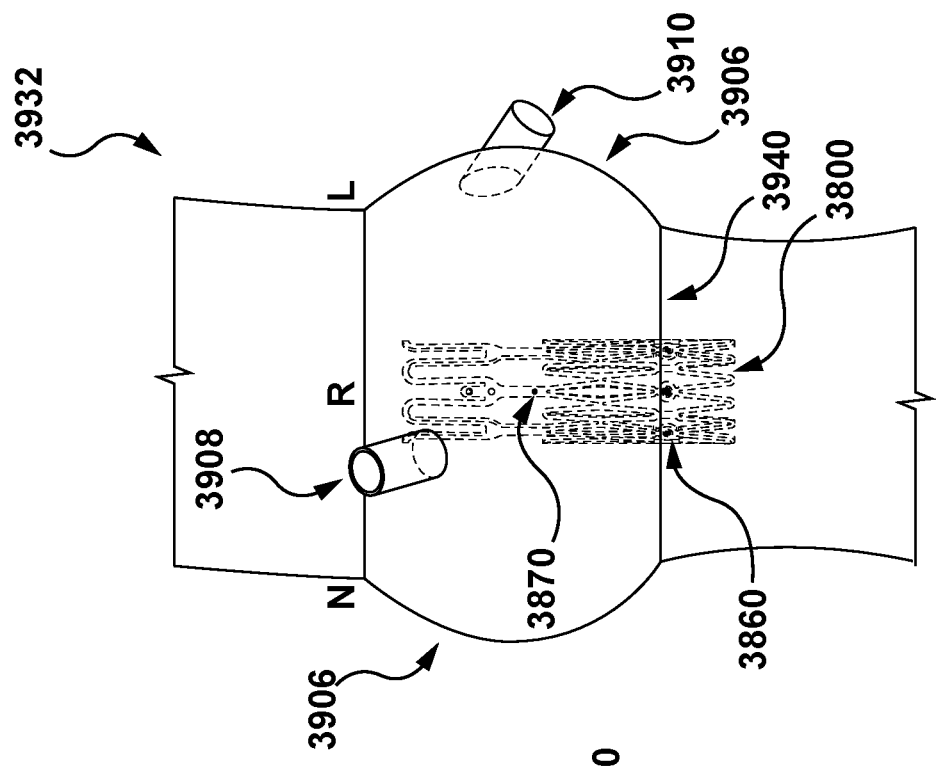
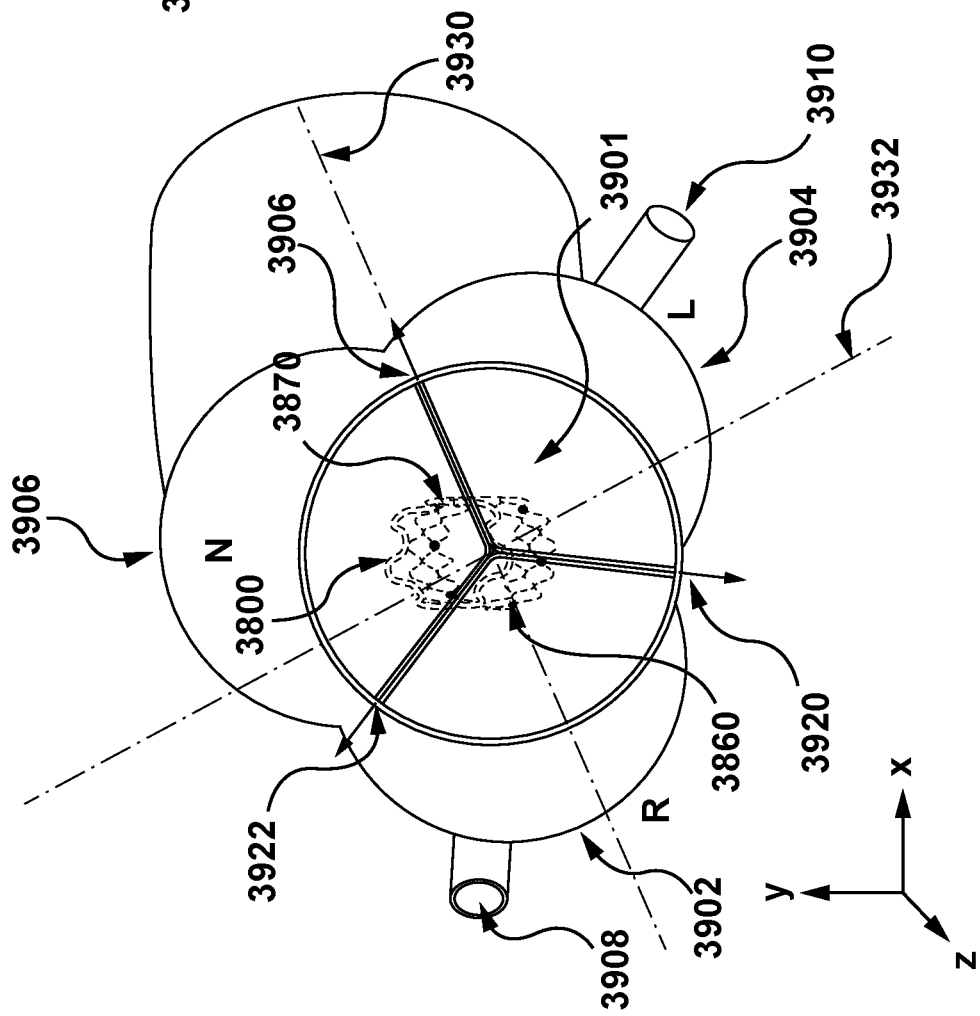
FIG. 39B
FIG. 39A

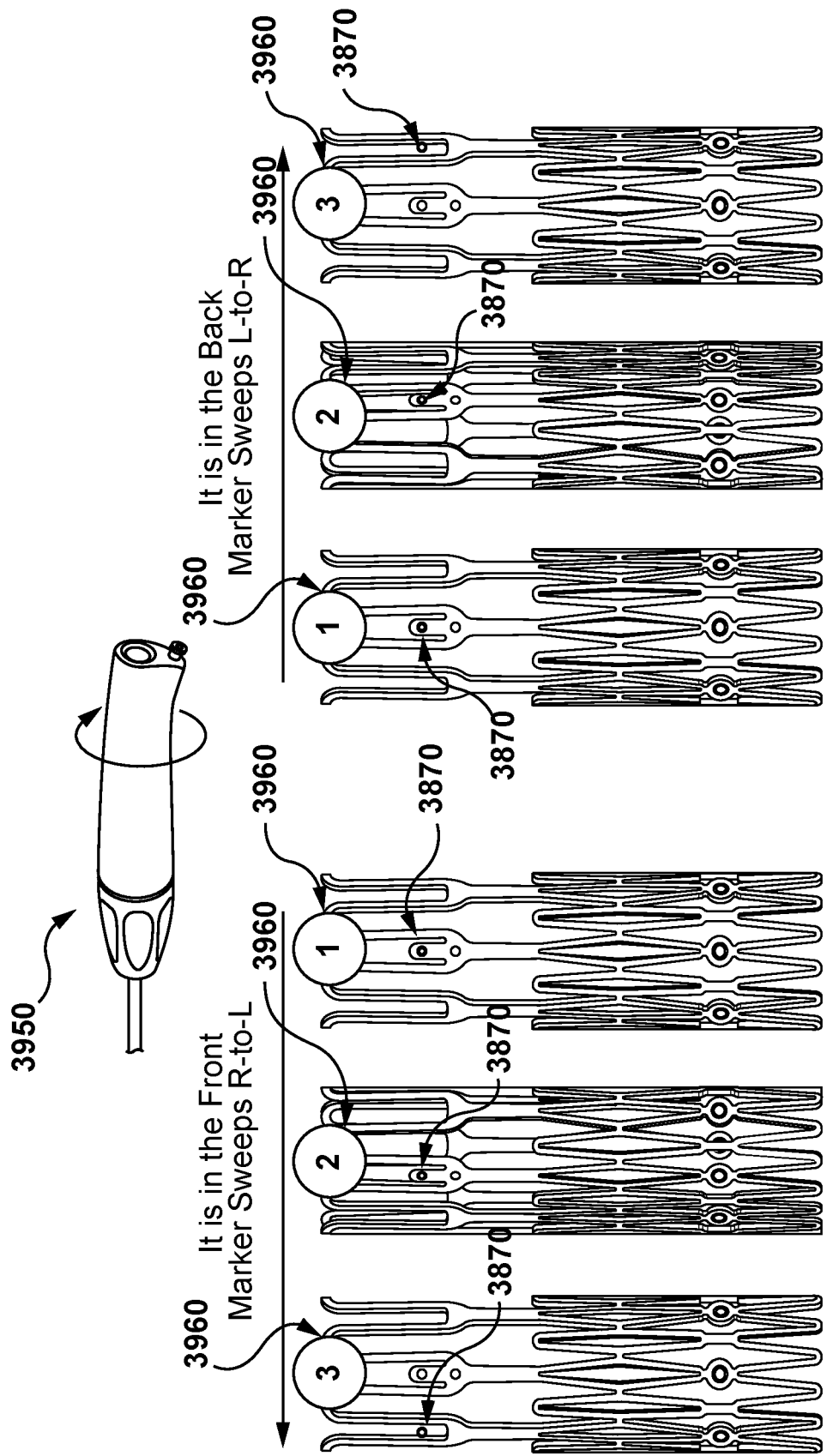

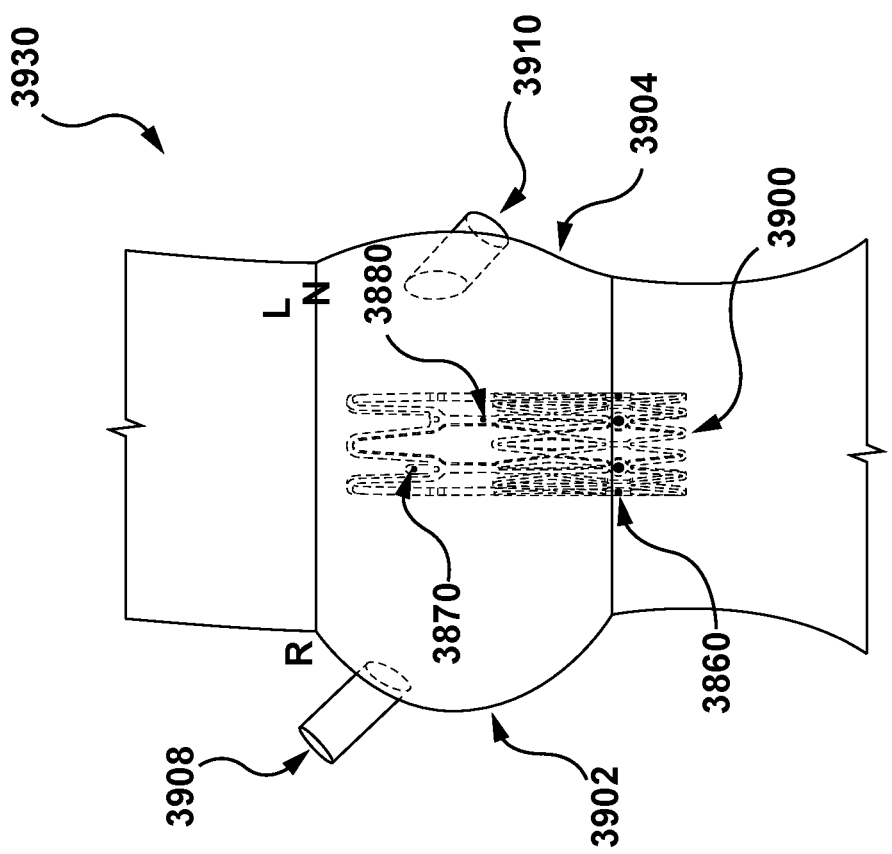

BALLOON EXPANDABLE STENT WITH LENGTHENED COMMISSURE POSTS FOR TRANSCATHETER IMPLANTATION OF A CARDIAC VALVE PROSTHESIS

CROSS-REFERENCE TO RELATED APPLICATIONS

This application claims the benefit of U.S. Provisional Patent Application Ser. No. 62/985,131, filed Mar. 4, 2020, which is hereby incorporated by reference in its entirety for all purposes.

FIELD OF THE INVENTION

The present invention relates to transcatheter valve prostheses that are radially expandable by a balloon.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place.

When designing a prosthetic valve, valve-frame integration and frame mechanical performance often have competing needs or requirements. For example, when attaching the valve to the frame during valve-frame integration, the valve itself needs to be reinforced to the frame at certain locations without hindering mechanical performance of the frame. Embodiments hereof relate to an improved balloon-expandable transcatheter valve prosthesis configured to minimize tradeoffs between the above-described competing needs.

BRIEF SUMMARY OF THE INVENTION

According to a first embodiment hereof, the present disclosure provides a transcatheter valve prosthesis including a stent having a crimped configuration for delivery within a vasculature and an expanded configuration for deployment within a native heart valve and a prosthetic valve. The stent includes an inflow portion formed proximate to an inflow end of the stent, an outflow portion formed proximate to an outflow end of the stent, and a transition portion extending between the inflow portion and the outflow portion. The inflow portion includes a plurality of crowns and a plurality of struts with each crown being formed between a pair of opposing struts, a plurality of side openings being defined by the plurality of crowns and the plurality of struts, and endmost inflow side openings and endmost inflow crowns are formed at the inflow end of the stent. The outflow portion includes a plurality of crowns and a plurality of struts with each crown being formed between a pair of opposing struts, and endmost outflow crowns are formed at the outflow end of the stent. The inflow end of the stent has a first diameter and the outflow end of the stent has a second diameter. A total of the endmost inflow crowns is greater than a total of the endmost outflow crowns. The transition portion includes a plurality of axial frame members. At least two of the plurality of the axial frame members are commissure posts having a first end connected to a crown of the inflow portion and an unattached second end disposed within the outflow portion such that a pair of struts of the outflow portion intersect each commissure post at a mid-portion thereof. The prosthetic valve is disposed within and secured to at least the transition portion of the stent. The prosthetic valve is configured to substantially block blood flow in one direction to regulate blood flow through a central lumen of the stent.

In an aspect of the first embodiment, and in combination with any other aspects herein, the disclosure provides that the prosthetic valve includes three leaflets and three commissures, each commissure being formed by attached adjacent lateral ends of an adjoining pair of the three leaflets.

In an aspect of the first embodiment, and in combination with any other aspects herein, the disclosure provides that the transition portion includes a total of six axial frame members, with three of the six axial frame members being commissure posts, each axial frame member disposed approximately halfway between a pair of adjacent endmost outflow crowns. The commissure posts are aligned with and attached to a respective commissure of the three leaflets of the prosthetic valve.

In an aspect of the first embodiment, and in combination with any other aspects herein, the disclosure provides that a height of the stent in the expanded configuration is between 12 and 21 mm, the height being measured between the endmost inflow crowns the endmost outflow crowns.

In an aspect of the first embodiment, and in combination with any other aspects herein, the disclosure provides that the stent is configured for intra-annular placement within a native aortic valve.

In an aspect of the first embodiment, and in combination with any other aspects herein, the disclosure provides that the stent is configured for supra-annular placement within a native aortic valve.

In an aspect of the first embodiment, and in combination with any other aspects herein, the disclosure provides that the transition portion includes a total of six axial frame members and a total of six endmost outflow side openings are formed at the outflow end of the stent, each endmost outflow side opening being defined by two struts of the outflow portion, four struts of the inflow portion, and two axial frame members of the transition portion.

In an aspect of the first embodiment, and in combination with any other aspects herein, the disclosure provides that each endmost outflow side opening is defined by two adjacent struts of the outflow portion, four adjacent struts of the inflow portion, and two adjacent axial frame members of the transition portion.

In an aspect of the first embodiment, and in combination with any other aspects herein, the disclosure provides that the unattached second end of each commissure post does not extend beyond the endmost outflow crowns of the outflow portion.

In an aspect of the first embodiment, and in combination with any other aspects herein, the disclosure provides that each commissure post extends substantially parallel to a central longitudinal axis of the stent.

In an aspect of the first embodiment, and in combination with any other aspects herein, the disclosure provides that the stent is balloon expandable.

In an aspect of the first embodiment, and in combination with any other aspects herein, the disclosure provides that the first diameter of the inflow end of the stent and the second diameter of the outflow end of the stent are substantially similar.

In an aspect of the first embodiment, and in combination with any other aspects herein, the disclosure provides that a directional marker is formed on the at least one commissure post. In an embodiment, the directional marker is an axially non-symmetrical element or opening. In an embodiment, the directional marker is a C-shaped element or a P-shaped element. In an embodiment, the directional marker is a C-shaped opening or a P-shaped opening.

In an aspect of the first embodiment, and in combination with any other aspects herein, the disclosure provides that a directional marker is formed on the at least one commissure post closer to the first end thereof.

In an aspect of the first embodiment, and in combination with any other aspects herein, the disclosure provides that a directional marker is formed on the at least one commissure post closer to the unattached second end thereof.

In an aspect of the first embodiment, and in combination with any other aspects herein, the disclosure provides that a directional marker is formed on the mid-portion of the at least one commissure post.

In an aspect of the first embodiment, and in combination with any other aspects herein, the disclosure provides that the total of the endmost inflow crowns are twice the total of the endmost outflow crowns.

According to a second embodiment hereof, the present disclosure provides a transcatheter valve prosthesis including a stent having a crimped configuration for delivery within a vasculature and an expanded configuration for deployment within a native heart valve. The stent includes a plurality of axial frame members, an inflow portion including at least three rows of struts and crowns formed between adjacent pairs of said struts, and an outflow portion including a single row of struts and crowns formed between adjacent pair of said struts. The at least three rows of the inflow portion are formed between an inflow end of the axial frame members and an inflow end of the stent. The outflow portion is coupled to an outflow end of the axial frame members. Exactly two struts of the plurality of struts of the outflow portion are disposed between adjacent axial frame members. At least two of the plurality of the axial frame members are commissure posts having a first end connected to a crown of the inflow portion and an unattached second end disposed within the outflow portion such that a pair of struts of the outflow portion intersect each commissure post at a mid-portion thereof. A directional marker is formed on at least one commissure post.

In an aspect of the second embodiment, and in combination with any other aspects herein, the disclosure provides that the plurality of axial frame members includes exactly six axial frame members, three of the six axial frame members are commissure posts and three of the six axial frame members are axial struts, and each of the axial struts is disposed between adjacent commissure posts.

In an aspect of the second embodiment, and in combination with any other aspects herein, the disclosure provides that the transcatheter valve prosthesis also includes a prosthetic valve including three leaflets, and each commissure of the leaflets is coupled to a corresponding commissure post of the stent.

In an aspect of the second embodiment, and in combination with any other aspects herein, the disclosure provides that one of the at least three rows of struts and crowns of the inflow portion includes crowns coupled to inflow end of the axial frame member. The one row includes at least four struts between adjacent axial frame members. In an embodiment, the one row includes exactly four struts between adjacent axial frame members.

In an aspect of the second embodiment, and in combination with any other aspects herein, the disclosure provides that the inflow portion includes exactly three rows of a plurality of struts and crowns.

In an aspect of the second embodiment, and in combination with any other aspects herein, the disclosure provides that the plurality of axial frame members includes a plurality of axial struts and a plurality of commissure posts. There are the same number of axial struts and commissure posts, and each of the axial struts is disposed between adjacent commissure posts.

In an aspect of the second embodiment, and in combination with any other aspects herein, the disclosure provides that the unattached second end of each commissure post does not extend beyond endmost outflow crowns of the outflow portion.

In an aspect of the second embodiment, and in combination with any other aspects herein, the disclosure provides that each commissure post extends substantially parallel to a central longitudinal axis of the stent.

In an aspect of the second embodiment, and in combination with any other aspects herein, the disclosure provides that the stent is balloon expandable.

In an aspect of the second embodiment, and in combination with any other aspects herein, the disclosure provides that a diameter of the inflow end of the stent is substantially the same as a diameter of the outflow end of the stent.

In an aspect of the second embodiment, and in combination with any other aspects herein, the disclosure provides that the directional marker is an axially non-symmetrical element or opening. In an embodiment, the directional marker is a C-shaped element. In an embodiment, the directional marker is a P-shaped element. In an embodiment, the directional marker is a C-shaped opening. In an embodiment, the directional marker is a P-shaped opening.

In an aspect of the second embodiment, and in combination with any other aspects herein, the disclosure provides that a directional marker is formed on the at least one commissure post closer to the first end thereof.

In an aspect of the second embodiment, and in combination with any other aspects herein, the disclosure provides that a directional marker is formed on the at least one commissure post closer to the unattached second end thereof.

In an aspect of the second embodiment, and in combination with any other aspects herein, the disclosure provides that a directional marker is formed on the mid-portion of the at least one commissure post.

According to a third embodiment hereof, the present disclosure provides a transcatheter valve prosthesis including a stent having a crimped configuration for delivery within a vasculature and an expanded configuration for deployment within a native heart valve. The stent includes an inflow portion formed proximate to an inflow end of the stent, the inflow portion including a plurality of crowns and a plurality of struts with each crown being formed between a pair of opposing struts. A plurality of side openings are defined by the plurality of crowns and the plurality of struts, and endmost inflow side openings and endmost inflow crowns are formed at the inflow end of the stent. The stent also includes an outflow portion formed proximate to an outflow end of the stent, the outflow portion including a plurality of crowns and a plurality of struts with each crown being formed between a pair of opposing struts. Endmost outflow crowns are formed at the outflow end of the stent. A diameter of the inflow end of the stent is substantially the same as a diameter of the outflow end of the stent, and a total of the endmost inflow crowns are twice a total of the endmost outflow crowns. The stent also includes a transition portion extending between the inflow portion and the outflow portion. The transition portion includes a plurality of transition frame members. Each transition frame member includes a first strut that extends from a crown of the outflow portion to a first crown of the inflow portion and a second strut that extends from the crown of the outflow portion to a second crown of the inflow portion that is adjacent to the first crown of the inflow portion. At least two of the plurality of the transition frame members form commissure cells having a material flap attached to thereto that spans between the first and second struts of a transition frame member and a pair of adjacent struts of the inflow portion. A commissure extension extends from each of the commissure cells into the outflow portion of the stent. A prosthetic valve is disposed within and secured to at least the transition portion of the stent, the prosthetic valve being configured to substantially block blood flow in one direction to regulate blood flow through a central lumen of the stent.

In an aspect of the third embodiment, and in combination with any other aspects herein, the disclosure provides that the prosthetic valve includes three leaflets and three commissures, each commissure being formed by attached adjacent lateral ends of an adjoining pair of the three leaflets.

In an aspect of the third embodiment, and in combination with any other aspects herein, the disclosure provides that the transition portion includes a total of six transition frame members, with three of the six transition frame members forming commissure cells, each transition frame member disposed approximately halfway between a pair of adjacent endmost outflow crowns. The commissures of the three leaflets of the prosthetic valve are aligned with and attached to the material flap of a respective commissure cell.

In an aspect of the third embodiment, and in combination with any other aspects herein, the disclosure provides that a height of the stent in the expanded configuration is between 12 and 21 mm, the height being measured between the endmost inflow crowns the endmost outflow crowns.

In an aspect of the third embodiment, and in combination with any other aspects herein, the disclosure provides that the stent is configured for intra-annular placement within a native aortic valve.

In an aspect of the third embodiment, and in combination with any other aspects herein, the disclosure provides that the stent is balloon expandable.

In an aspect of the third embodiment, and in combination with any other aspects herein, the disclosure provides that each commissure extension is an axial segment having a first end attached to a transition frame member and an unattached second end disposed within the outflow portion. The unattached second end of each commissure extension does not extend beyond the endmost outflow crowns of the outflow portion.

In an aspect of the third embodiment, and in combination with any other aspects herein, the disclosure provides that each commissure extension extends substantially parallel to a central longitudinal axis of the stent.

In an aspect of the third embodiment, and in combination with any other aspects herein, the disclosure provides that each commissure cell and respective material flap is generally diamond-shaped.

In an aspect of the third embodiment, and in combination with any other aspects herein, the disclosure provides that at least one strut of the inflow portion is tapered and the thickness varies along a length thereof such that a middle portion is relatively thinner than opposing end portions of the strut.

In an aspect of the third embodiment, and in combination with any other aspects herein, the disclosure provides that the transition portion includes a total of six transition frame members, with three of the six transition frame members forming commissure cells having a respective material flap attached thereto and three of the six transition frame members forming open cells that do not include a material flap attached thereto.

In an aspect of the third embodiment, and in combination with any other aspects herein, the disclosure provides that a directional marker is formed on at least one commissure extension. In an embodiment, the directional marker is an axially non-symmetrical element or opening. In an embodiment, the directional marker is a C-shaped element. In an embodiment, the directional marker is a P-shaped element. In an embodiment, the directional marker is a C-shaped opening. In an embodiment, the directional marker is a P-shaped opening.

In an aspect of the third embodiment, and in combination with any other aspects herein, the disclosure provides that each commissure extension is an axial segment having a first end attached to a transition frame member and an unattached second end disposed within the outflow portion. A directional marker is formed on the at least one commissure extension closer to the unattached second end thereof.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 4 is a perspective view of the stent of the transcatheter valve prosthesis of FIG. 1, wherein the stent is in the expanded configuration.

FIG. 5 is a side view of the stent of the transcatheter valve prosthesis of FIG. 1, wherein the stent is in a non-expanded or crimped configuration.

FIG. 27 is a side view of a stent according to another embodiment hereof, wherein the stent is in a crimped configuration and the stent includes an s-shaped strut.

FIG. 27A is an enlarged side view of a portion of the stent of FIG. 27, wherein the stent is in a non-expanded or crimped configuration.

FIG. 31 is a side view of the stent of the transcatheter valve prosthesis of FIG. 30, wherein the stent is in an expanded configuration.

FIG. 32 is a side view of the stent of the transcatheter valve prosthesis of FIG. 30, wherein the stent is in a non-expanded or crimped configuration.

FIG. 33 is an enlarged side view of a portion of a lengthened commissure post according to another embodiment hereof, wherein the lengthened commissure post includes a directional marker and the directional marker is a C-shaped element.

FIG. 34 is an enlarged side view of a portion of a lengthened commissure post according to another embodiment hereof, wherein the lengthened commissure post includes a directional marker and the directional marker is a C-shaped opening.

FIGS. 39A-39F illustrate various views of a target site for the transcatheter valve prosthesis of FIGS. 38A-38E in accordance with an embodiment hereof.

FIGS. 41A-41D illustrate various views of a target site for the transcatheter valve prosthesis of FIGS. 40A-40C in accordance with an embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of an aortic heart valve, the invention may also be used where it is deemed useful in other valved intraluminal sites that are not in the heart. For example, the present invention may be applied to other heart valves or venous valves as well. Furthermore, there is no intention to be bound by any expressed or implied theory presented in the preceding technical field, background, brief summary or the following detailed description.

Figure 1:
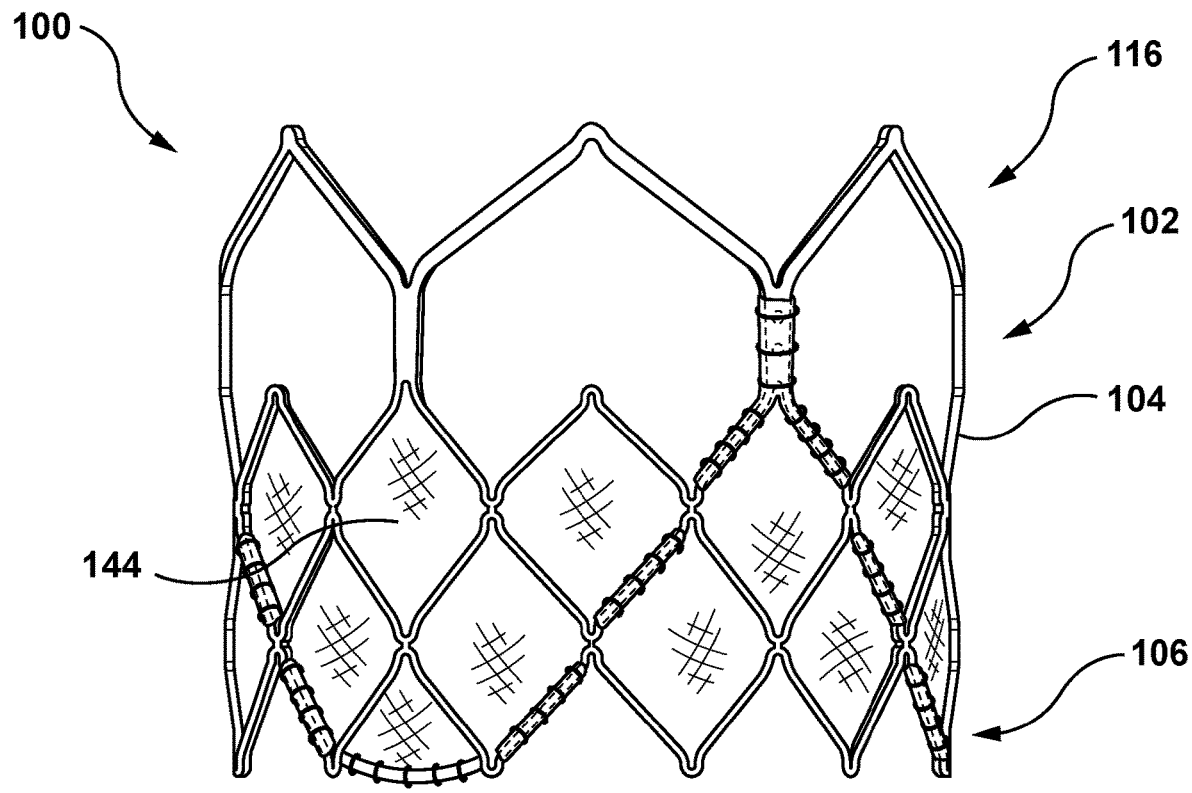
FIG. 1 is a side view of a transcatheter valve prosthesis according to an embodiment hereof, wherein the transcatheter valve prosthesis is in an expanded configuration.
Figure 1A:
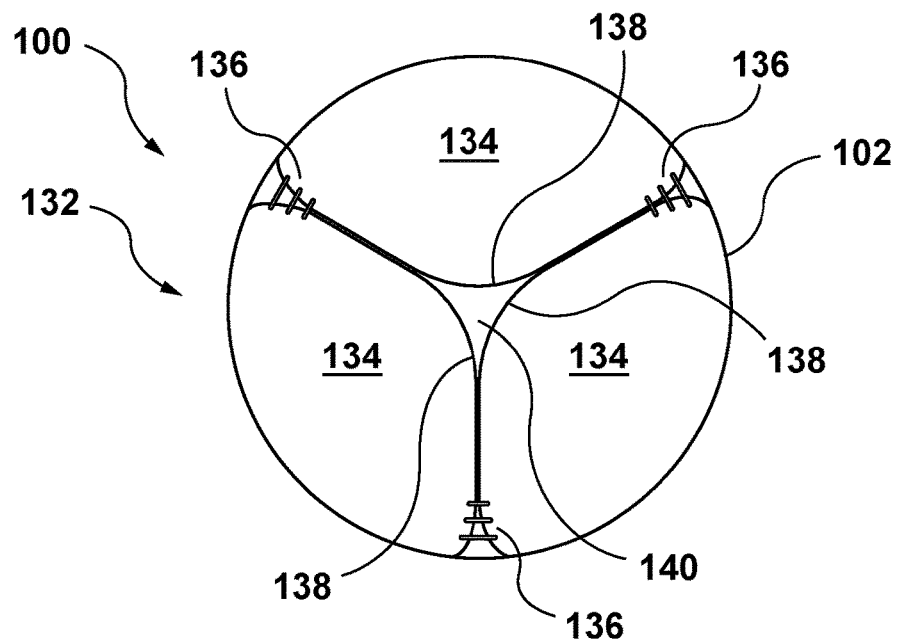
FIG. 1A is an end view illustration of the transcatheter valve prosthesis of FIG. 1.

Embodiments hereof relate to a transcatheter valve prosthesis 100 having a radially-expandable stent 102 and a prosthetic valve 132. The stent 102 is generally tubular, and is mechanically or balloon expandable, having a crimped configuration for delivery within a vasculature and an expanded configuration for deployment within a native heart valve. FIG. 1 is a side view of the transcatheter valve prosthesis 100 in the expanded configuration, while FIG. 1A is an end view illustration of the transcatheter valve prosthesis 100. When the transcatheter valve prosthesis 100 is deployed within the valve annulus of a native heart valve, the stent 102 of the transcatheter valve prosthesis 100 is configured to be radially expanded within native valve leaflets of the patient's defective valve, to thereby retain the native valve leaflets in a permanently open state. In embodiments hereof, the transcatheter valve prosthesis 100 is configured for replacement for an aortic valve such that an inflow end 106 of the transcatheter valve prosthesis 100 extends into and anchors within the aortic annulus of a patient's left ventricle, while an outflow end 116 of the transcatheter valve prosthesis 100 is positioned within the aortic sinuses.

The stent 102 of the transcatheter valve prosthesis 100 may be a unitary frame or scaffold that supports the prosthetic valve 132 including one or more valve leaflets 134 within the interior of the stent 102. The prosthetic valve 132 is capable of blocking flow in one direction to regulate flow there-through via the valve leaflets 134 that may form a bicuspid or tricuspid replacement valve. FIG. 1A is an end view of FIG. 1 taken from the outflow end 116 of the prosthesis and illustrates an exemplary tricuspid valve having three valve leaflets 134, although a bicuspid leaflet configuration may alternatively be used in embodiments hereof. More particularly, as the transcatheter valve prosthesis 100 is configured for placement within a native aortic valve which typically has three leaflets, the prosthetic valve 132 may include three valve leaflets 134. However, the transcatheter valve prosthesis 100 is not required to have the same number of leaflets as the native valve. If the transcatheter valve prosthesis 100 is alternatively configured for placement within a native valve having two leaflets such as the mitral valve, the prosthetic valve 132 may include two or three valve leaflets. The valve leaflets 134 may be attached to a graft material 144 which encloses or lines a portion of the stent 102 as would be known to one of ordinary skill in the art of prosthetic tissue valve construction. The valve leaflets 134 are sutured or otherwise securely and sealingly attached along their bases to the interior surface of the graft material 144, or otherwise attached to the stent 102. Adjoining pairs of leaflets are attached to one another at their lateral ends to form commissures 136, with free edges 138 of the valve leaflets 134 forming coaptation edges that meet in area of coaptation 140.

The valve leaflets 134 may be made of pericardial material; however, the valve leaflets 134 may instead be made of another material. Natural tissue for the valve leaflets 134 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as the valve leaflets 134 include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 144 may enclose or line the stent 102 as would be known to one of ordinary skill in the art of prosthetic tissue valve construction. Graft material 144 may be a natural or biological material such as pericardium or another membranous tissue such as intestinal submucosa. Alternatively, graft material 144 may be a low-porosity woven fabric, such as polyester, Dacron fabric, or PTFE, which creates a one-way fluid passage when attached to the stent. In one embodiment, graft material 144 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

As previously stated, the stent 102 is balloon-expandable as would be understood by one of ordinary skill in the art. As such, the stent 102 is made from a plastically deformable material such that when expanded by a dilatation balloon, the stent 102 maintains its radially expanded configuration. The stent 102 may be formed from stainless steel or other suitable metal, such as platinum iridium, cobalt chromium alloys such as MP35N, or various types of polymers or other materials known to those skilled in the art, including said materials coated with various surface deposits to improve clinical functionality. The stent 102 is configured to be rigid such that it does not deflect or move when subjected to in-vivo forces, or such that deflection or movement is minimized when subjected to in-vivo forces. In an embodiment, the radial stiffness (i.e., a measurement of how much the stent 102 deflects when subjected to in-vivo forces) of the stent 102 is between 80 N/m and 120 N/m, and the radial stiffness of the stent 102 scaled across the deployed height thereof is approximately 5 N/mm². In an embodiment, the radial stiffness of the stent 102 is greater than 100 N/m. Further, in an embodiment, the device recoil (i.e., a measurement of how much the stent 102 relaxes after balloon deployment) is below 15% and the approximately recoil after deployment is between 0.5 mm and 2 mm. Further, in an embodiment, the device crush or yield (i.e., the radial force at which the stent 102 yields) is approximately 200 N.

Delivery of the transcatheter valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. The transcatheter valve prosthesis 100 has a crossing profile of between 15-30 Fr, the crossing profile being defined as the outside diameter (OD) of the transcatheter valve prosthesis 100 after it is crimped onto the balloon and allowed to recoil from the crimping action. During delivery, the transcatheter valve prosthesis 100 remains compressed until it reaches a target diseased native heart valve, at which time a balloon of a delivery system is inflated in order to radially expand the transcatheter valve prosthesis 100 in situ. The delivery system is then removed and the transcatheter valve prosthesis 100 remains deployed within the native target heart valve.

Figure 3:
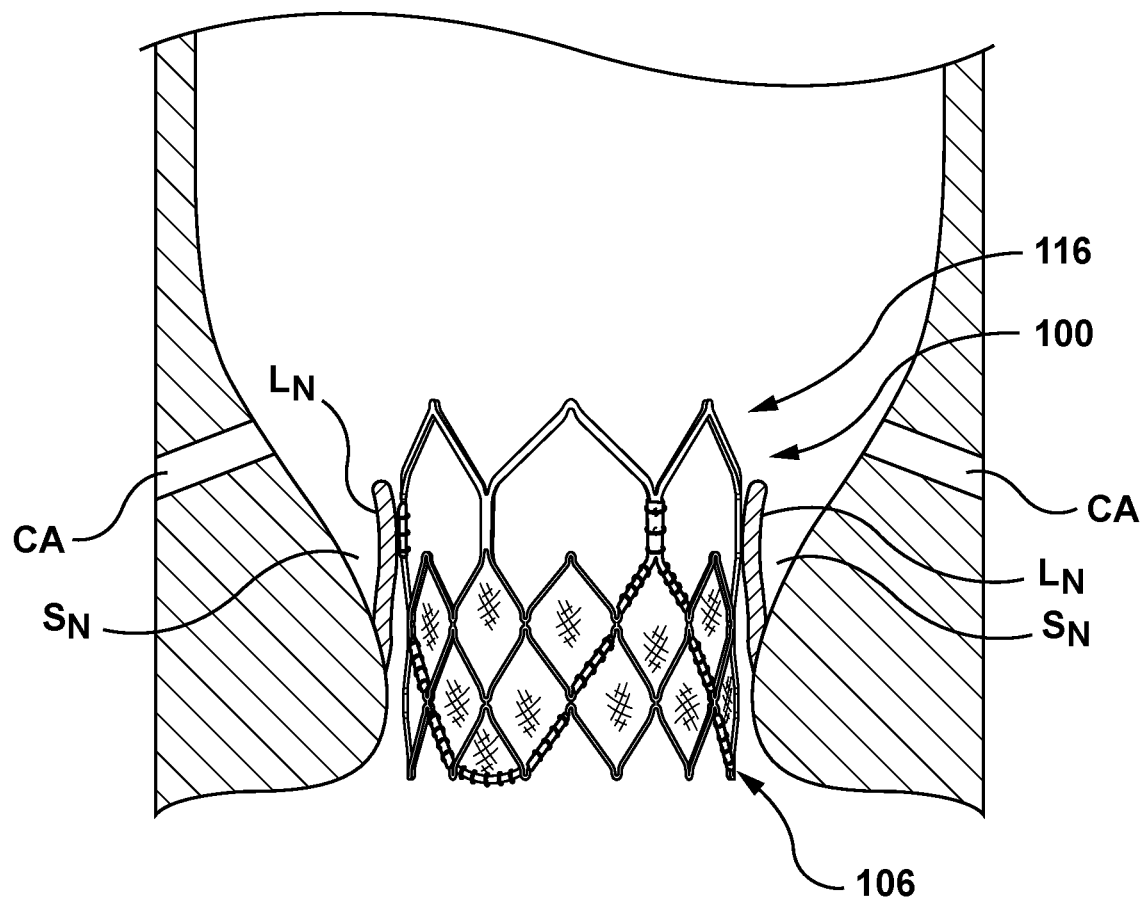
FIG. 3 is a side view illustration of the transcatheter valve prosthesis of FIG. 1 implanted within a native aortic valve annulus.

FIG. 3 illustrates the transcatheter valve prosthesis 100 implanted in situ within a native aortic valve annulus, which is shown in section, having native leaflets LN and corresponding native sinuses SN. FIG. 3 also illustrates placement of the coronary arteries CA. The transcatheter valve prosthesis 100 is configured for intra-annular placement within a native aortic valve. More particularly, the inflow end 106 of the transcatheter valve prosthesis 100 extends into and anchors within the aortic annulus of a patient's left ventricle, while the outflow end 116 of the transcatheter valve prosthesis 100 is positioned within the aortic sinuses, with no portion of the transcatheter valve prosthesis 100 extending into the patient's ascending aorta. When the transcatheter valve prosthesis 100 is deployed within the valve annulus of a native heart valve, the stent 102 is configured to be expanded within native valve leaflets LN of the patient's defective valve, to thereby retain the native valve leaflets in a permanently open state. A height or length of the stent 102 in the expanded configuration is between 12 and 24 mm, the height being measured from the most proximal part thereof (endmost inflow crowns 110A, which will be described in more detail herein) to the most distal part thereof (endmost outflow crowns 120A, which will be described in more detail herein). In an embodiment hereof, a height or length of the stent 102 in the expanded configuration is between 15 and 24 mm. For example, in an embodiment the stent 102 has diameter of between 21-24 mm and a height of 17 mm. In another embodiment, the stent 102 has diameter of between 24-27 mm and a height of 19 mm. In yet another embodiment, the stent 102 has diameter of between 27-30 mm and a height of 21 mm. In another embodiment hereof, the stent 102 may be configured for supra-annular placement.

Figure 6:
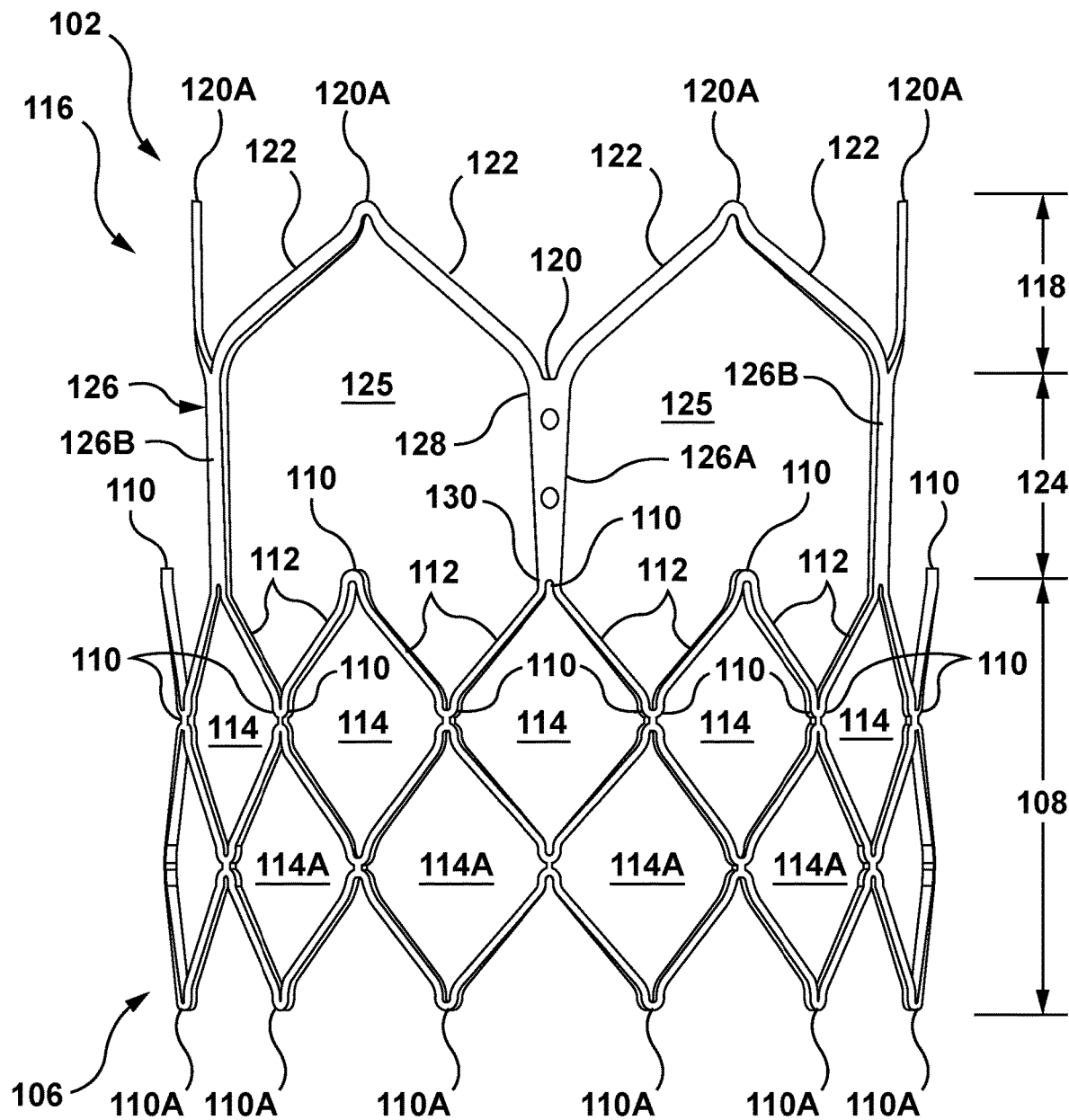
FIG. 6 is a side view of the stent of the transcatheter valve prosthesis of FIG. 1, wherein the stent is in the expanded configuration.
Figure 7:
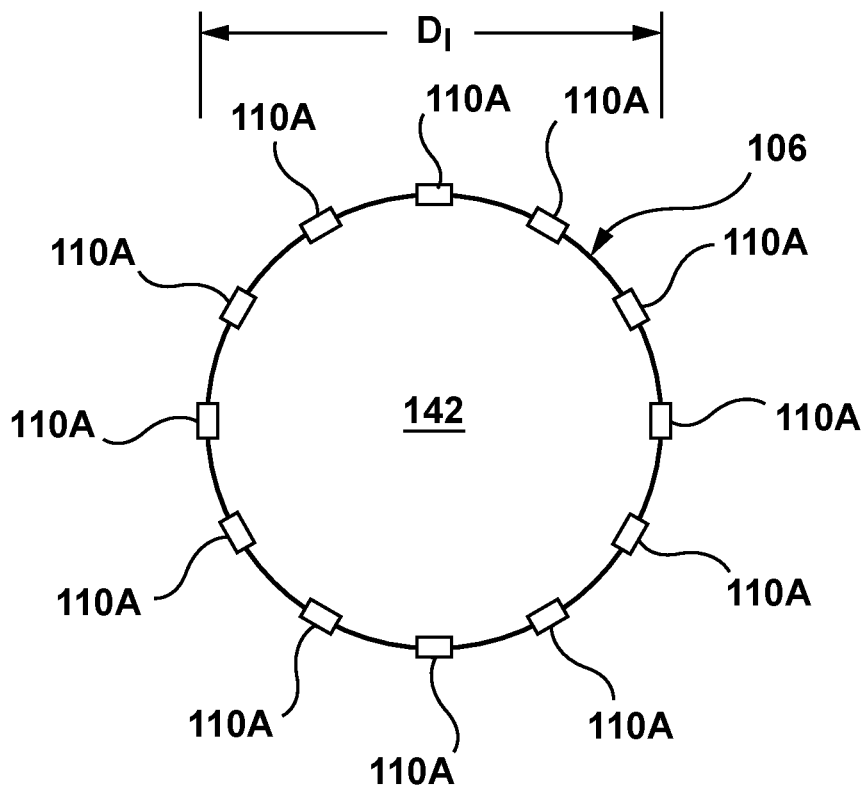
FIG. 7 is an end view of an inflow end of the stent of the transcatheter valve prosthesis of FIG. 1.
Figure 8:
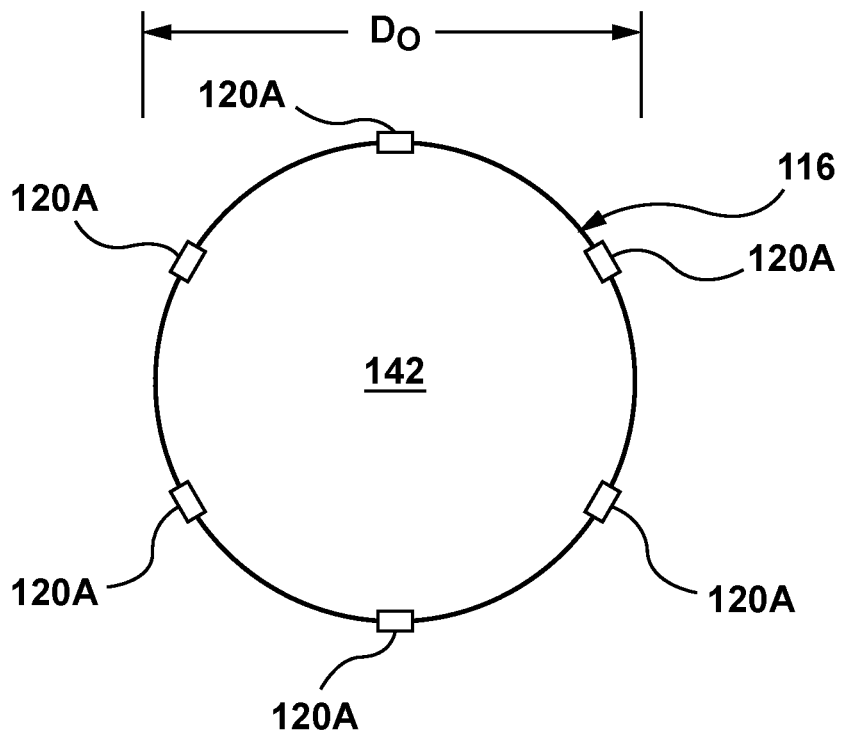
FIG. 8 is an end view of an outflow end of the stent of the transcatheter valve prosthesis of FIG. 1.

The stent 102 will now be described in more detail. The stent 102 includes an inflow portion 108, an outflow portion 118, and a transition portion 124 bridging, connecting, or otherwise extending between the inflow portion 108 and the outflow portion 118. The stent 102 is a tubular component defining a central lumen or passageway 142, and further defines the inflow or proximal end 106 and the outflow or distal end 116 of the transcatheter valve prosthesis 100. When expanded, a diameter Di of the inflow end 106 of the stent 102 is substantially the same as a diameter Do of the outflow end 116 of the stent 102. In an embodiment, the diameters Di and Do may range between 18 and 30 mm in order to accommodate dimensions of the native valve anatomy. Stated another way, it may be desirable for the transcatheter valve prosthesis 100 to be available in varying size increments to accommodate varying diameters or sizes of a patient's native annulus. The stent 102 may be formed by a laser-cut manufacturing method and/or another conventional stent forming method as would be understood by one of ordinary skill in the art. The cross-section of the stent 102 may be circular, ellipsoidal, rectangular, hexagonal, square, trapezoidal, or other polygonal shape, although at present it is believed that circular, ellipsoidal, or trapezoidal may be preferable with the transcatheter valve prosthesis 100 being provided for replacement of an aortic valve. Similarly, the cross-section of the various struts that form the stent 102 may be circular, ellipsoidal, rectangular, hexagonal, square, trapezoidal, wedge-shaped, or other polygonal shape. The stent 102 has an expanded configuration, which is shown in the perspective and side views of FIGS. 4 and 6, respectively, and a non-expanded or crimped configuration, which is shown in the side view of FIG. 5. Non-expanded or crimped configuration as used herein refers to the configuration of the stent 102 after crimping onto a balloon of a balloon catheter for delivery. FIG. 7 is an end view of the inflow end 106 of the stent 102, while FIG. 8 is an end view of the outflow end 116 of the stent 102.

Figure 6A:
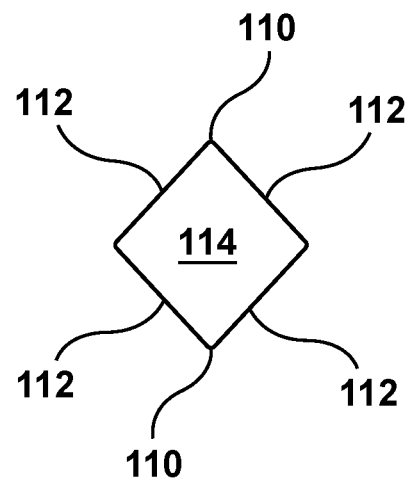
FIG. 6A is an enlarged side view of a single cell or side opening of an inflow portion of the stent of the transcatheter valve prosthesis of FIG. 1, wherein the stent is in the expanded configuration.

The inflow portion 108 is formed proximate to the inflow end 106 of the stent. The inflow portion 108 includes a plurality of crowns 110 and a plurality of struts 112 with each crown 110 being formed between a pair of opposing struts 112. Each crown 110 is a curved segment or bend extending between opposing struts 112. The inflow portion 108 is tubular, with a plurality of side openings 114 being defined by the plurality of crowns 110 and the plurality of struts 112. In an embodiment, the plurality of side openings 114 may be diamond-shaped. More particularly, as best shown in FIG. 6A which is a side view of a single side opening 114 of the inflow portion 108 of the stent 102, each side opening 114 is formed by two pairs of opposing crowns 110 and four struts 112 therebetween. Each side opening 114 is symmetrical for easier integration with the prosthetic valve 132. A series of endmost inflow side openings 114A and a series of endmost inflow crowns 110A are formed at the inflow end 106 of the stent 102. The inflow end 106 of the stent 102 has a total of twelve endmost inflow crowns 110A, as best shown in the end view of FIG. 7.

Figure 2:
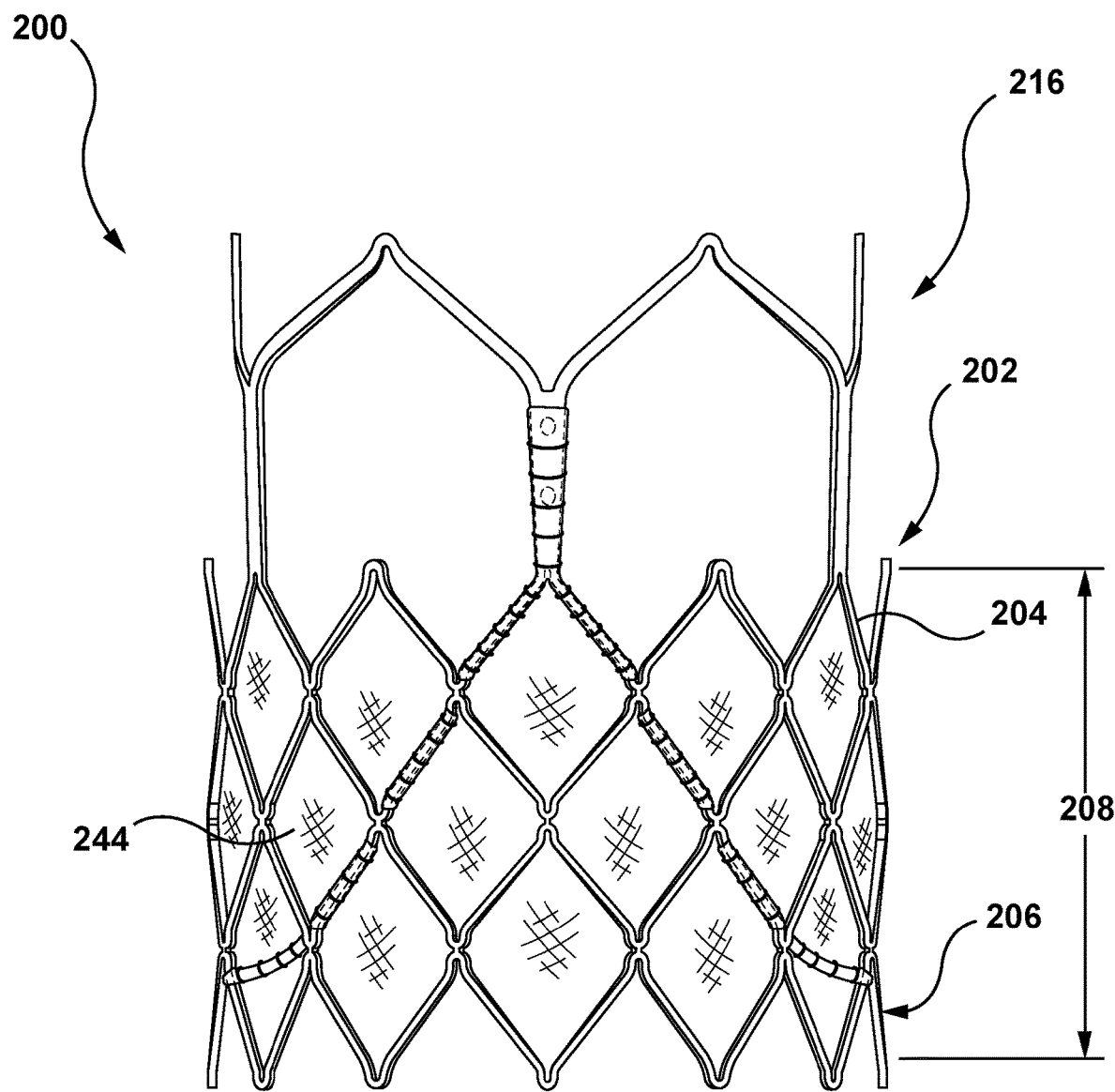
FIG. 2 is a side view of a transcatheter valve prosthesis according to another embodiment hereof, wherein the transcatheter valve prosthesis is relatively longer and shown in an expanded configuration.

The length or height of the inflow portion 108 may vary from that depicted herein in order to accommodate dimensions of the native valve anatomy. For example, in another embodiment hereof as shown in FIG. 2, a transcatheter valve prosthesis 200 is shown that is relatively longer than the transcatheter valve prosthesis 100. More particularly, the transcatheter valve prosthesis 200 includes a stent 202 having graft material 244 which encloses or lines a portion of the stent 202 as would be known to one of ordinary skill in the art of prosthetic tissue valve construction. The stent 202 is a tubular component that defines an inflow end 206 and an outflow end 216 of the transcatheter valve prosthesis 200. An inflow portion 208 of the stent 202 is relatively longer than the inflow portion 108 of the stent 102 so that the overall length or height of the transcatheter valve prosthesis 200 may be relatively increased or decreased to accommodate dimensions of the native valve anatomy. For example, a height or length of the stent 202 in the expanded configuration is between 18-24 mm.

The outflow portion 118 is formed proximate to the outflow end 116 of the stent. The outflow portion 118 includes a plurality of crowns 120 and a plurality of struts 122 with each crown 120 being formed between a pair of opposing struts 122. Each crown 120 is a curved segment or bend extending between opposing struts 122. The outflow portion 118 can be configured in a shape that forms a central lumen or passageway, for example, a ring. A series of endmost outflow crowns 120A are formed at the outflow end 116 of the stent 102. The outflow end 116 of the stent 102 has a total of six endmost outflow crowns 120A, as best shown in the end view of FIG. 8. In an embodiment hereof, the total of the endmost inflow crowns 110A are twice a total of the endmost outflow crowns 120A. In this embodiment, the endmost outflow crowns 120A are not connected to axial frame members 126 of the transition portion 124 but rather may be considered to be free or unattached while the remaining outflow crowns 120 of the outflow portion 118 are connected to the axial frame members 126 and disposed closer to the inflow end 106 than the endmost outflow crowns 120A.

The transition portion 124 bridges, connects, or otherwise extends between the inflow portion 108 and the outflow portion 118. While the stent 124 has been described as including a transition portion 124, one skilled in the art will realize that the transition portion 124 may form a portion of the inflow portion 108 and/or the outflow portion 118. The transition portion 124 includes a total of six axial frame members 126, each axial frame member 126 extending between a crown 120 of the outflow portion 118 and a crown 110 of the inflow portion 108. More particularly, each axial frame member 126 is an axial segment having a first end 128 connected to a crown 120 of the outflow portion 118 and a second end 130 connected to a crown 110 of the inflow portion 108. The axial frame members 126 are substantially parallel to the central longitudinal axis of the stent 102. Each axial frame member 126 is disposed approximately halfway between a pair of adjacent endmost outflow crowns 120A. Three of the six axial frame members 126 are commissure posts 126A and aligned with and attached to a respective commissure of the three leaflets 134 of the prosthetic valve 132. Three of the axial frame members 126 are axial struts 126B and are disposed between adjacent commissure posts 126A. The axial frame members 126 aid in valve alignment and coaptation. More particularly, the axial frame members 126 reinforce or strengthen the commissure region of the prosthetic valve 132 by shaping the leaflets 134 and supporting the leaflets 134 during opening and closing thereof, and thus provide more reliable leaflet coaptation. Symmetrical cell expansion ensures that stent 102 crimps well onto a balloon of a balloon catheter for delivery. Poor crimp quality may lead to portions of the stent overlapping when crimped, which in turn may cause tissue damage to the valve leaflets of the prosthetic valve during the crimping process.

The prosthetic valve 132 is disposed within and secured to at least the transition portion 124 of the stent 102 at the commissure posts 126. In addition, the prosthetic valve 132 may also be disposed within and secured to the inflow portion 108 of the stent 102.

Figure 6B:
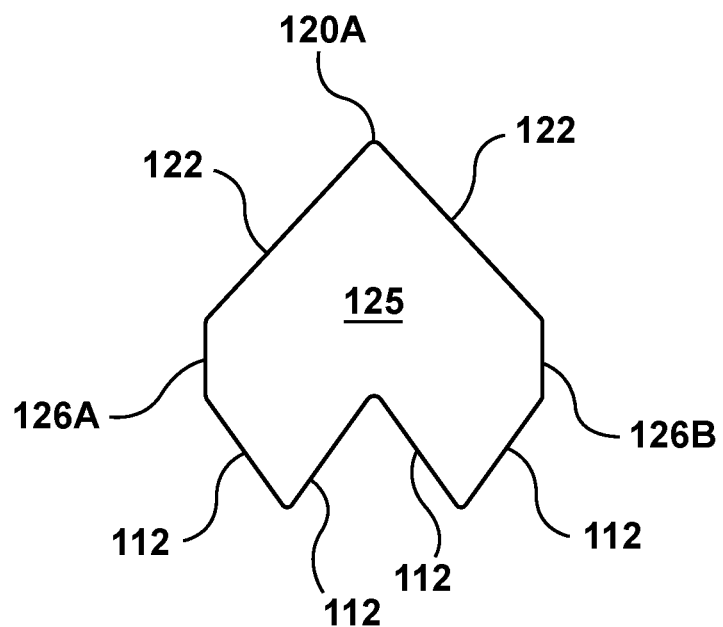
FIG. 6B is an enlarged side view of a single endmost opening of the stent of the transcatheter valve prosthesis of FIG. 1, wherein the stent is in the expanded configuration.

In the embodiment shown, there is a single row of struts 122 and crowns 120 between the first ends 128 and the outflow end 116 of the stent 102. Further, in the embodiment shown, exactly two struts 122 and a single crown 120 of the outflow portion 118 are disposed between adjacent axial frame members 126. Such an arrangement provides a series of six endmost outflow side openings or cells 125 formed at the outflow portion 118 of the stent 102. Each endmost outflow side opening or cell 125 defines an open space in the stent 102, which is formed in any type of shape, in the radially expanded configuration. In an embodiment, as best shown in FIG. 6B which is a side view of a single endmost outflow side opening 125 of the stent 102, each endmost outflow side opening 125 is defined by two adjacent struts 122 of the outflow portion 118, four adjacent struts 112 of the inflow portion 108, and two adjacent axial frame members 126 of the transition portion 124. The endmost outflow side openings 125 of the outflow portion 118 are relatively larger than the plurality of side openings 114 of the inflow portion 108 (defined by four adjacent struts 112 of the inflow portion 108) to improve access to the coronary arteries. More particularly, the endmost outflow side openings 125 of the outflow portion 118 are configured to be of sufficient size to be easily crossed with a coronary guide catheter into either the right coronary artery or the left main coronary artery once the transcatheter valve prosthesis 100 is deployed in situ. The inflow portion 108 includes exactly three rows of struts 112 and crowns 110 between the second ends 130 of the axial frame members 126 and the inflow end 106 of the stent 102. Further, four struts 112 and three crowns 110 are disposed between the second ends 130 of adjacent axial frame members 126.

Figure 30:
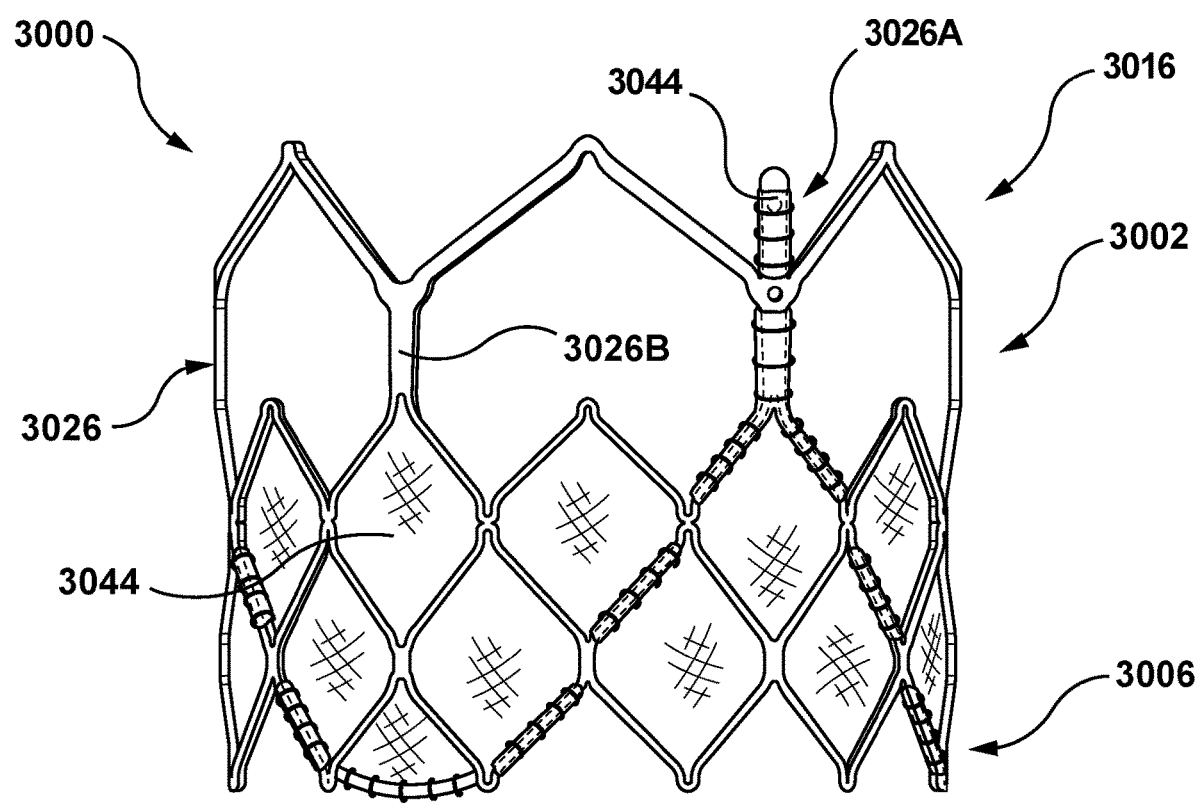
FIG. 30 is a side view of a transcatheter valve prosthesis according to another embodiment hereof, wherein the transcatheter valve prosthesis is in an expanded or deployed configuration and a stent thereof includes a lengthened commissure post.
Figure 36:
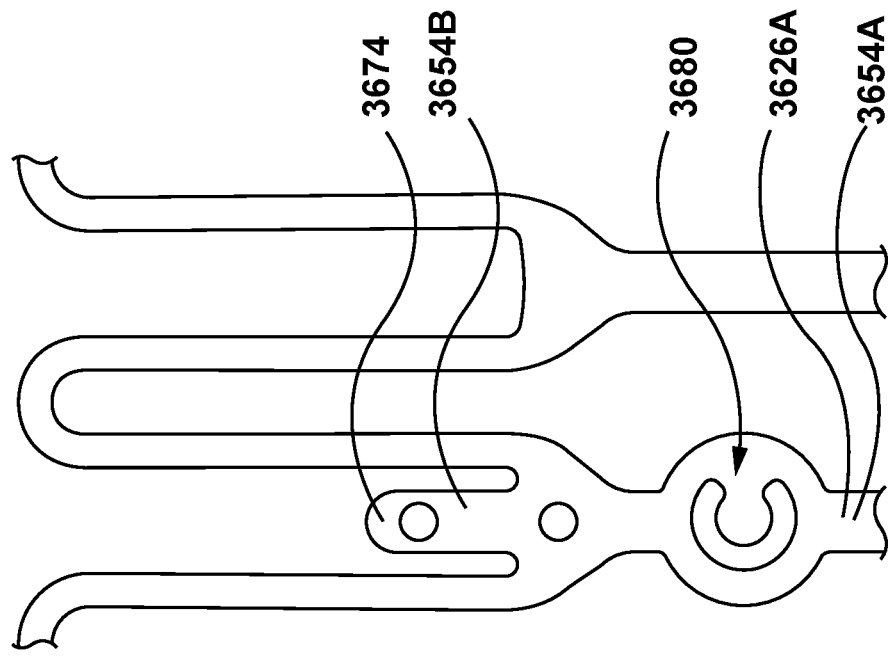
FIG. 36 is an enlarged side view of a portion of a lengthened commissure post according to another embodiment hereof, wherein the lengthened commissure post includes a directional marker and the directional marker is a C-shaped element.

In another embodiment hereof (not shown), the stent 102 may be formed with lengthened commissure posts having an outflow portion that extends into the outflow portion of the stent as described with respect to FIGS. 30, 31, and 32. Further, the stent 102 may further include directional markers as described with respect to FIGS. 33-37 and/or inflow markers and outflow markers as described with respect to FIGS. 38A-41D.

Figure 9:
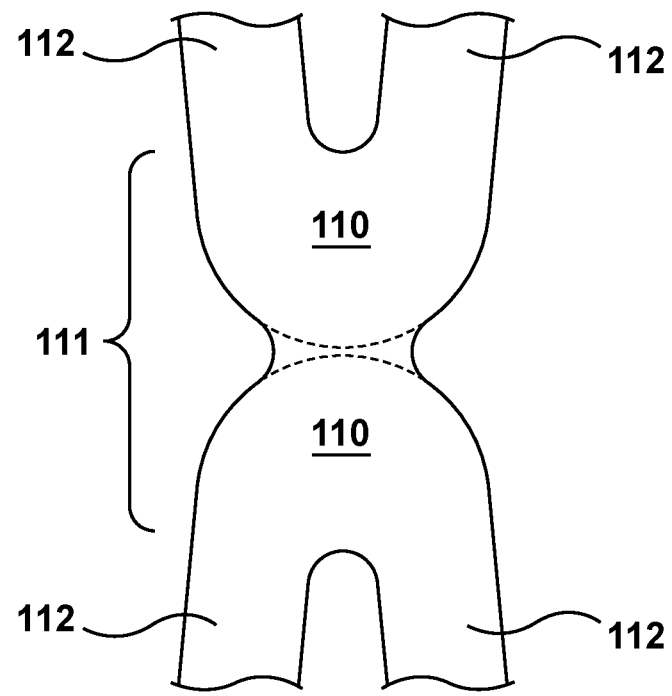
FIG. 9 is an enlarged side view of a node of an inflow portion of the stent of the transcatheter valve prosthesis of FIG. 1.
Figure 10:
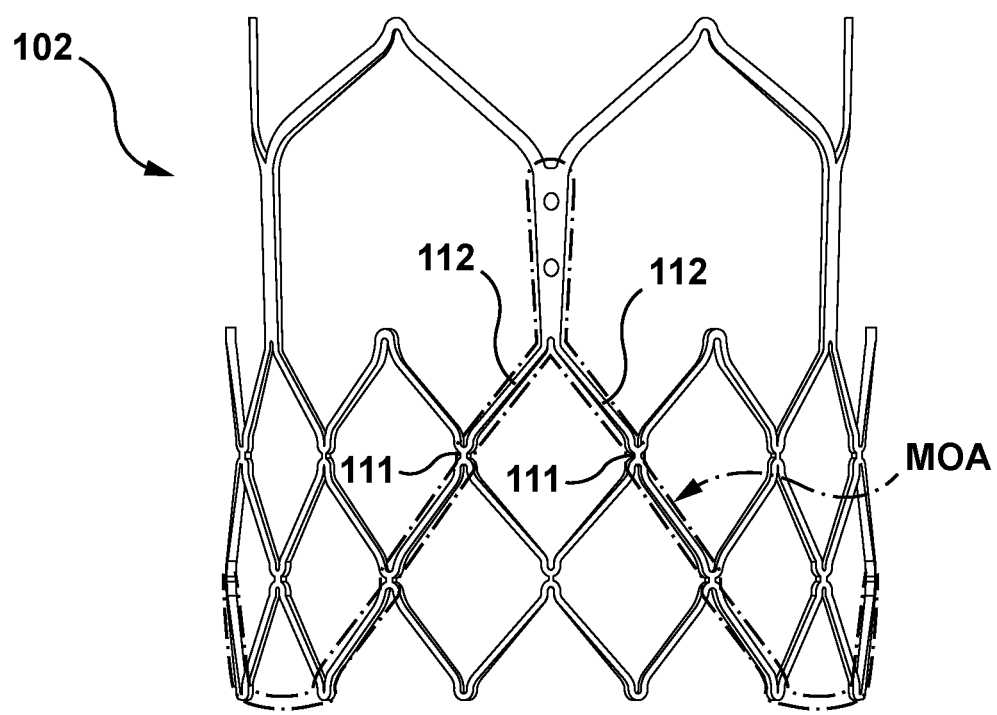
FIG. 10 is a side view of the stent including the nodes of FIG. 9, wherein the stent is in the expanded configuration and a margin of attachment is shown thereon for illustrative purposes only.

The three leaflets 134 of the prosthetic valve 132 are attached to the stent 102 along a margin of attachment that follows struts 112 and nodes 111 of the inflow portion 108 of the stent 102. With the margin of attachment following the stent structure, the prosthetic valve 132 is more fully secured to the stent 102 and minimizes suture or tissue tearing from the stent 102 during operation. With reference to FIGS. 9 and 10, a node 111 is defined as a region where two crowns of the plurality of crowns 110 within the inflow portion 108 connect. In the embodiment of FIG. 9, which is an enlarged side view of a node 111 within the inflow portion 108 of the stent 102, two crowns 110 abut against each other without any overlap of the bends thereof. The bends of the two crowns 110 are shown in phantom for illustrative purposes only. FIG. 10 is a side view of the stent 102 including the nodes 111 of FIG. 9, and a margin of attachment MOA is shown thereon for illustrative purposes only. As shown in FIG. 10, the margin of attachment MOA follows the struts 112 as well as the nodes 111. The margin of attachment MOA extends vertically along the nodes 111 and is angled along the struts 112. Thus, in this embodiment, the margin of attachment MOA has a generally concave shape but includes a plurality of vertical steps along the nodes 111 of the stent 102.

Figure 11:
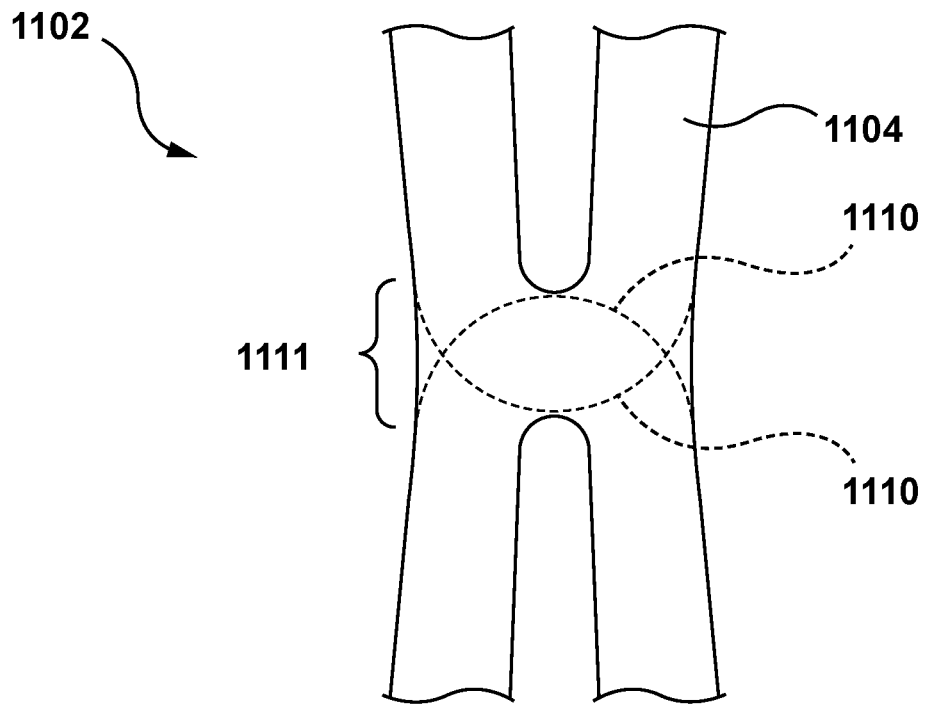
FIG. 11 is an enlarged side view of a node according to another embodiment hereof.
Figure 12:
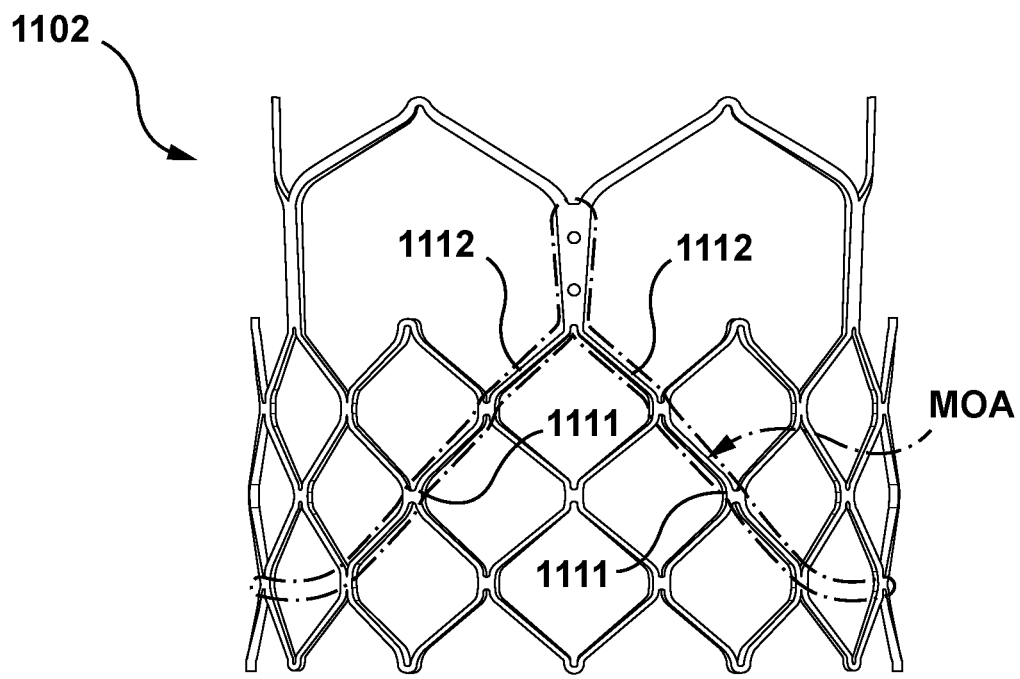
FIG. 12 is a side view of a stent including the nodes of FIG. 11, wherein the stent is in the expanded configuration and a margin of attachment is shown thereon for illustrative purposes only.

In another embodiment shown in FIGS. 11 and 12, a stent 1102 includes a different node configuration that results in a margin of attachment MOA that has a smooth concave shape without the vertical steps described above. More particularly, FIG. 11 is an enlarged side view of a node 1111 according to another embodiment hereof. FIG. 12 is a side view of a stent 1102 including the nodes 1111 of FIG. 11, and a margin of attachment MOA is shown thereon for illustrative purposes only. In the embodiment of FIGS. 11 and 12, two crowns 1110 "overlap" each other such that the nodes 1111 have a relatively reduced height. The bends of the two crowns 1110 are shown in phantom for illustrative purposes only. The node 1111 in which the two crowns 110 overlap each other is relatively shorter or has a relatively reduced height compared to the node 111 in which the two crowns 110 abut against each other. The two crowns 1110 of the node 1111 do not overlap in terms of thickness or layers but rather overlap in terms of geometry. More particularly, the two crowns 1110 overlap in the sense that the bends of the two crowns 1110 overlay or are superimposed over each other. However, in an embodiment, the node 1111 has the same thickness as a single crown 1110. In another embodiment, the thickness of the node 1111 is slightly greater than the width of a single crown 1110, such as 1.15 greater than the thickness of a single crown 1110. These node configurations results in a smoother margin of attachment. As shown in FIG. 12, the margin of attachment MOA follows the struts 1112 as well as the nodes 1111. The margin of attachment MOA curves or is angled along the nodes 1111 and curves or is angled along the struts 1112. Thus, in this embodiment, the margin of attachment MOA has a smooth concave shape that does not include a plurality of vertical steps as described above with respect to FIGS. 9 and 10. The smooth concave shape of the margin of attachment MOA maximizes valve performance, because such valve attachment improves leaflet durability and hemodynamics of the prosthetic valve (not shown). As will be understood by one of ordinary skill in the art, FIG. 12 illustrates the stent 1102 having a relatively longer inflow portion similar to the inflow portion 208 described above with respect to FIG. 2, but nodes 1111 may be utilized on any inflow portion and any stent described herein.

Figure 13:
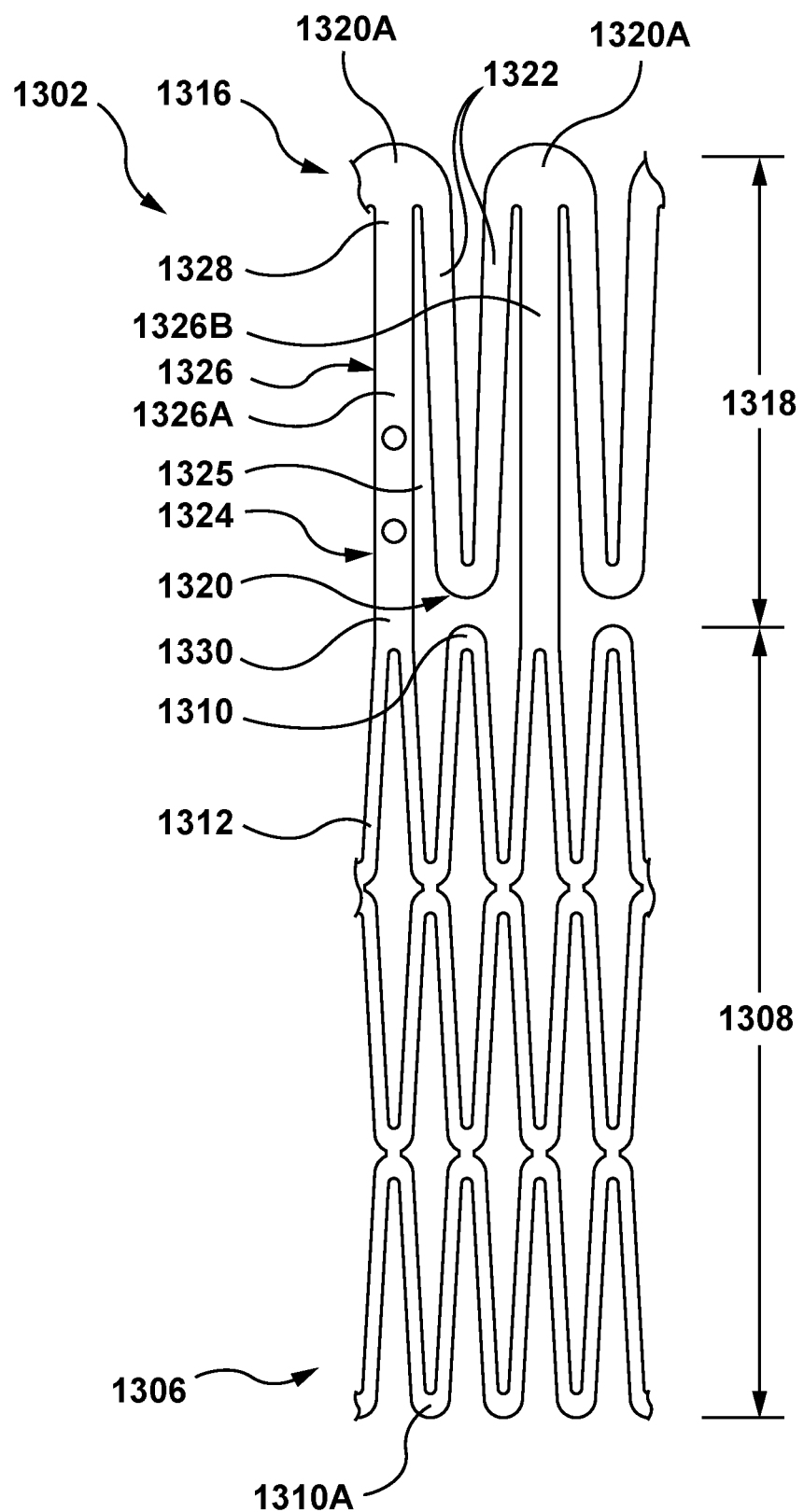
FIG. 13 is a side view of a stent according to another embodiment hereof, wherein the stent is in a non-expanded or crimped configuration and crowns of an outflow portion of the stent are inverted.

FIG. 13 is a side view of a stent 1302 according to another embodiment hereof. In FIG. 13, the stent 1302 is in a non-expanded or crimped configuration. The stent 1302 is similar to the stent 102 except that the crowns 1320 of an outflow portion 1318 of the stent 1302 are inverted as compared to the crowns 120 of the outflow portion 118 of the stent 102. More particularly, the stent 1302 is balloon-expandable and includes an inflow portion 1308, an outflow portion 1318, and a transition portion 1324 bridging, connecting, or otherwise extending between the inflow portion 1308 and the outflow portion 1318. The stent 1302 is a tubular component defining a central lumen or passageway (not shown on FIG. 13) and having an inflow or proximal end 1306 and an outflow or distal end 1316. When expanded, a diameter of the inflow end 1306 of the stent 1302 is the same as a diameter of the outflow end 1316 of the stent 1302. The stent 1302 may be formed by a laser-cut manufacturing method and/or another conventional stent forming method as would be understood by one of ordinary skill in the art. The cross-section of the stent 1302 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 1302 may be circular, ellipsoidal, rectangular, hexagonal, square, trapezoidal, wedge-shaped, or other polygonal shape. Although FIG. 13 illustrates the stent 1302 in its non-expanded or crimped configuration, it will be understood by one of ordinary skill in the art that the stent 1302 has an expanded configuration.

A prosthetic valve (not shown) is disposed within and secured to at least the transition portion 1324 of the stent 1302. In addition, the prosthetic valve may also be disposed within and secured to the inflow portion 1308 of the stent 1302. The prosthetic valve is the same as prosthetic valve 132 described above. The inflow portion 1308 is formed proximate to the inflow end 1306 of the stent 1302, and is the same as inflow portion 108 described above. The inflow portion 1308 of the stent 1302 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1306 of the stent 1302 has a total of twelve endmost inflow crowns 1310A.

The outflow portion 1318 is formed proximate to the outflow end 1316 of the stent 1302. The outflow portion 1318 includes a plurality of crowns 1320 and a plurality of struts 1322 with each crown 1320 being formed between a pair of opposing struts 1322. Each crown 1320 is a curved segment or bend extending between opposing struts 1322. The outflow portion 1318 can be configured in a shape that forms a central lumen or passageway, for example, a ring. A series of endmost outflow crowns 1320A are formed at the outflow end 1316 of the stent 1302. Similar to the stent 102, the outflow end 1316 of the stent 1302 has a total of six endmost outflow crowns 1320A. In an embodiment hereof, the total of the endmost inflow crowns 1310A are twice a total of the endmost outflow crowns 1320A.

The transition portion 1324 bridges, connects, or otherwise extends between the inflow portion 1308 and the outflow portion 1318. While the stent 1324 has been described as including a transition portion 1324, one skilled in the art will realize that the transition portion 1324 may form a portion of the inflow portion 1308 and/or the outflow portion 1318. The transition portion 1324 includes a total of six axial frame members 1326, each axial frame member 1326 extending between an endmost outflow crown 1320A of the outflow portion 1318 and a crown 1310 of the inflow portion 1308. More particularly, each axial frame member 1326 is an axial segment having a first end 1328 connected to an endmost outflow crown 1320A of the outflow portion 1318 and a second end 1330 connected to a crown 1310 of the inflow portion 1308. Each axial frame member 1326 is aligned with an endmost outflow crown 1320A. Three of the six axial frame members 1326 are commissure posts 1326A and are aligned with and attached to respective commissures of the three leaflets of the prosthetic valve. Three of the axial frame members 1326 are axial struts 1326B disposed between two of the commissure posts 1326A. The axial frame members 1326 aid in valve alignment and coaptation. More particularly, the axial frame members 1326 reinforce or strengthen the commissure region of the prosthetic valve 1332 by shaping the leaflets and supporting the leaflets during opening and closing thereof, and thus provide more reliable leaflet coaptation.

In the embodiment shown, there is a single row of struts 1322 and crowns 1320 coupled to the first ends 1328 of the axial frame members 1326 and defining the outflow end 1316 of the stent 1302. Further, in the embodiment shown, exactly two struts 1322 and a single crown 1320 of the outflow portion 1318 are disposed between adjacent axial frame members 126. Such an arrangement provides a series of six endmost outflow side openings 1325 formed at the outflow portion 1318 of the stent 1302. Each of the endmost outflow side opening 1325 is defined by two adjacent struts 1322 of the outflow portion 1318, four adjacent struts 1312 of the inflow portion 1308, and two adjacent axial frame members 1326 of the transition portion 1324.

In this embodiment, the endmost outflow crowns 1320A of the outflow portion 1318 are connected to the axial frame members 1326 while the free or unattached crowns 1320 of the outflow portion 1318 are disposed closer to the inflow end 1306 than the endmost outflow crowns 1320A. This configuration allows the length of the axial frame members 1326 to be increased relative to the axial frame members 126 of the stent 102 to maximize space for valve attachment.

As with the stent 102, the inflow portion 1308 includes exactly three rows of struts 1312 and crowns 1310 between the second ends 1330 of the axial frame members 1326 and the inflow end 1306 of the stent 1302. Further, four struts 1312 and three crowns 1310 are disposed between the second ends 1330 of adjacent axial frame members 1326. Further, the stent 1302 may further include directional markers as described with respect to FIGS. 33-37 and/or inflow markers and outflow markers as described with respect to FIGS. 38A-41D.

Figure 14:
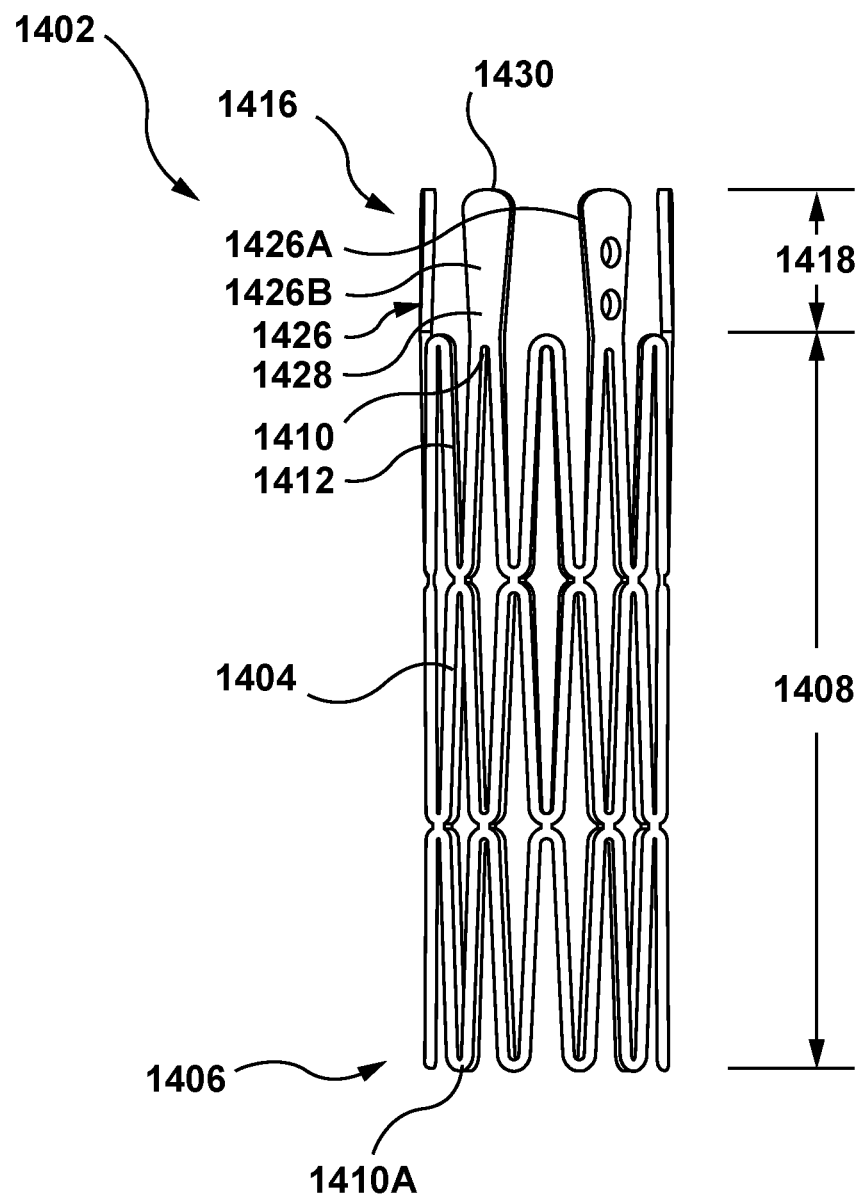
FIG. 14 is a side view of a stent according to another embodiment hereof, wherein the stent is in an expanded configuration and an outflow portion of the stent does not include crowns.

FIG. 14 is a side view of a stent 1402 according to another embodiment hereof. In FIG. 14, the stent 1402 is in a non-expanded or crimped configuration. An outflow portion 1418 of a stent 1402 does not include crowns. More particularly, the stent 1402 is balloon-expandable and includes an inflow portion 1408 and the outflow portion 1418. The stent 1402 is a tubular component defining a central lumen or passageway (not shown on FIG. 14) and having an inflow or proximal end 1406 and an outflow or distal end 1416. When expanded, a diameter of the inflow end 1406 of the stent 1402 is the same as a diameter of the outflow end 1416 of the stent 1402. The stent 1402 may be formed by a laser-cut manufacturing method and/or another conventional stent forming method as would be understood by one of ordinary skill in the art. The cross-section of the stent 1402 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 1402 may be circular, ellipsoidal, rectangular, hexagonal, square, trapezoidal, wedge-shaped, or other polygonal shape. Although FIG. 14 illustrates the stent 1402 in its non-expanded or crimped configuration, it will be understood by one of ordinary skill in the art that the stent 1402 has an expanded configuration.

A prosthetic valve (not shown) is disposed within and secured to at least the outflow portion 1418 of the stent 1402. In addition, the prosthetic valve may also be disposed within and secured to the inflow portion 1408 of the stent 1402. The prosthetic valve is the same as prosthetic valve 132 described above. The inflow portion 1408 is formed proximate to the inflow end 1406 of the stent 1402, and is the same as inflow portion 108 described above. The inflow portion 1408 of the stent 1402 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1406 of the stent 1402 has a total of twelve endmost inflow crowns 1410A.

The outflow portion 1418 is formed proximate to the outflow end 1416 of the stent 1402. The outflow portion 1418 includes a minimum of three axial frame members 1426. In an embodiment, the outflow portion 1418 includes up to six axial frame members 1426, with three of the axial frame members 1426 being commissure posts 1426A. Each axial frame members 1426 longitudinally extends from a crown 1410 of the inflow portion 1408. More particularly, each axial frame members 1426 is a relatively stiff, axial segment having a first end 1428 connected to a crown 1410 of the inflow portion 1408 and an unattached or free second end 1430. Three of the axial frame members 1426 are commissure posts 1426A circumferentially spaced apart and aligned with and attached to a respective commissure of the three leaflets of the prosthetic valve, with three axial struts 1426B disposed between adjacent commissure posts 1426A. The axial frame members 1426 aid in valve alignment and coaptation. More particularly, the axial frame members 1426 reinforce or strengthen the commissure region of the prosthetic valve 1442 by shaping the leaflets and supporting the leaflets during opening and closing thereof, and thus provide more reliable leaflet coaptation. In addition, the axial frame members 1426 reduce the overall height of the transcatheter valve prosthesis and maximize coronary access.

As with the stent 102, the inflow portion 1408 includes exactly three rows of struts 1412 and crowns 1410 between the first ends 1428 of the axial frame members 1426 and the inflow end 1406 of the stent 1402. Further, four struts 1412 and three crowns 1410 are disposed between the first ends 1428 of adjacent axial frame members 1426. Further, the stent 1402 may further include directional markers as described with respect to FIGS. 33-37 and/or inflow markers and outflow markers as described with respect to FIGS. 38A-41D.

The "no outflow crown" configuration of the stent 1402 maximizes access to the coronary arteries because the axial frame members 1426 are the only structures in the vicinity of the coronary arteries. It is very improbable that the right coronary artery and/or the left main coronary artery will be blocked or jailed by the axial frame members 1426, and thus there will be clear access to the coronary arteries via a coronary guide catheter once the transcatheter valve prosthesis is deployed in situ. Further, the chance of blockage can be further reduced by only including three commissure posts 1426A of the axial frame members 1426, and no axial struts 1426B. In addition, with the elimination of the outflow crowns, the overall height of the stent 1402 may be reduced relative to the overall height of the stent 102. A shorter overall height minimizes interaction with aortic anatomy and improves deliverability, thereby resulting in less vessel trauma or valve deformation.

Figure 15:
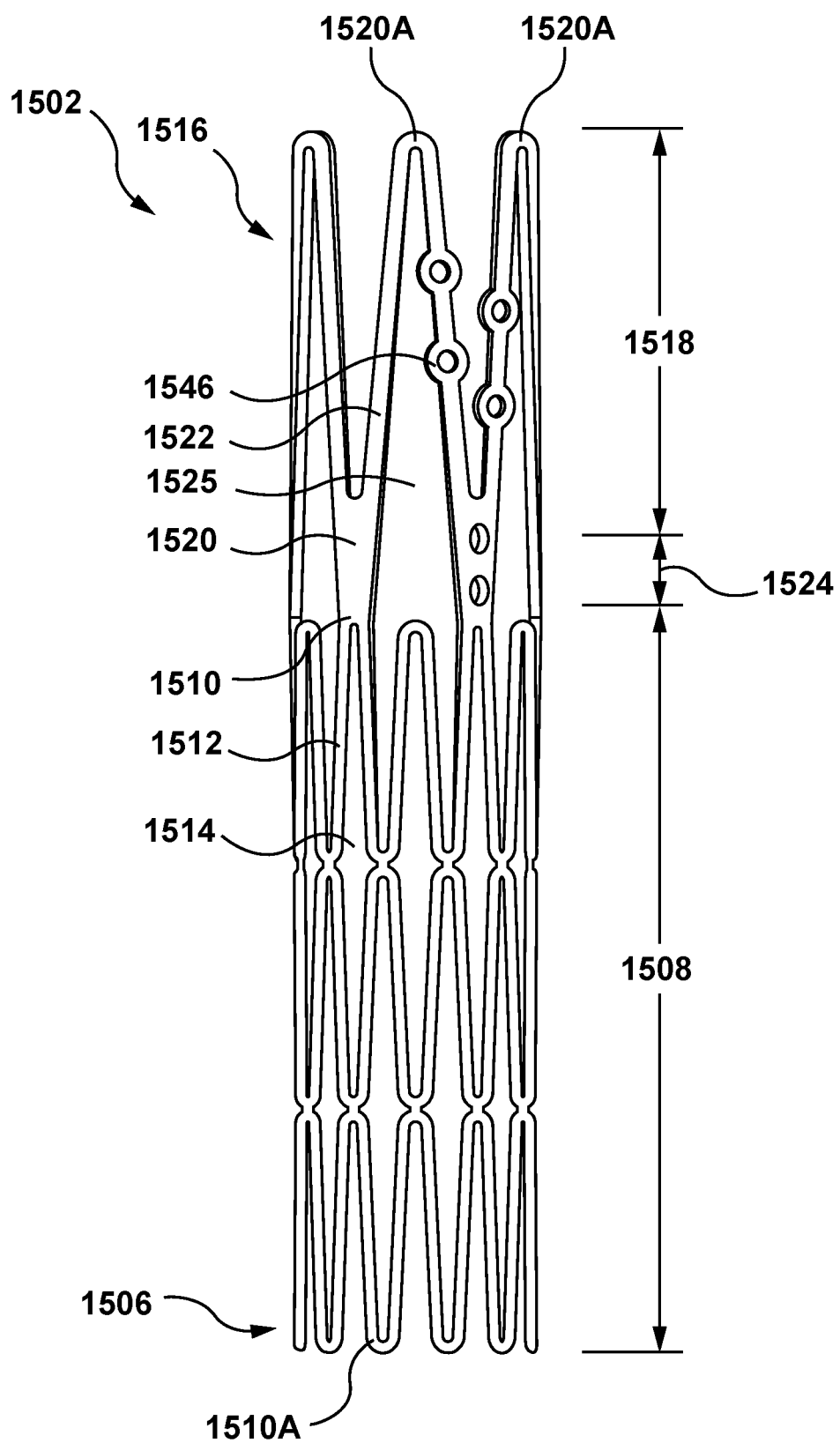
FIG. 15 is a side view of a stent according to another embodiment hereof, wherein the stent is in a non-expanded or crimped configuration and struts of an outflow portion of the stent include holes for attachment to commissures of a prosthetic valve.
Figure 16:
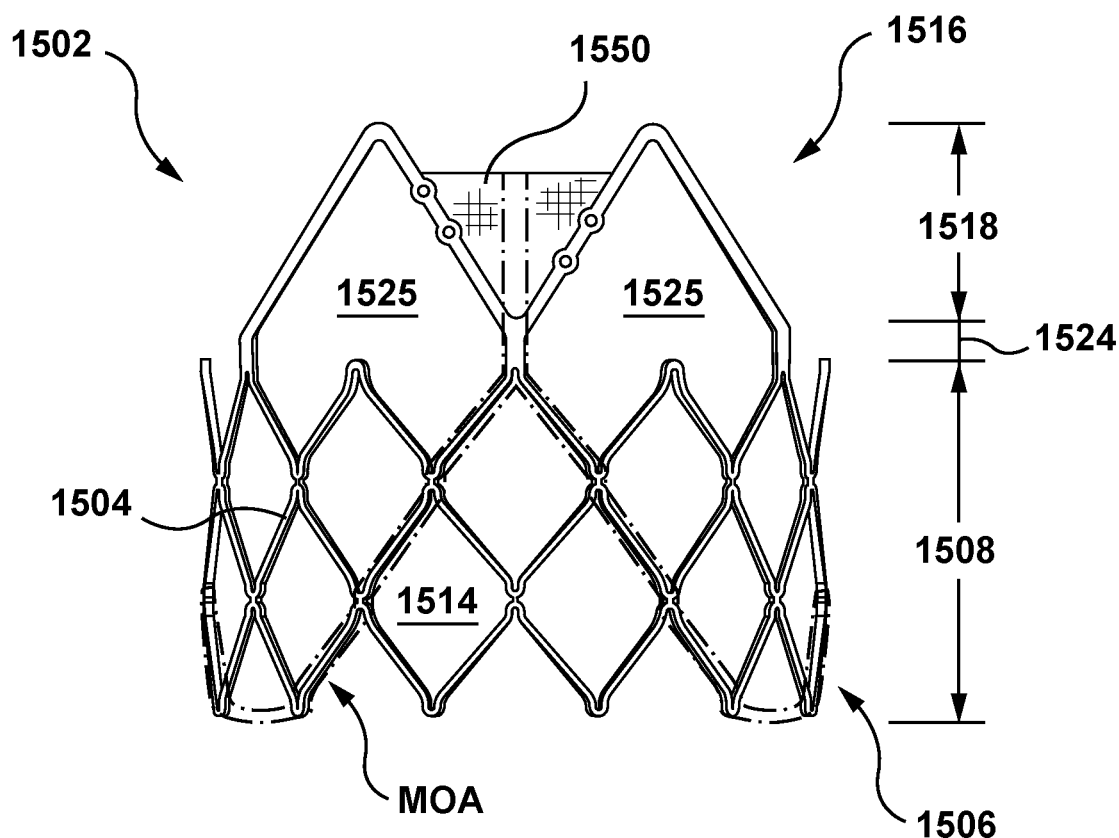
FIG. 16 is a side view of the stent of FIG. 15, wherein the stent is in an expanded configuration.
Figure 17:
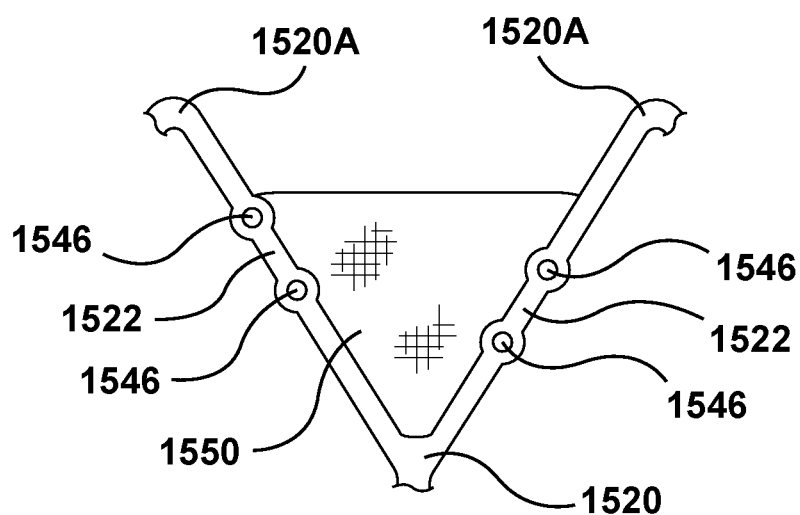
FIG. 17 is an enlarged side view of the stent of FIG. 15, wherein a flap of tissue spans between the struts of the outflow portion of the stent for attachment to commissures of a prosthetic valve.

FIGS. 15, 16, and 17 illustrate a stent 1502 according to another embodiment hereof in which commissure posts are omitted and rather a plurality of material flaps are utilized for attachment to commissures of the prosthetic valve. FIG. 15 is a side view of the stent 1502 in a non-expanded or crimped configuration, while FIG. 16 is a side view of the stent 1502 in an expanded configuration. FIG. 17 is an enlarged side view of the stent 1502 of FIG. 15, and illustrates a material flap 1550 which spans between struts 1522 of the outflow portion 1518 of the stent 1502 for attachment to commissures of a prosthetic valve.

More particularly, the stent 1502 is balloon expandable and includes an inflow portion 1508, an outflow portion 1518, and a transition portion 1524 bridging, connecting, or otherwise extending between the inflow portion 1508 and the outflow portion 1518. The stent 1502 is a tubular component defining a central lumen or passageway (not shown on FIG. 15) and having an inflow or proximal end 1506 and an outflow or distal end 1516. When expanded, a diameter Di of the inflow end 1506 of the stent 1502 is the same as a diameter Do of the outflow end 1516 of the stent 1502. The stent 1502 may be formed by a laser-cut manufacturing method and/or another conventional stent forming method as would be understood by one of ordinary skill in the art. The cross-section of the stent 1502 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 1502 may be circular, ellipsoidal, rectangular, hexagonal, square, trapezoidal, wedge-shaped, or other polygonal shape.

A prosthetic valve (not shown) is disposed within and secured to at least the outflow portion 1518 of the stent 1502. In addition, the prosthetic valve may also be disposed within and secured to the inflow portion 1508 of the stent 1502. The prosthetic valve is the same as prosthetic valve 132 described above. A margin of attachment MOA is shown in phantom on FIG. 16 and illustrates the placement of the prosthetic valve within the stent 1502. The inflow portion 1508 is formed proximate to the inflow end 1506 of the stent 1502, and is the same as inflow portion 108 described above. The inflow portion 1508 of the stent 1502 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1506 of the stent 1502 has a total of twelve endmost inflow crowns 1510A.

The outflow portion 1518 is formed proximate to the outflow end 1516 of the stent 1502. The outflow portion 1518 can be configured in a shape that forms a central lumen or passageway, for example, a ring. The outflow portion 1518 includes a plurality of crowns 1520 and a plurality of struts 1522 with each crown 1520 being formed between a pair of opposing struts 1522. Each crown 1520 is a curved segment or bend extending between opposing struts 1522. A series of endmost outflow crowns 1520A are formed at the outflow end 1516 of the stent 1502. Similar to the stent 102, the outflow end 1516 of the stent 1502 has a total of six endmost outflow crowns 1520A. In an embodiment hereof, the total of the endmost inflow crowns 1510A are twice a total of the endmost outflow crowns 1520A. In this embodiment, three pairs of adjacent struts 1522 of the outflow portion 1518 include holes 1546 formed therein. The holes 1546 are utilized in suturing the prosthetic valve into the stent 1502, as will be described in more detail herein with respect to FIG. 17.

The transition portion 1524 bridges, connects, or otherwise extends between the inflow portion 1508 and the outflow portion 1518. While the stent 1524 has been described as including a transition portion 1524, one skilled in the art will realize that the transition portion 1524 may form a portion of the inflow portion 1508 and/or the outflow portion 1518. The transition portion 1524 includes a total of six reinforced connections 1548, each reinforced connection 1548 extending between an outflow crown 1520 of the outflow portion 1518 and a crown 1510 of the inflow portion 1508. Each reinforced connection 1548 includes extra or added material that surrounds the abutting or opposing crowns 1520, 1510 such that each reinforced connection 1548 has an increased width relative to a width of the plurality of struts 1522 of the outflow portion 1518. In this embodiment, the endmost outflow crowns 1520A are not connected to the reinforced connections 1548 but rather may be considered to be free or unattached while the remaining outflow crowns 1520 of the outflow portion 1518 are connected to the reinforced connections 1548 and disposed closer to the inflow end 1506 than the endmost outflow crowns 1520A.

In the embodiment shown, there is a single row of struts 1522 and crowns 1520 coupled to the reinforced connections 1548 and defining the outflow end 1516 of the stent 1502. Further, in the embodiment shown, exactly two struts 1522 and a single crown 1520 of the outflow portion 1518 are disposed between adjacent reinforced connections 1548. Such an arrangement provides a series of six endmost outflow side openings or cells 1525 formed at the outflow portion 1518 of the stent 1502. Each endmost outflow side opening or cell 1525 defines an open space in the stent 102, which is formed in any type of shape, in the radially expanded configuration. In an embodiment, each endmost outflow side opening 1525 is defined by two adjacent struts 1522 of the outflow portion 1518, four adjacent struts 1512 of the inflow portion 1508, and two adjacent reinforced connections 1548 of the transition portion 1524. The endmost outflow side openings 1525 of the outflow portion 1518 are relatively larger than a plurality of side openings 1514 of the inflow portion 1508 to improve access to the coronary arteries. More particularly, the endmost outflow side openings 1525 of the outflow portion 1518 are configured to be of sufficient size to be easily crossed with a coronary guide catheter into either the right coronary artery or the left main coronary artery once the transcatheter valve prosthesis is deployed in situ.

As described above, three pairs of adjacent struts 1522 include holes 1546 formed therein. As shown on FIG. 17, a material flap 1550 is attached to the holes 1546 such that the material flap 1550 spans or bridges between the adjacent struts 1522 of the outflow portion 1518. Stent 1502 includes a total of three material flaps 1550 attached thereto. The three material flaps 1550 are aligned with and attached to a respective commissure of the three leaflets of the prosthetic valve. In an embodiment, each material flap 1550 is generally triangular in shape. The material flap 1550 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 1550 forms a webbing or pad to which a respective commissure of the three leaflets of the prosthetic valve is attached. The margin of attachment MOA is shown in phantom on FIG. 16 and illustrates the placement of the commissures on material flaps 1550. Since the three material flaps 1550 are aligned with and attached to a respective commissure of the three leaflets of the prosthetic valve, the material flaps 1550 aid in valve alignment and coaptation. Further, in an embodiment, each material flap 1550 may function like a trampoline and be a stress relief at the commissure during diastole. By functioning as a stress relief, the material flaps 1550 prevent commissure tissue damage, reduce intra-annular leakage, and increase the durability of the prosthetic valve.

As with the stent 102, the inflow portion 1508 includes exactly three rows of struts 1512 and crowns 1510 between the reinforced connections 1548 and the inflow end 1506 of the stent 1502. Further, four struts 1512 and three crowns 1510 are disposed between adjacent reinforced connections 1548. Further, the stent 1502 may further include directional markers as described with respect to FIGS. 33-37 and/or inflow markers and outflow markers as described with respect to FIGS. 38A-41D.

The overall height of the stent 1502 may be reduced relative to the overall height of stent 102 because the mechanism for commissure attachments reside or are integrated into the outflow portion 1518 of the stent 1502. A shorter overall height of the transcatheter valve prosthesis minimizes interaction with aortic anatomy, thereby resulting in less vessel trauma or valve deformation. A shorter overall height also improves coronary access, via a coronary guide catheter, to the right coronary artery and left main coronary artery. A shorter overall height (in the crimped state) also improves system deliverability.

Figure 18:
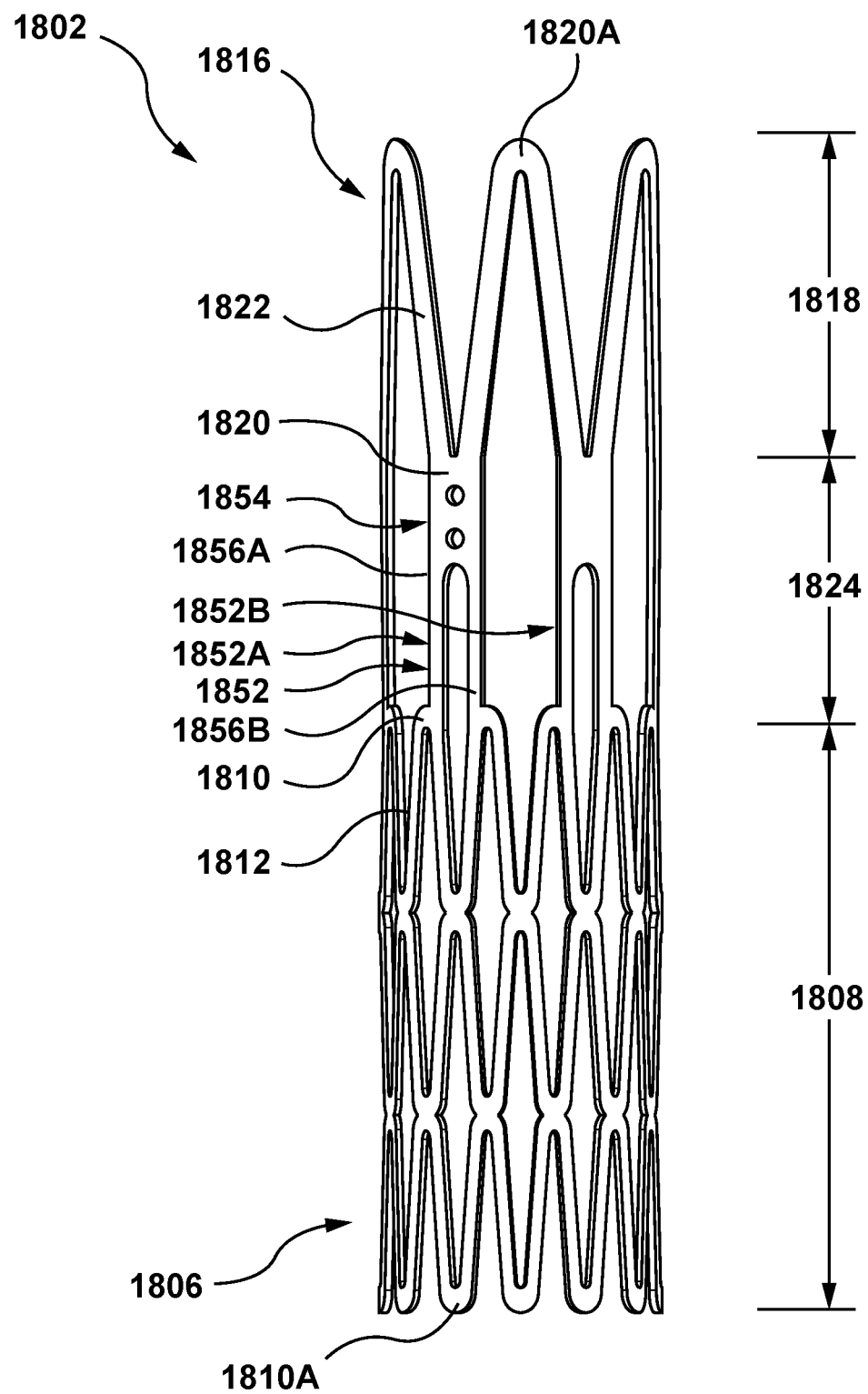
FIG. 18 is a side view of a stent according to another embodiment hereof, wherein the stent is in a non-expanded or crimped configuration and a transition portion of the stent is configured for attachment to commissures of a prosthetic valve.
Figure 19A:
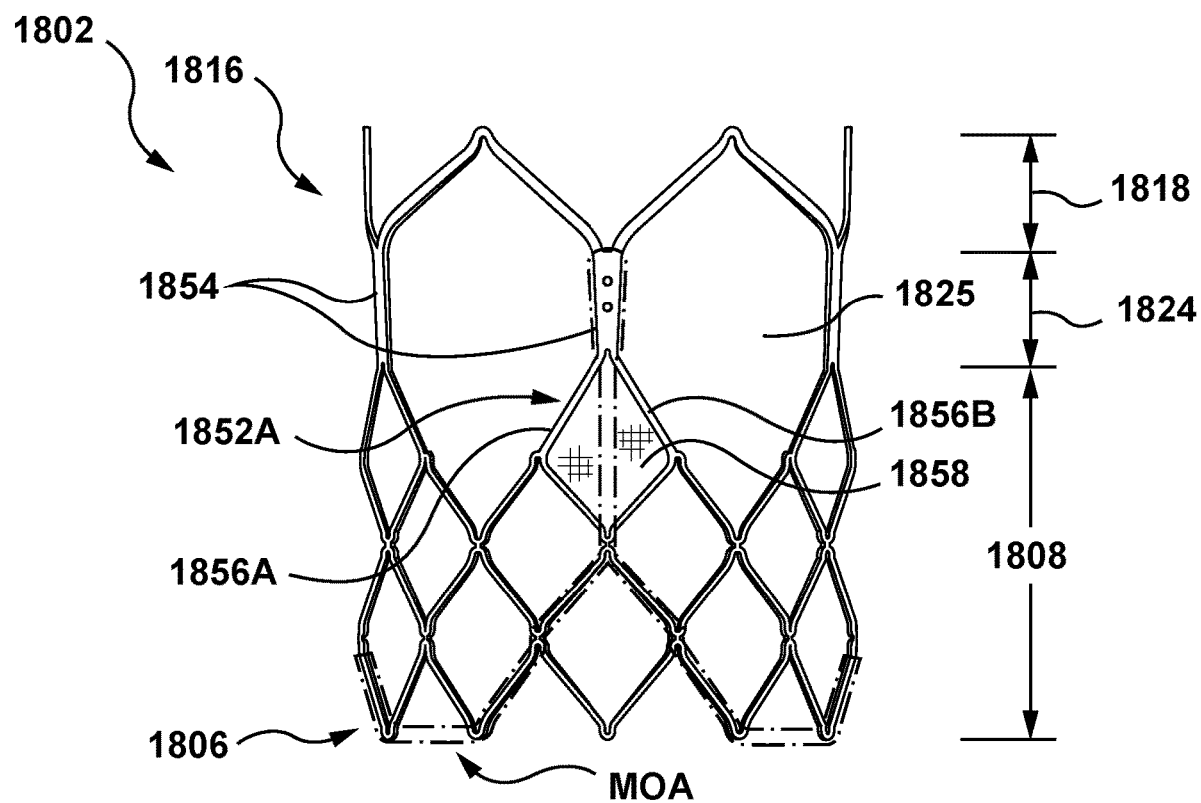
FIG. 19A is a side view of the stent of FIG. 18, wherein the stent is in an expanded configuration.
Figure 19B:
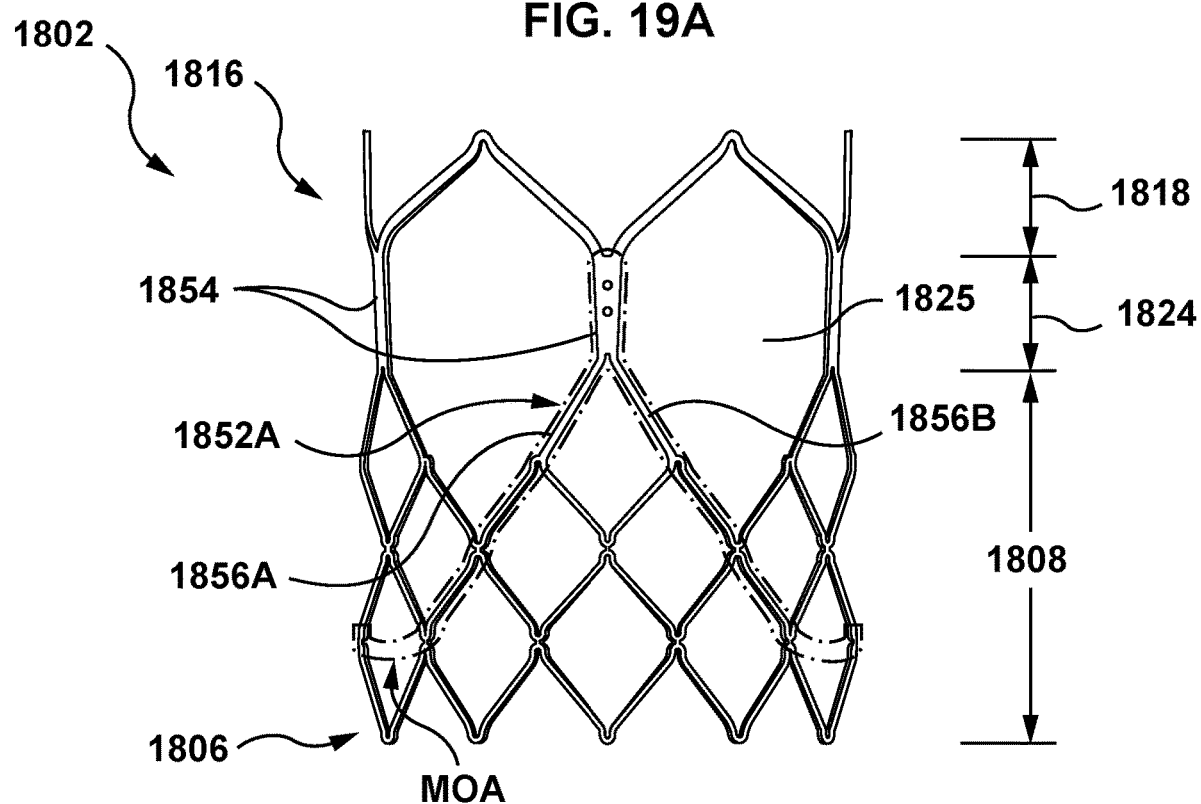
FIG. 19B is a side view of the stent of FIG. 18, wherein the stent is in an expanded configuration and an alternative margin of attachment is illustrated.
Figure 20:
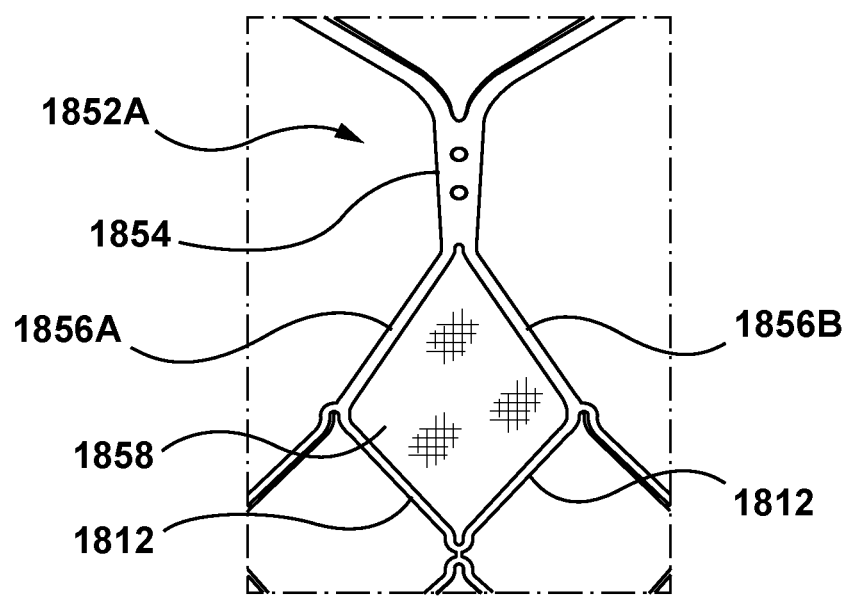
FIG. 20 is an enlarged side view of the stent of FIG. 18, wherein a flap of tissue spans within the transition portion of the stent for attachment to commissures of a prosthetic valve.

FIGS. 18, 19, and 20 illustrate a stent 1802 according to another embodiment hereof in which a plurality of material flaps are utilized for attachment to commissures of the prosthetic valve. The stent 1802 is similar to the stent 1502, except that a transition portion 1824 of the stent 1802 is configured for attachment to commissures of the prosthetic valve rather than the outflow portion 1518 of the stent 1502. FIG. 18 is a side view of the stent 1802 in a non-expanded or crimped configuration, while FIG. 19 is a side view of the stent 1802 in an expanded configuration. FIG. 20 is an enlarged side view of a portion of the stent 1802, and illustrates a material flap 1858 that spans within the transition portion of the stent 1802 for attachment to commissures of a prosthetic valve.

More particularly, the stent 1802 is balloon expandable and includes an inflow portion 1808, an outflow portion 1818, and a transition portion 1824 bridging, connecting, or otherwise extending between the inflow portion 1808 and the outflow portion 1818. The stent 1802 is a tubular component defining a central lumen or passageway (not shown on FIG. 18) and having an inflow or proximal end 1806 and an outflow or distal end 1816. When expanded, a diameter of the inflow end 1806 of the stent 1802 is the same as a diameter of the outflow end 1816 of the stent 1802. The stent 1802 may be formed by a laser-cut manufacturing method and/or another conventional stent forming method as would be understood by one of ordinary skill in the art. The cross-section of the stent 1802 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 1802 may be circular, ellipsoidal, rectangular, hexagonal, square, trapezoidal, wedge-shaped, or other polygonal shape.

A prosthetic valve (not shown) is disposed within and secured to at least the transition portion 1824 of the stent 1802. In addition, the prosthetic valve may also be disposed within and secured to the inflow portion 1808 of the stent 1802. The prosthetic valve is the same as prosthetic valve 132 described above. The inflow portion 1808 is formed proximate to the inflow end 1806 of the stent 1802, and is the same as inflow portion 108 described above. The inflow portion 1808 of the stent 1802 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 1806 of the stent 1802 has a total of twelve endmost inflow crowns 1810A.

The outflow portion 1818 is formed proximate to the outflow end 1816 of the stent 1802. The outflow portion 1818 can be configured in a shape that forms a central lumen or passageway, for example, a ring. The outflow portion 1818 includes a plurality of crowns 1820 and a plurality of struts 1822 with each crown 1820 being formed between a pair of opposing struts 1822. Each crown 1820 is a curved segment or bend extending between opposing struts 1822. Similar to the stent 102, a series of endmost outflow crowns 1820A are formed at the outflow end 1816 of the stent 1802. The outflow end 1816 of the stent 1802 has a total of six endmost outflow crowns 1820A. In an embodiment hereof, the total of the endmost inflow crowns 1810A are twice a total of the endmost outflow crowns 1820A.

The transition portion 1824 bridges, connects, or otherwise extends between the inflow portion 1808 and the outflow portion 1818. While the stent 1824 has been described as including a transition portion 1824, one skilled in the art will realize that the transition portion 1824 may form a portion of the inflow portion 1808 and/or the outflow portion 1818. The transition portion 1824 includes a total of six transition frame members 1852, each transition frame member 1852 extending between an outflow crown 1820 of the outflow portion 1818 and two crowns 1810 of the inflow portion 1808. In the non-expanded or crimped configuration, the transition frame members 1852 are substantially parallel to the central longitudinal axis of the stent 1802. Each transition frame member 1852 includes a planar base or block 1854 and two struts 1856A, 1856B longitudinally extending from the planar base 1854. The planar base 1854 has an increased width relative to a width of a strut 1822 of the outflow portion 1818. Struts 1856A, 1856B are spaced apart from each other. Each strut 1856A, 1856B is attached to a crown 1810 of the inflow portion 1808. Stated another way, each strut 1856A, 1856B is a segment extending between the planar base 1854 and a crown 1810 of the inflow portion 1808. Struts 1856A, 1856B are angled segments extending between the planar base 1854 and a crown 1810 of the inflow portion 1808 when the stent 1802 is in the expanded configuration, as shown on FIG. 19. More particularly, the ends of the struts 1856A, 1856B that are attached to the two crowns 1810 of the inflow portion flare or spread apart when the inflow portion 1808 radially expands. Each transition frame member 1852 is disposed approximately halfway between a pair of adjacent endmost outflow crowns 1820A. Three of the six transition frame members 1852 form commissure cells 1852A and are aligned with a respective commissure of the three leaflets 134 of the prosthetic valve 132. More particularly, commissure cells 1852A are formed via the struts 1856A, 1856B of the transition portion 1824 and a pair of struts 1812 of the inflow portion 1808. As will be described in more detail herein, a material flap 1858 is attached to each commissure cell 1852A. A respective commissure of the three leaflets of the prosthetic valve are attached to the material flaps 1858 as well as to the planar base 1854 of the transition frame member 1852. Three of the transition frame members 1852 form open cells 1852B and are disposed between adjacent commissure cells 1852A. Open cells 1852B are formed via the struts 1856A, 1856B of the transition portion 1824 and a pair of struts 1812 of the inflow portion 1808. Unlike commissure cells 1852A, open cells 1852B are not aligned with a respective commissure of the three leaflets 134 of the prosthetic valve 132 and further do not include a material flap attached thereto. However, in another embodiment hereof, the open cells 1852B may include a material flap or graft material attached thereto but such open cells 1852B are not aligned with a respective commissure of the three leaflets 134 of the prosthetic valve 132.

In this embodiment, the endmost outflow crowns 1820A are not connected to the transition frame members 1852 but rather may be considered to be free or unattached while the remaining outflow crowns 1820 of the outflow portion 1818 are connected to the transition frame members 1852 and disposed closer to the inflow end 1806 than the endmost outflow crowns 1820A. In the embodiment shown, there is a single row of struts 1822 and crowns 1820 coupled to the planar bases 1854 of the transition frame members 1852 and defining the outflow end 1816 of the stent 1802. Further, in the embodiment shown, exactly two struts 1822 and a single crown 1820 of the outflow portion 1818 are disposed between adjacent transition frame members 1852. Such an arrangement provides a series of six endmost outflow side openings 1825 formed at the outflow portion 1818 of the stent 1802. Each endmost outflow side opening 1825 is defined by two adjacent struts 1822 of the outflow portion 1818, two adjacent struts 1812 of the inflow portion 1808, and two adjacent transition frame members 1852 of the transition portion 1824. The endmost outflow side openings 1825 of the outflow portion 1818 are relatively larger than the plurality of side openings 1814 of the inflow portion 1808 to improve access to the coronary arteries. More particularly, the endmost outflow side openings 1825 of the outflow portion 1818 are configured to be of sufficient size to be easily crossed with a coronary guide catheter into either the right coronary artery or the left main coronary artery once the transcatheter valve prosthesis is deployed in situ.

As described above, the transition portion 1824 of the stent 1802 is configured for attachment to commissures of the leaflets of the prosthetic valve. As best shown on FIG. 20, a material flap 1858 is attached to the three commissure cells 1852A. Stated another way, the stent 1802 includes a total of three material flaps 1858 attached thereto. The three material flaps 1858 are aligned with and attached to a respective commissure of the three leaflets of the prosthetic valve. In an embodiment, each commissure cell 1852A and corresponding material flap 1858 is generally diamond-shaped. Each material flap 1858 spans or bridges between struts 1856A, 1856B of the transition portion 1824 and two adjacent struts 1812 of the inflow portion 1808. In this embodiment, the entire perimeter of each material flap 1858 is connected to the stent 1802. The material flap 1858 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 1858 forms a webbing or pad to which a respective commissure of the three leaflets of the prosthetic valve is attached. A margin of attachment MOA is shown in phantom on FIG. 19A and illustrates the placement of the commissures on material flaps 1858 as well as the planar bases 1854 disposed adjacent to the material flaps 1858. Since the three material flaps 1858 are aligned with and attached to a respective commissure of the three leaflets of the prosthetic valve, the material flaps 1858 aid in valve alignment and coaptation. Further, in an embodiment, each material flap 1858 may function like a stress relief during diastole. By functioning as a stress relief, the material flaps 1858 prevent commissure tissue damage, reduce intra-annular leakage, and increase the durability of the prosthetic valve. With the commissures attached to the material flaps 1858 as well as the planar bases 1854 disposed adjacent to the commissure cells 1852A, the commissure attachment region is relatively increased. In another embodiment depicted in FIG. 19, which depicts an alternative margin of attachment MOA, the commissure attachment region is relatively shorter because the commissures are attached only to the planar bases 1854 disposed adjacent to the commissure cells 1852A and the material flaps 1858 may be omitted.

As with the stent 102, the inflow portion 1808 includes exactly three rows of struts 1812 and crowns 1810 between the transition frame members 1852 and the inflow end 1806 of the stent 1802. Further, in this embodiment, two struts 1812 and one crown 1810 are disposed between adjacent transition frame members 1852. In an embodiment, a height or length of the stent 1802 in the expanded configuration is between 20 and 26 mm, the height being measured from the most proximal part thereof to the most distal part thereof. In another embodiment hereof (not shown), the stent 1802 may be formed with lengthened commissure posts having an outflow portion that extends into the outflow portion of the stent as described with respect to FIGS. 30, 31, and 32. Further, the stent 1802 may further include directional markers as described with respect to FIGS. 33-37 and/or inflow markers and outflow markers as described with respect to FIGS. 38A-41D.

Figure 21:
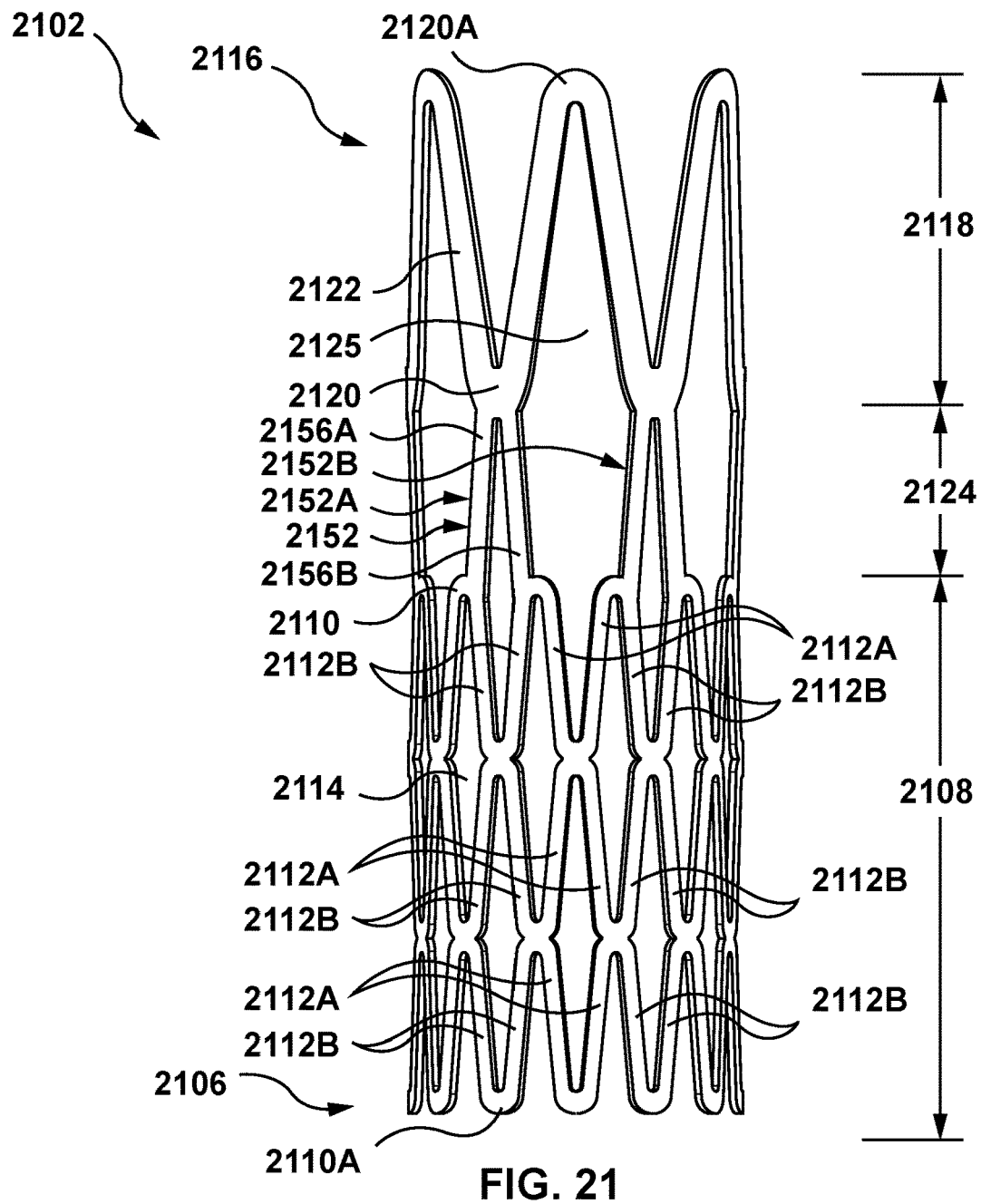
FIG. 21 is a side view of a stent according to another embodiment hereof, wherein the stent is in a non-expanded or crimped configuration and a transition portion of the stent is configured for attachment to commissures of a prosthetic valve.
Figure 22A:
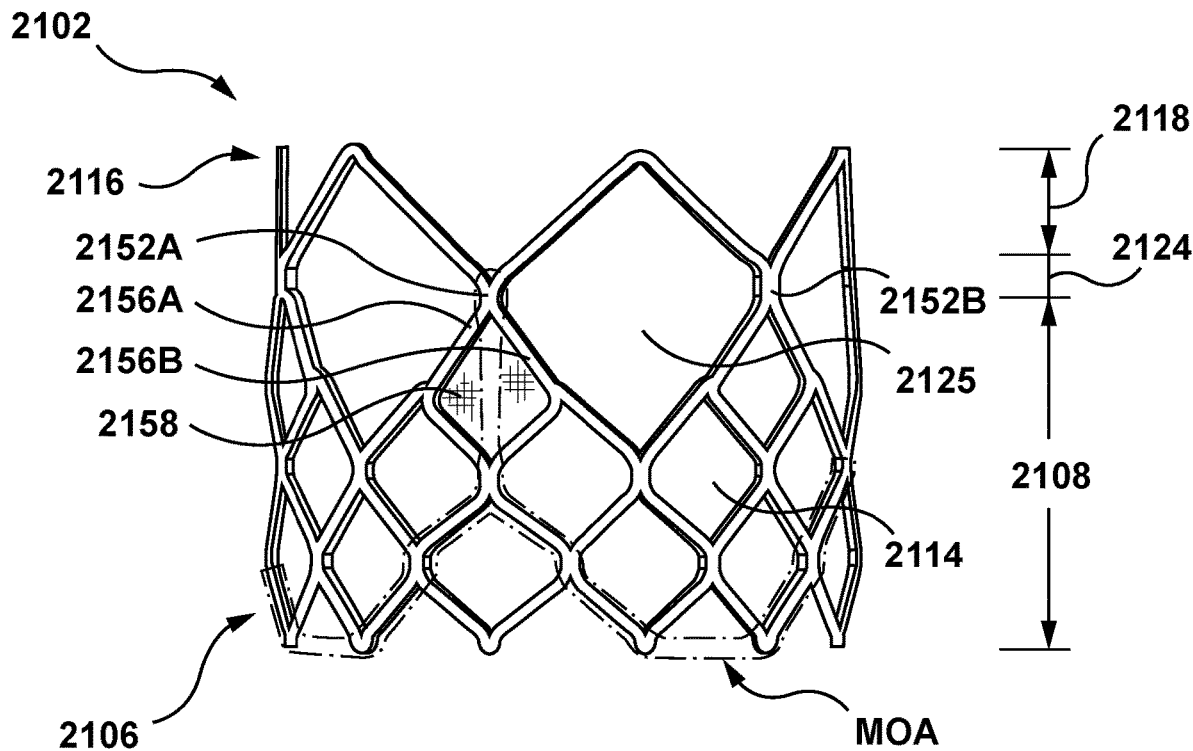
FIG. 22A is a side view of the stent of FIG. 21, wherein the stent is in an expanded configuration.
Figure 22B:
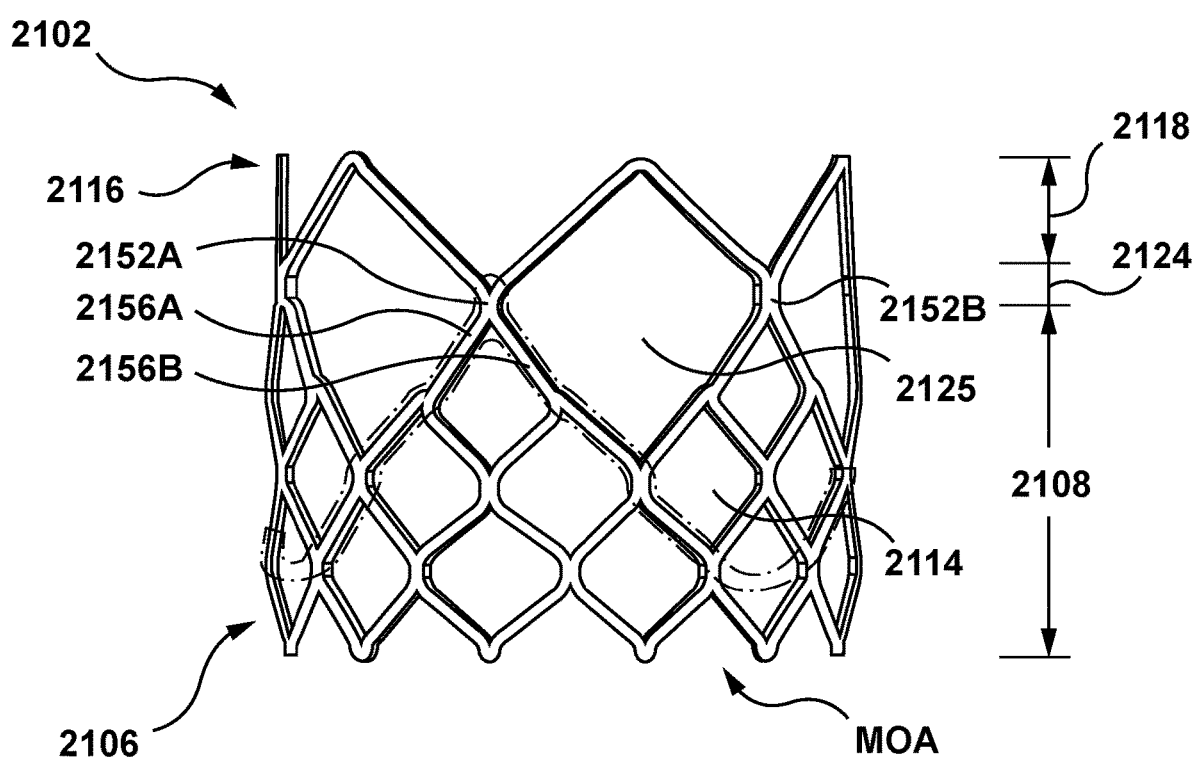
FIG. 22B is a side view of the stent of FIG. 21, wherein the stent is in an expanded configuration and an alternative margin of attachment is illustrated.
Figure 23:
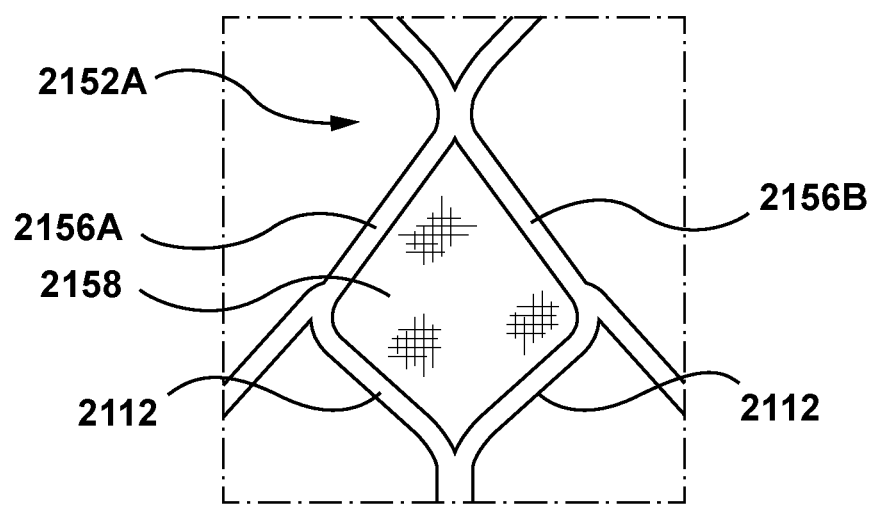
FIG. 23 is an enlarged side view of the stent of FIG. 21, wherein a flap of tissue spans within the transition portion of the stent for attachment to commissures of a prosthetic valve.

FIGS. 21, 21A, 22, and 23 illustrate a stent 2102 according to another embodiment hereof in which a plurality of material flaps are utilized for attachment to commissures of the prosthetic valve. The stent 2102 is similar to the stent 1802, except that a transition portion 2124 of the stent 2102 has a different configuration than the transition portion 1824 of the stent 1802. FIG. 21 is a side view of the stent 2102 in a non-expanded or crimped configuration, while FIG. 22 is a side view of the stent 2102 in an expanded configuration. FIG. 23 is an enlarged side view of the stent 2102 of FIG. 21, and illustrates a material flap 2158 that spans within the transition portion of the stent 2102 for attachment to commissures of a prosthetic valve.

More particularly, the stent 2102 is balloon expandable includes an inflow portion 2108, an outflow portion 2118, and a transition portion 2124 bridging, connecting, or otherwise extending between the inflow portion 2108 and the outflow portion 2118. The stent 2102 is a tubular component defining a central lumen or passageway (not shown on FIG. 21) and having an inflow or proximal end 2106 and an outflow or distal end 2116. When expanded, a diameter of the inflow end 2106 of the stent 2102 is the same as a diameter of the outflow end 2116 of the stent 2102. The stent 2102 may be formed by a laser-cut manufacturing method and/or another conventional stent forming method as would be understood by one of ordinary skill in the art. The cross-section of the stent 2102 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 2102 may be circular, ellipsoidal, rectangular, hexagonal, square, trapezoidal, wedge-shaped, or other polygonal shape.

A prosthetic valve (not shown) is disposed within and secured to at least the transition portion 2124 of the stent 2102. In addition, the prosthetic valve may also be disposed within and secured to the inflow portion 2108 of the stent 2102. The prosthetic valve is the same as prosthetic valve 132 described above. The inflow portion 2108 is formed proximate to the inflow end 2106 of the stent 2102. The inflow portion 2108 of the stent 2102 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 2106 of the stent 2102 has a total of twelve endmost inflow crowns 2110A.

Figure 21A:
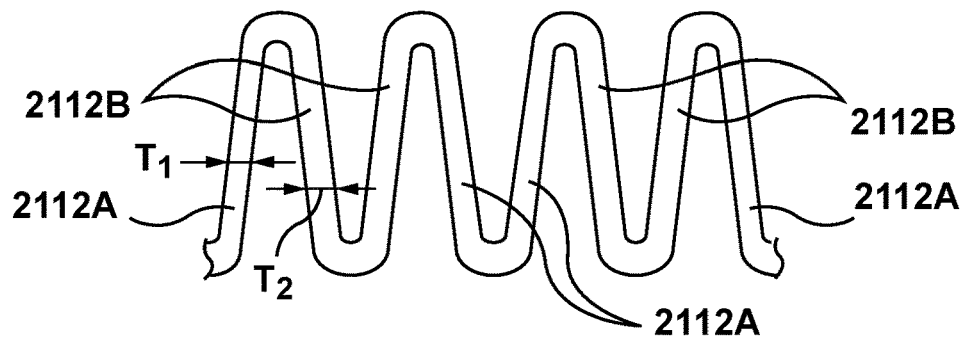
FIG. 21A is an enlarged side view of a portion of an inflow portion of the stent of FIG. 21, wherein the stent is in the non-expanded or crimped configuration.

The inflow portion 2108 is the same as the inflow portion 108 described above, except that the inflow portion 2108 includes struts 2112 that have varying thicknesses. More particularly, as best shown in FIG. 21A which is an enlarged view of a portion of the inflow portion 2108 of the stent 2102, pairs of struts 2112 of the inflow portion 2108 alternate between a first thickness T1 and a second thickness T2, the second thickness T2 being greater than the first thickness T1. For illustrative purposes only, the struts 2112 of the inflow portion 2108 are labeled as struts 2112A having the first thickness T1 and struts 2112B having the second thickness T2. In an embodiment, the first thickness T1 may be 0.32 mm and the second thickness may be 0.38 mm. In an embodiment, as shown on FIG. 21A, struts 2112A having the first thickness are circumferentially aligned with endmost outflow side openings 2125 of the stent 2102 which are described in more detail below, and struts 2112B having the second thickness are circumferentially aligned with transition frame members 2152 which are described in more detail below. The varying thicknesses of the struts 2112 enhance cell symmetry when the stent 2102 is expanded. Stated another way, the varying thicknesses of the struts 2112 configure the stent 2102 to exhibit more uniform cell expansion than when the struts 2112 are formed with unitary thicknesses. Symmetrical cell expansion ensures that the stent 2102 crimps well onto a balloon of a balloon catheter for delivery. Poor crimp quality may lead to portions of the stent 2102 overlapping when crimped, which in turn may cause tissue damage to the valve leaflets of the prosthetic valve during the crimping process. In another embodiment, however, the struts 2112 may alternatively be formed within uniform strut thickness. Further, any embodiment described herein may include an inflow portion having varying strut thickness as shown in the embodiment of FIG. 21 and FIG. 21A.

The outflow portion 2118 is formed proximate to the outflow end 2116 of the stent. The outflow portion 2118 can be configured in a shape that forms a central lumen or passageway, for example, a ring. The outflow portion 2118 includes a plurality of crowns 2120 and a plurality of struts 2122 with each crown 2120 being formed between a pair of opposing struts 2122. Each crown 2120 is a curved segment or bend extending between opposing struts 2122. A series of endmost outflow crowns 2120A are formed at the outflow end 2116 of the stent 2102. Similar to the stent 102, the outflow end 2116 of the stent 2102 has a total of six endmost outflow crowns 2120A. In an embodiment hereof, the total of the endmost inflow crowns 2110A are twice a total of the endmost outflow crowns 2120A.

The transition portion 2124 bridges, connects, or otherwise extends between the inflow portion 2108 and the outflow portion 2118. While the stent 2124 has been described as including a transition portion 2124, one skilled in the art will realize that the transition portion 2124 may form a portion of the inflow portion 2108 and/or the outflow portion 2118. The transition portion 2124 includes a total of six transition frame members 2152, each transition frame member 2152 extending between a crown 2120 of the outflow portion 2118 and two crowns 2110 of the inflow portion 2108. Each transition frame member 2152 includes two struts 2156A, 2156B that radially and longitudinally extend from an outflow crown 2120 of the outflow portion 2118. Each strut 2156A, 2156B is further attached to a crown 2110 of the inflow portion 2108. Stated another way, each strut 2156A, 2156B is an angled segment extending between an outflow crown 2120 of the outflow portion 2118 and a crown 2110 of the inflow portion 2108. Each transition frame member 2152 is disposed approximately halfway between a pair of adjacent endmost outflow crowns 2120A. Three of the six transition frame members 2152 form commissure cells 2152A and are aligned with a respective commissure of the three leaflets 134 of the prosthetic valve 132. More particularly, commissure cells 2152A are formed via the struts 2156A, 2156B of the transition portion 2124 and a pair of struts 2112 of the inflow portion 2108. As will be described in more detail herein, a material flap 2158 is attached to each commissure cell 2152A. A respective commissure of the three leaflets of the prosthetic valve are attached to the material flaps 2158. Three of the transition frame members 2152 form open cells 2152B and are disposed between adjacent commissure cells 2152A. Open cells 2152B are formed via the struts 2156A, 2156B of the transition portion 2124 and a pair of struts 2112 of the inflow portion 2108. Unlike commissure cells 2152A, open cells 2152B are not aligned with a respective commissure of the three leaflets 134 of the prosthetic valve 132 and further do not include a material flap attached thereto. However, in another embodiment hereof, the open cells 2152B may include a material flap or graft material attached thereto but such open cells 2152B are not aligned with a respective commissure of the three leaflets 134 of the prosthetic valve 132.

In this embodiment, the endmost outflow crowns 2120A are not connected to the transition frame members 2152 but rather may be considered to be free or unattached while the remaining outflow crowns 2120 of the outflow portion 2118 are connected to the transition frame members 2152 and disposed closer to the inflow end 2106 than the endmost outflow crowns 2120A. In the embodiment shown, there is a single row of struts 2122 and crowns 2120 coupled to the transition frame members 2152 and defining the outflow end 2116 of the stent 2102. Further, in the embodiment shown, exactly two struts 2122 and a single crown 2120 of the outflow portion 2118 are disposed between adjacent transition frame members 2152. Such an arrangement provides a series of six endmost outflow side openings 2125 formed at the outflow portion 2118 of the stent 2102. Each endmost outflow side opening 2125 is defined by two adjacent struts 2122 of the outflow portion 2118, two adjacent struts 2112 of the inflow portion 2108, and two adjacent transition frame members 2152 of the transition portion 2124. The endmost outflow side openings 2125 of the outflow portion 2118 are relatively larger than a plurality of side openings 2114 of the inflow portion 2108 to improve access to the coronary arteries. More particularly, the endmost outflow side openings 2125 of the outflow portion 2118 are configured to be of sufficient size to be easily crossed with a coronary guide catheter into either the right coronary artery or the left main coronary artery once the transcatheter valve prosthesis is deployed in situ.

As described above, the transition portion 2124 of the stent 2102 is configured for attachment to commissures of the prosthetic valve. As best shown on FIG. 23, a material flap 2158 is attached to each of the three commissure cells 2152A. Stated another way, the stent 2102 includes a total of three material flaps 2158 attached thereto. The three material flaps 2158 are aligned with and attached to a respective commissure of the three leaflets of the prosthetic valve. In an embodiment, each commissure cell 2152A and corresponding material flap 2158 is generally diamond-shaped. Each material flap 2158 spans or bridges between the struts 2156A, 2156B of the transition portion 2124 and two adjacent struts 2112 of the inflow portion 2108. In this embodiment, the entire perimeter of each material flap 2158 is connected to the stent 2102. The material flap 2158 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 2158 forms a webbing or pad to which a respective commissure of the three leaflets of the prosthetic valve is attached. A margin of attachment MOA is shown in phantom on FIG. 22A and illustrates the placement of the commissures on material flaps 2158. Since the three material flaps 2158 are aligned with and attached to a respective commissure of the three leaflets of the prosthetic valve, the material flaps 2158 aid in valve alignment and coaptation. Further, in an embodiment, each material flap 2158 may function like a stress relief during diastole. By functioning as a stress relief, the material flaps 2158 prevent commissure tissue damage, reduce intra-annular leakage, and increase the durability of the prosthetic valve. In another embodiment depicted in FIG. 22B, which depicts an alternative margin of attachment MOA, the commissure attachment region is relatively shorter because the commissures are attached only to the apex of the commissure cell 2152A and the material flaps 2158 may be omitted.

As with the stent 102, the inflow portion 2108 includes exactly three rows of struts 2112 and crowns 2110 between the transition frame members 2152 and the inflow end 2106 of the stent 2102. Further, in this embodiment, two struts 2112 and one crown 2110 are disposed between the adjacent transition frame members 2152. In an embodiment, a height or length of the stent 2102 in the expanded configuration is between 20-26 mm, the height being measured from the most proximal part thereof to the most distal part thereof. Further, the stent 2102 may further include directional markers as described with respect to FIGS. 33-37 and/or inflow markers and outflow markers as described with respect to FIGS. 38A-41D.

Figure 24:
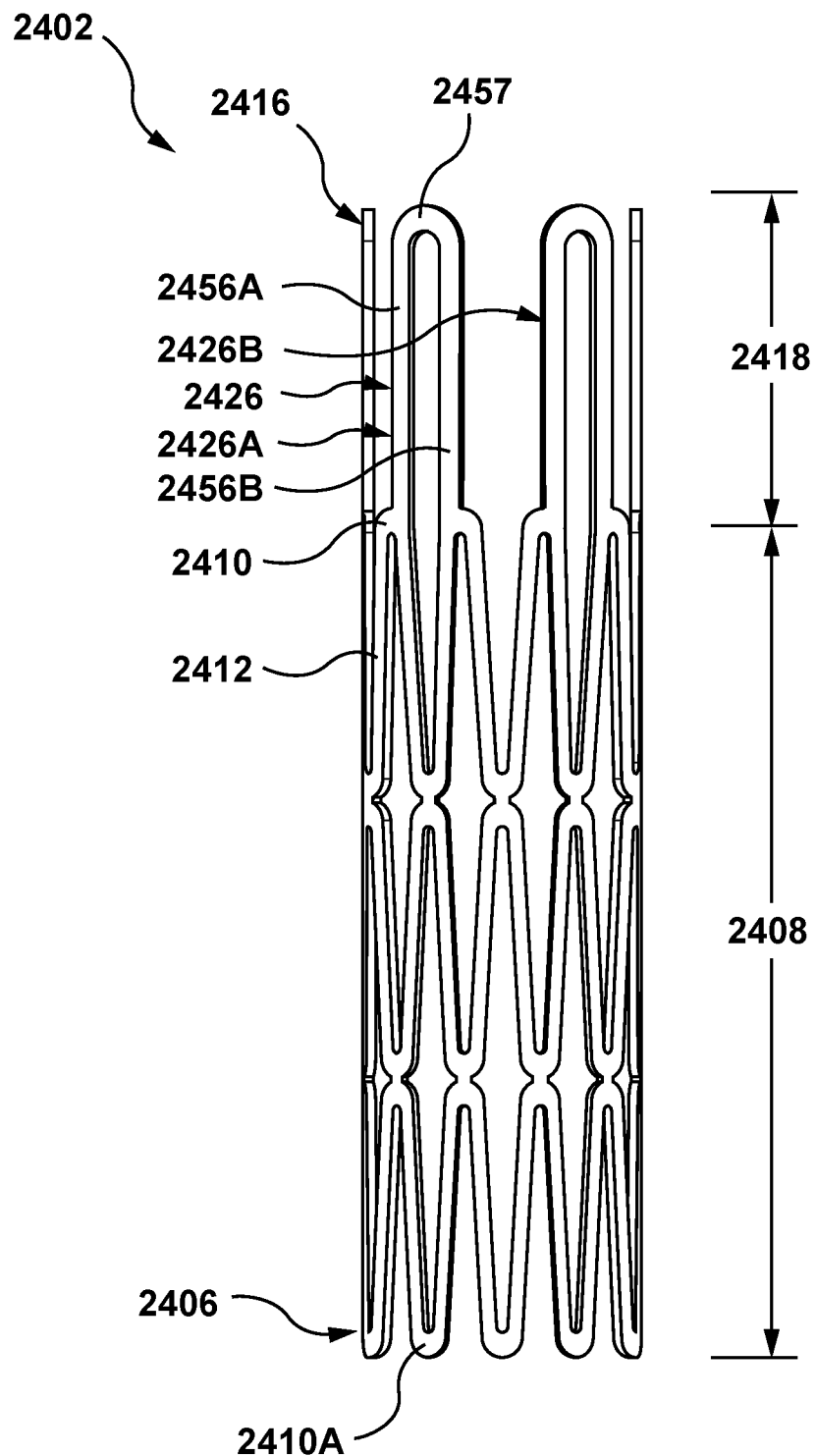
FIG. 24 is a side view of a stent according to another embodiment hereof, wherein the stent is in a non-expanded or crimped configuration and an outflow portion of the stent is configured for attachment to commissures of a prosthetic valve.
Figure 25:
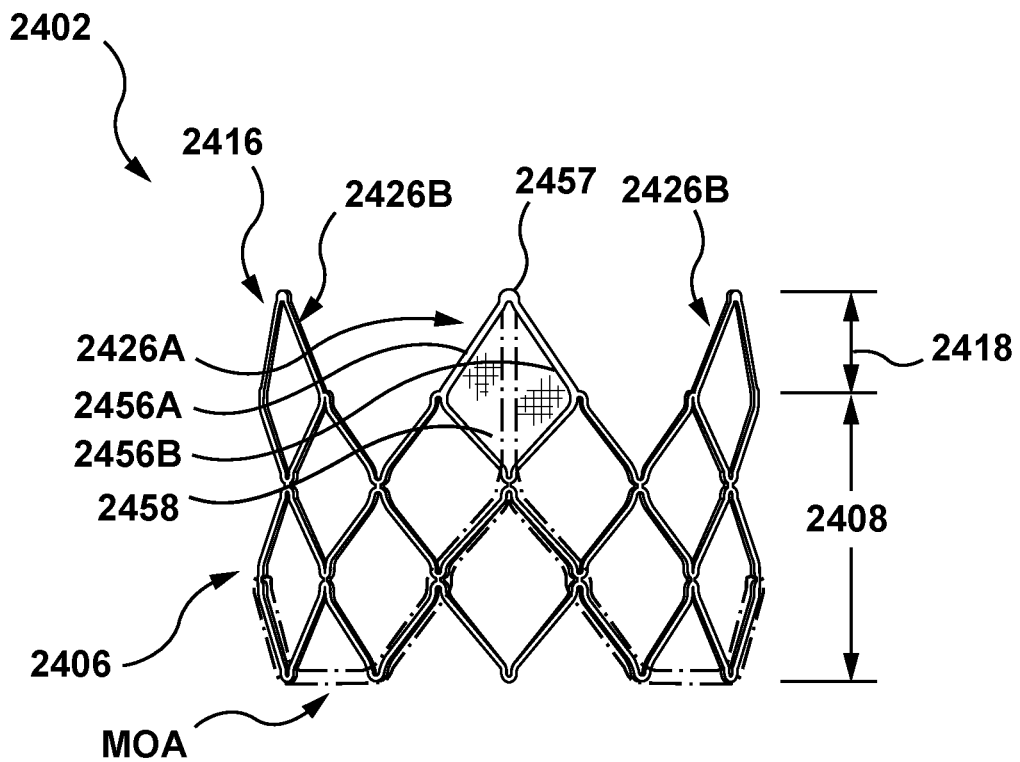
FIG. 25 is a side view of the stent of FIG. 24, wherein the stent is in an expanded configuration.
Figure 26:
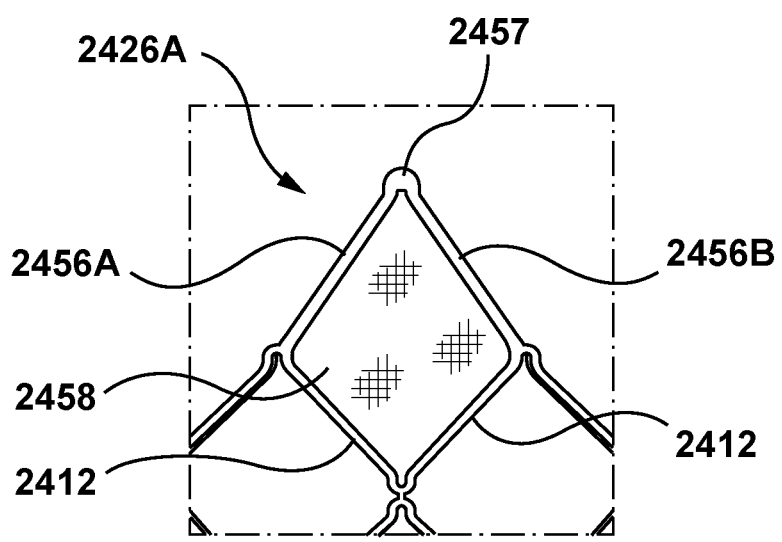
FIG. 26 is an enlarged side view of the stent of FIG. 24, wherein a flap of tissue spans within the outflow portion of the stent for attachment to commissures of a prosthetic valve.

FIGS. 24, 25, and 26 illustrate a stent 2402 according to another embodiment hereof in which a plurality of material flaps are utilized for attachment to commissures of the prosthetic valve. Further, an outflow portion 2418 of a stent 2402 does not include crowns. FIG. 24 is a side view of the stent 2402 in a non-expanded or crimped configuration, while FIG. 25 is a side view of the stent 2402 in an expanded configuration. FIG. 26 is an enlarged side view of the stent 2402 of FIG. 25, and illustrates a material flap spans within the outflow portion 2418 of the stent 2402 for attachment to commissures of a prosthetic valve.

More particularly, the stent 2402 is balloon expandable includes an inflow portion 2408 and the outflow portion 2418. The stent 2402 is a tubular component defining a central lumen or passageway (not shown on FIG. 24) and having an inflow or proximal end 2406 and an outflow or distal end 2416. When expanded, a diameter of the inflow end 2406 of the stent 2402 is the same as a diameter of the outflow end 2416 of the stent 2402. The stent 2402 may be formed by a laser-cut manufacturing method and/or another conventional stent forming method as would be understood by one of ordinary skill in the art. The cross-section of the stent 2402 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 2402 may be circular, ellipsoidal, rectangular, hexagonal, square, trapezoidal, wedge-shaped, or other polygonal shape.

A prosthetic valve (not shown) is disposed within and secured to at least the outflow portion 2418 of the stent 2402. In addition, the prosthetic valve may also be disposed within and secured to the inflow portion 2408 of the stent 2402. The prosthetic valve is the same as prosthetic valve 132 described above. The inflow portion 2408 is formed proximate to the inflow end 2406 of the stent 2402, and is the same as inflow portion 108 described above. The inflow portion 2408 of the stent 2402 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 2406 of the stent 2402 has a total of twelve endmost inflow crowns 2410A.

The outflow portion 2418 is formed proximate to the outflow end 2416 of the stent 2402. The outflow portion 2418 includes a minimum of three outflow frame members 2426. In an embodiment, the outflow portion 2418 includes up to six outflow frame members 2426, with three of the outflow frame members 2426 forming commissure cells 2426A as will be described in more detail herein. Each outflow frame member 2426 is a U-shaped segment that longitudinally extends from two crowns 2410 of the inflow portion 2408. More particularly, each outflow frame member 2426 is a U-shaped segment having two opposing arm segments 2456A, 2456B and a curved segment or bend 2457 extending therebetween. Three of the outflow frame members 2426 form commissure cells 2426A and are aligned with a respective commissure of the three leaflets 134 of the prosthetic valve 132. More particularly, commissure cells 2426A are formed via the U-shaped segment of the outflow portion 2418 and a pair of struts 2412 of the inflow portion 2408. As will be described in more detail herein, a material flap 2458 is attached to each commissure cell 2452A. A respective commissure of the three leaflets of the prosthetic valve are attached to the material flaps 2458. Three of the outflow frame members 2426 form open cells 2426B and are disposed between adjacent commissure cells 2426A. Open cells 2426B are formed via the U-shaped segment of the outflow portion 2418 and a pair of struts 2412 of the inflow portion 2408. Unlike commissure cells 2426A, open cells 2426B are not aligned with a respective commissure of the three leaflets 134 of the prosthetic valve 132 and further do not include a material flap attached thereto. However, in another embodiment hereof, the open cells 2426B may include a material flap or graft material attached thereto but such open cells 2426B are not aligned with a respective commissure of the three leaflets 134 of the prosthetic valve 132.

As best shown on FIG. 26, a material flap 2458 is attached to each of the three commissure cells 2426A. Stated another way, the stent 2402 includes a total of three material flaps 2458 attached thereto. The three material flaps 2458 are aligned with and attached to a respective commissure of the three leaflets of the prosthetic valve. In an embodiment, each commissure cell 2426A and corresponding material flap 2458 is generally diamond-shaped. Each material flap 2458 spans or bridges between arm segments 2456A, 2456B and two adjacent struts 2412 of the inflow portion 2408. In this embodiment, the entire perimeter of each material flap 2458 is connected to the stent 2402. The material flap 2458 may be formed from a material such as those suitable for graft material 244, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 2458 forms a webbing or pad to which a respective commissure of the three leaflets of the prosthetic valve is attached. A margin of attachment MOA is shown in phantom on FIG. 25 and illustrates the placement of the commissures on material flaps 2458. Since the three material flaps 2458 are aligned with and attached to a respective commissure of the three leaflets of the prosthetic valve, the material flaps 2458 aid in valve alignment and coaptation. Further, in an embodiment, each material flap 2458 may function like a stress relief during diastole. By functioning as a stress relief, the material flaps 2458 prevent commissure tissue damage, reduce intra-annular leakage, and increase the durability of the prosthetic valve.

As with the stent 102, the inflow portion 2408 includes exactly three rows of struts 2412 and crowns 2410 between the outflow frame members 2426 and the inflow end 2406 of the stent 2402. Further, two struts 2412 and one crown 2410 are disposed between adjacent outflow frame members 2426. Further, the stent 2402 may further include directional markers as described with respect to FIGS. 33-37 and/or inflow markers and outflow markers as described with respect to FIGS. 38A-41D.

Figure 28:
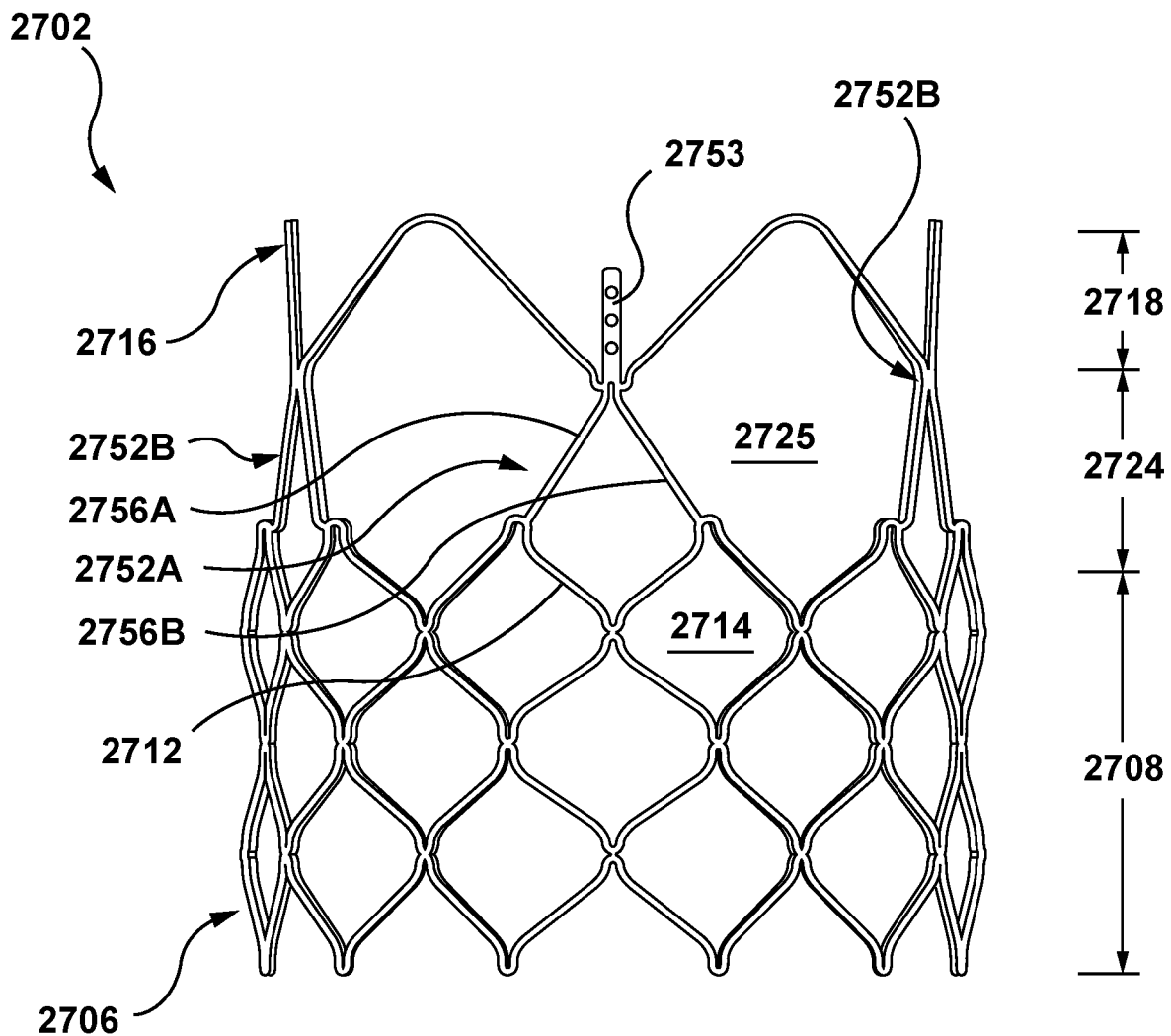
FIG. 28 is a side view of the stent of FIG. 27, wherein the stent is in an expanded configuration.
Figure 29:
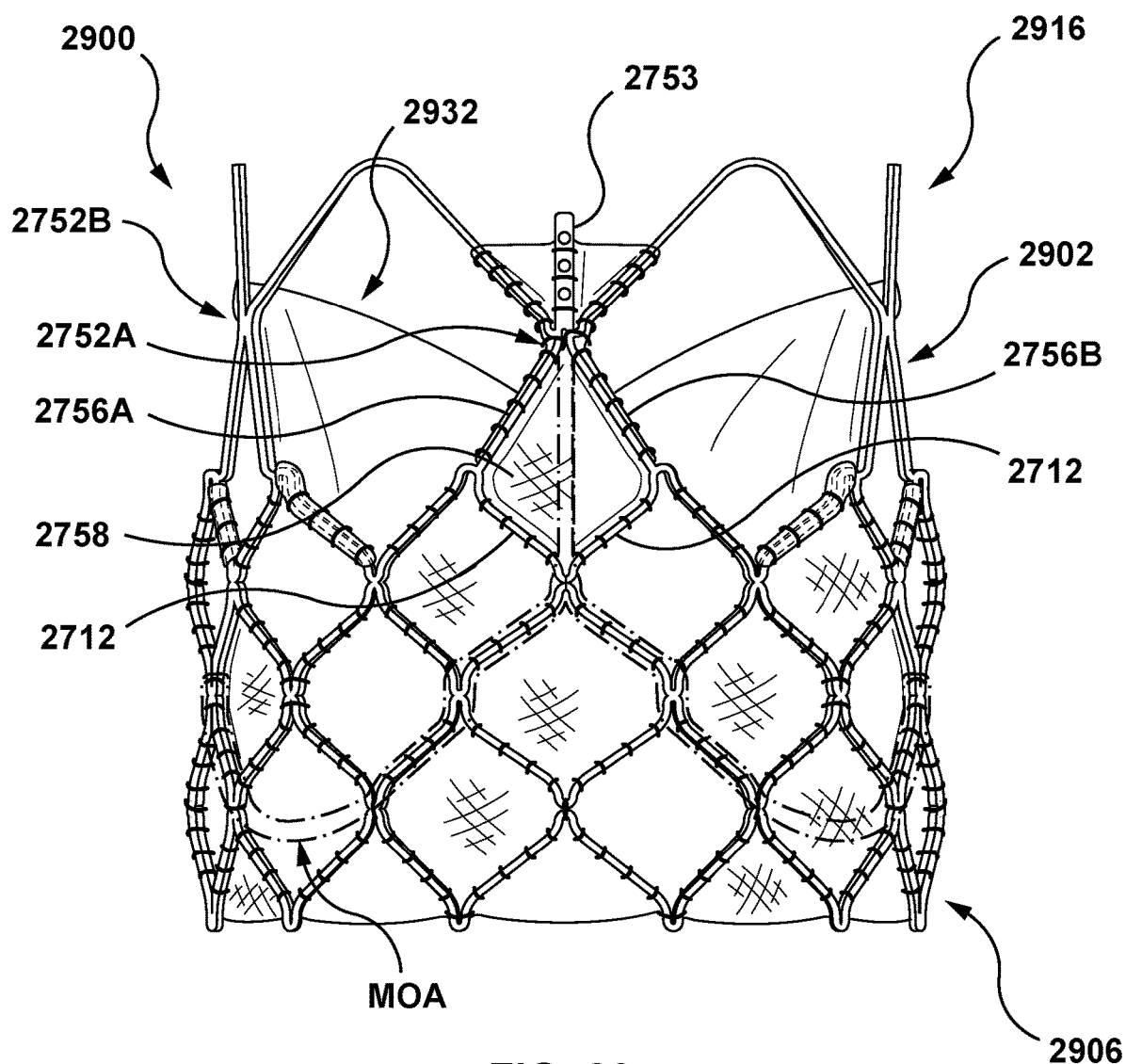
FIG. 29 is a side view of a transcatheter valve prosthesis including the stent of FIG. 27, wherein a flap of tissue spans within the transition portion of the stent for attachment to commissures of a prosthetic valve.

FIGS. 27, 27A, 28, and 29 illustrate a stent 2702 according to another embodiment hereof in which a plurality of material flaps are utilized for attachment to commissures of the prosthetic valve. The stent 2702 is similar to the stent 2102, except that the stent 2702 further includes tapered struts integrally formed therein. FIG. 27 is a side view of the stent 2702 in a crimped configuration, while FIG. 28 is a side view of the stent 2702 in an expanded configuration. FIG. 27A is an enlarged side view of a portion of the stent 2702 of FIG. 27 in a non-expanded or crimped configuration. FIG. 29 is a side view of a transcatheter valve prosthesis 2700 in an expanded configuration, the transcatheter valve prosthesis 2700 including the stent 2702, and illustrates a material flap 2758 that spans within the transition portion of the stent 2702 for attachment to commissures of a prosthetic valve.

More particularly, the stent 2702 is balloon expandable and includes an inflow portion 2708, an outflow portion 2718, and a transition portion 2724 bridging, connecting, or otherwise extending between the inflow portion 2708 and the outflow portion 2718. The stent 2702 is a tubular component defining a central lumen or passageway (not shown on FIG. 27) and having an inflow or proximal end 2706 and an outflow or distal end 2716. When expanded, a diameter of the inflow end 2706 of the stent 2702 is the same as a diameter of the outflow end 2716 of the stent 2702. The stent 2702 may be formed by a laser-cut manufacturing method and/or another conventional stent forming method as would be understood by one of ordinary skill in the art. The cross-section of the stent 2702 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 2702 may be circular, ellipsoidal, rectangular, hexagonal, square, trapezoidal, wedge-shaped, or other polygonal shape.

A prosthetic valve (not shown) is disposed within and secured to at least the transition portion 2724 of the stent 2702. In addition, the prosthetic valve may also be disposed within and secured to the inflow portion 2708 of the stent 2702. The prosthetic valve is the same as prosthetic valve 132 described above. The inflow portion 2708 is formed proximate to the inflow end 2706 of the stent 2702. The inflow portion 2708 of the stent 2702 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 2706 of the stent 2702 has a total of twelve endmost inflow crowns 2710A.

In this embodiment, the inflow portion 2708 includes tapered struts 2712 integrally formed therein. Tapered struts 2712 has a varying thickness along a length thereof such that a middle portion is relatively thinner than opposing end portions of the tapered strut 2712. More particularly, tapered struts 2712 have a thinner cross section in the middle of the length thereof as compared to the cross section at the opposing end portions thereof. As best shown on FIG. 27A, which is an enlarged side view of a portion of the inflow portion 2708 of the stent 2702, a middle or center portion 2760 of the tapered strut 2712 has a first thickness T1 while the end portions of the tapered strut 2712 has a second thickness T2, the second thickness T2 being greater than the first thickness T1. In an embodiment, the first thickness T1 may be 0.32 mm and the second thickness may be 0.38 mm. The tapered struts 2712 result in wider side openings 2714 and allow for graft material to better pack within the wider side openings 2714 when the transcatheter valve prosthesis 2700 is crimped onto a balloon for delivery, thereby resulting in a reduced crossing profile.

The outflow portion 2718 is formed proximate to the outflow end 2716 of the stent 2702. The outflow portion 2718 can be configured in a shape that forms a central lumen or passageway, for example, a ring. The outflow portion 2718 includes a plurality of crowns 2720 and a plurality of struts 2722 with each crown 2720 being formed between a pair of opposing struts 2722. Each crown 2720 is a curved segment or bend extending between opposing struts 2722. A series of endmost outflow crowns 2720A are formed at the outflow end 2716 of the stent 2702. Similar to the stent 102, the outflow end 2716 of the stent 2702 has a total of six endmost outflow crowns 2720A. In an embodiment hereof, the total of the endmost inflow crowns 2710A are twice a total of the endmost outflow crowns 2720A.

The transition portion 2724 bridges, connects, or otherwise extends between the inflow portion 2708 and the outflow portion 2718. While the stent 2724 has been described as including a transition portion 2724, one skilled in the art will realize that the transition portion 2724 may form a portion of the inflow portion 2708 and/or the outflow portion 2718. The transition portion 2724 includes a total of six transition frame members 2752, each transition frame member 2752 extending between a crown 2720 of the outflow portion 2718 and two crowns 2710 of the inflow portion 2708. Each transition frame member 2752 includes two struts 2756A, 2756B that radially and longitudinally extend from an outflow crown 2720 of the outflow portion 2718. Each strut 2756A, 2756B is further attached to a crown 2710 of the inflow portion 2708. Stated another way, each strut 2756A, 2756B is an angled segment extending between an outflow crown 2720 of the outflow portion 2718 and a crown 2710 of the inflow portion 2708. Each transition frame member 2752 is disposed approximately halfway between a pair of adjacent endmost outflow crowns 2720A. Three of the six transition frame members 2752 form commissure cells 2752A and are aligned with a respective commissure of the three leaflets 134 of the prosthetic valve 132. More particularly, commissure cells 2752A are formed via the struts 2756A, 2756B of the transition portion 2724 and a pair of struts 2712 of the inflow portion 2708. As will be described in more detail herein, a material flap 2758 is attached to each commissure cell 2752A. A respective commissure of the three leaflets of the prosthetic valve are attached to the material flaps 2758. Three of the transition frame members 2752 form open cells 2752B and are disposed between adjacent commissure cells 2752A. Open cells 2752B are formed via the struts 2756A, 2756B of the transition portion 2724 and a pair of struts 2712 of the inflow portion 2708. Unlike commissure cells 2752A, open cells 2752B are not aligned with a respective commissure of the three leaflets 134 of the prosthetic valve 132 and further do not include a material flap attached thereto. However, in another embodiment hereof, the open cells 2752B may include a material flap or graft material attached thereto but such open cells 2752B are not aligned with a respective commissure of the three leaflets 134 of the prosthetic valve 132.

In this embodiment, the endmost outflow crowns 2720A are not connected to the transition frame members 2752 but rather may be considered to be free or unattached while the remaining outflow crowns 2720 of the outflow portion 2718 are connected to the transition frame members 2752 and disposed closer to the inflow end 2706 than the endmost outflow crowns 2720A. In the embodiment shown, there is a single row of struts 2722 and crowns 2720 coupled to the transition frame members 2752 and defining the outflow end 2716 of the stent 2702. Further, in the embodiment shown, exactly two struts 2722 and a single crown 2720 of the outflow portion 2718 are disposed between adjacent transition frame members 2752. Such an arrangement provides a series of six endmost outflow side openings 2725 formed at the outflow portion 2718 of the stent 2702. Each endmost outflow side opening 2725 is defined by two adjacent struts 2722 of the outflow portion 2718, two adjacent struts 2712 of the inflow portion 2708, and two adjacent transition frame members 2752 of the transition portion 2724. The endmost outflow side openings 2725 of the outflow portion 2718 are relatively larger than a plurality of side openings 2714 of the inflow portion 2708 to improve access to the coronary arteries. More particularly, the endmost outflow side openings 2725 of the outflow portion 2718 are configured to be of sufficient size to be easily crossed with a coronary guide catheter into either the right coronary artery or the left main coronary artery once the transcatheter valve prosthesis is deployed in situ.

As described above, the transition portion 2724 of the stent 2702 is configured for attachment to commissures of the prosthetic valve. FIG. 29 illustrates the transcatheter valve prosthesis 2700 in an expanded configuration, the transcatheter valve prosthesis 2700 including the stent 2702. As shown on FIG. 29, a material flap 2758 is attached to each of the three commissure cells 2752A. Stated another way, the stent 2702 includes a total of three material flaps 2758 attached thereto. The three material flaps 2758 are aligned with and attached to a respective commissure of the three leaflets of the prosthetic valve. In an embodiment, each commissure cell 2752A and corresponding material flap 2758 is generally diamond-shaped. Each material flap 2758 spans or bridges between the struts 2756A, 2756B of the transition portion 2724 and two adjacent struts 2712 of the inflow portion 2708. In this embodiment, the entire perimeter of each material flap 2758 is connected to the stent 2702. The material flap 2758 may be formed from a material such as those suitable for graft material 144, such as but not limited to a natural or biological material such as pericardium or another membranous tissue such as intestinal submucosa, a low-porosity woven fabric, such as polyester, Dacron fabric, or PTFE, or a knit or woven polyester, such as a polyester or PTFE knit.

Each material flap 2758 forms a webbing or pad to which a respective commissure of the three leaflets of the prosthetic valve is attached. A margin of attachment MOA is shown in phantom on FIG. 29 and illustrates the placement of the commissures on material flaps 2758. Since the three material flaps 2758 are aligned with and attached to a respective commissure of the three leaflets of the prosthetic valve, the material flaps 2758 aid in valve alignment and coaptation. Further, in an embodiment, each material flap 2758 may function like a stress relief during diastole. By functioning as a stress relief, the material flaps 2758 prevent commissure tissue damage, reduce intra-annular leakage, and increase the durability of the prosthetic valve.

Stent 2702 also includes a commissure extension 2753 that extends from commissure cells 2752A to form a lengthened commissure attachment structure. More particularly, each commissure extension 2753 extends into the outflow portion 2718 of the stent 2702 to allow for lengthened commissure attachment structures without increasing the overall height of the transcatheter valve prosthesis 2700. Each commissure extension 2753 is a relatively stiff, axial segment or planar bar having a first end connected to an apex of a commissure cell 2752A of the transition portion 2724 while a second, unattached or free end of each of the commissure extensions 2753 is disposed within the outflow portion 2718. The commissure extensions 2753 function as support features that allow for lengthened commissure attachment structures to further reinforce or strengthen the commissure region of the transcatheter valve prosthesis 2700. Each commissure extension 2753 extends into the outflow portion 2718 of the stent 2702 to allow for lengthened commissure attachment structures without increasing the overall height of the transcatheter valve prosthesis 2700. In an embodiment, the stent 2702 can include a total of three commissure extensions 2753. The commissure extensions 2753 can extend substantially parallel to the central longitudinal axis of the stent 2702 and are circumferentially spaced apart from each other. The commissure extensions 2753 may include holes or openings formed therein as shown in FIG. 29 configured to attach a respective commissure of the three leaflets of the prosthetic valve to the stent 2702. The commissure extensions 2753 may be covered with a graft material as shown on FIG. 29 so as to be atraumatic, although such graft material is not required. In the embodiment of FIG. 29, the graft material covering the commissure extensions 2753 spans to struts 2722 of the outflow portion 2718. Additionally, in some embodiments, the commissure extensions 2753 can include one or more holes or openings to support alignment markers, as described further below.

The commissure extensions 2753 reduce stresses observed at the commissure region during valve loading by spreading out such stresses across a larger area. More particularly, as compared to self-expanding valve stents, balloon expandable valve stents are stiffer and stronger but therefore may place more stress on the valve leaflets attached to the stent 2702. The valve leaflets, which are often formed from tissue, are more durable when the portion of the stent to which they are attached is more flexible, but such stent flexibility may be detrimental to stent fatigue. As such, the commissure extensions 2753 achieve a balance between stent durability and tissue durability because the stent 2702 maintains its strength and durability while the commissure extensions 2753 improve or increase tissue durability of the valve leaflets attached thereto by stress relief from the commissure extensions.

Further, the performance of the transcatheter valve prosthesis 2700 is enhanced by the commissure extensions 2753 without increasing the overall height of the transcatheter valve prosthesis 2700. Notably, each commissure extension 2753 does not extend beyond the endmost outflow crowns 2720A of the outflow portion 2718. For example, in the unexpanded or compressed state illustrated in FIG. 27, the commissure extensions 2753 extend into the outflow portion 2718, but do not extend beyond the endmost outflow crowns 2720A. In the expanded or uncompressed state illustrated in FIG. 28, the commissure extensions 2753 extend into the outflow portion 2718, but do not extend beyond the endmost outflow crowns 2720A. Stated another way, the height of each commissure extension 2753 is not greater than the height of the endmost outflow crowns 2720A and the overall height of the transcatheter valve prosthesis 2700 is not increased by the addition of the commissure extensions 2753. Further, since each commissure extension 2753 is disposed on the outflow side of outflow crowns 2720, the commissure extensions 2753 lengthen the commissure attachment structures without making the transition portion 2724 of the stent 2702 longer. In other words, the commissure attachment structure could alternatively be lengthened along the transition portion 2724, but such additional length along the transition portion 2724 would undesirably increase the overall length of the transcatheter valve prosthesis 2700. Thus, the commissure extensions 2753 result in longer commissure attachment structures without adding overall height. A relatively short or minimized overall height is desirable to increase coronary access and improve system deliverability.

In this embodiment, the inflow portion 2708 includes exactly four rows of struts 2712 and crowns 2710 between the transition frame members 2752 and the inflow end 2706 of the stent 2702. Further, in this embodiment, two struts 2712 and one crown 2710 are disposed between adjacent transition frame members 2752. Further, the stent 2702 may further include directional markers as described with respect to FIGS. 33-37 and/or inflow markers and outflow markers as described with respect to FIGS. 38A-41D.

FIGS. 30, 31, and 32 illustrate a transcatheter valve prosthesis 3000 according to another embodiment hereof in which a radially-expandable stent 3002 includes a plurality of lengthened commissure posts 3026A that are formed to have an axial length greater than the a plurality of axial struts 3026B. As will be described in more detail herein, lengthened commissure posts further reinforce or strengthen the commissure region of the transcatheter valve prosthesis 3000.

More particularly, FIG. 30 is a side view of the transcatheter valve prosthesis 3000 in the expanded configuration and the lengthened commissure posts 3026A are covered with a graft material 3044 so as to be atraumatic, although such graft material is not required. Similar to the stent 102, graft material 3044 also encloses or lines the stent 3002 as would be known to one of ordinary skill in the art of prosthetic tissue valve construction. Graft material 3044 may be a natural or biological material such as pericardium or another membranous tissue such as intestinal submucosa. Alternatively, graft material 3044 may be a low-porosity woven fabric, such as polyester, Dacron fabric, or PTFE, which creates a one-way fluid passage when attached to the stent. In one embodiment, graft material 3044 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

When the transcatheter valve prosthesis 3000 is deployed within the valve annulus of a native heart valve, the stent 3002 of the transcatheter valve prosthesis 3000 is configured to be radially expanded within native valve leaflets of the patient's defective valve, to thereby retain the native valve leaflets in a permanently open state. In embodiments hereof, the transcatheter valve prosthesis 3000 is configured for replacement for an aortic valve such that an inflow end 3006 of the transcatheter valve prosthesis 3000 extends into and anchors within the aortic annulus of a patient's left ventricle, while an outflow end 3016 of the transcatheter valve prosthesis 3000 is positioned within the aortic sinuses.

The stent 3002 has an expanded configuration, which is shown in the side view of FIG. 31, and a non-expanded or crimped configuration, which is shown in the side view of FIG. 32. The non-expanded or crimped configuration as used herein refers to the configuration of the stent 3002 after crimping onto a balloon of a balloon catheter for delivery. Similar to the stent 102, the stent 3002 is mechanically or balloon expandable. As such, the stent 3002 is made from a plastically deformable material such that when expanded by a dilatation balloon, the stent 3002 maintains its radially expanded configuration. The stent 3002 may be formed from stainless steel or other suitable metal, such as platinum iridium, cobalt chromium alloys such as MP35N, or various types of polymers or other materials known to those skilled in the art, including said materials coated with various surface deposits to improve clinical functionality. The stent 3002 is configured to be rigid such that it does not deflect or move when subjected to in-vivo forces, or such that deflection or movement is minimized when subjected to in-vivo forces. In an embodiment, the radial stiffness (i.e., a measurement of how much the stent 3002 deflects when subjected to in-vivo forces) of the stent 3002 is between 80 N/m and 120 N/m, and the radial stiffness of the stent 3002 scaled across the deployed height thereof is approximately 5 N/mm 2. In an embodiment, the radial stiffness of the stent 3002 is greater than 100 N/m. Further, in an embodiment, the device recoil (i.e., a measurement of how much the stent 3002 relaxes after balloon deployment) is below 15% and the approximately recoil after deployment is between 0.5 mm and 2 mm. Further, in an embodiment, the device crush or yield (i.e., the radial force at which the stent 3002 yields) is approximately 200 N.

The stent 3002 may be formed from a unitary frame or scaffold having an inflow portion 3008, an outflow portion 3018, and a transition portion 3024 bridging, connecting, or otherwise extending between the inflow portion 3008 and the outflow portion 3018. The stent 3002 is a tubular component defining a central lumen or passageway (not shown on FIGS. 30-32) and having the inflow or proximal end 3006 and the outflow or distal end 3016. When expanded, a diameter of the inflow end 3006 of the stent 3002 is the same as a diameter of the outflow end 3016 of the stent 3002. The stent 3002 may be formed by a laser-cut manufacturing method and/or another conventional stent forming method as would be understood by one of ordinary skill in the art. The cross-section of the stent 3002 may be circular, ellipsoidal, rectangular, hexagonal, square, trapezoidal, or other polygonal shape, although at present it is believed that circular, ellipsoidal, or trapezoidal may be preferable when utilized with the replacement of an aortic valve. Similarly, the cross-section of the various struts that form the stent 3002 may be circular, ellipsoidal, rectangular, hexagonal, square, trapezoidal, wedge-shaped, or other polygonal shape.

A prosthetic valve (not shown) is disposed within and secured to at least the transition portion 3024 of the stent 3002. In addition, the prosthetic valve may also be disposed within and secured to the inflow portion 3008 of the stent 3002. The prosthetic valve is the same as the prosthetic valve 132 described above. The inflow portion 3008 is formed proximate to the inflow end 3006 of the stent 3002, and is the same as inflow portion 108 described above. The inflow portion 3008 of the stent 3002 may be formed with nodes 111 having abutting crowns 110 as described in FIGS. 9 and 10 above, or may be formed with shortened nodes 1111 having overlapping crowns 1110 as described in FIGS. 11 and 12 above. Similar to the stent 102, the inflow end 3006 of the stent 3002 has a total of twelve endmost inflow crowns 3010A.

The outflow portion 3018 is formed proximate to the outflow end 3016 of the stent 3002. The outflow portion 3018 can be configured in a shape that forms a central lumen or passageway, for example, a ring. The outflow portion 3018 includes a plurality of crowns 3020 and a plurality of struts 3022 with each crown 3020 being formed between a pair of opposing struts 3022. Each crown 3020 is a curved segment or bend extending between opposing struts 3022. Similar to the stent 102, a series of endmost outflow crowns 3020A are formed at the outflow end 3016 of the stent 3002. The outflow end 3016 of the stent 3002 has a total of six endmost outflow crowns 3020A. In an embodiment hereof, the total of the endmost inflow crowns 3010A are twice a total of the endmost outflow crowns 3020A.

The transition portion 3024 bridges, connects, or otherwise extends between the inflow portion 3008 and the outflow portion 3018. While the stent 3024 has been described as including a transition portion 3024, one skilled in the art will realize that the transition portion 3024 may form a portion of the inflow portion 3008 and/or the outflow portion 3018. The transition portion 3024 includes a minimum of three axial frame members 3026, each axial frame member 3026 extending between an outflow crown 3020 of the outflow portion 3018 and a crown 3010 of the inflow portion 3008. The axial frame members 3026 are substantially parallel to the central longitudinal axis of the stent 3002. Each axial frame member 3026 is disposed approximately halfway between a pair of adjacent endmost outflow crowns 3020A. In an embodiment, the transition portion 3024 includes up to six axial frame members 3026, with three of the axial frame members 3026 being lengthened commissure posts 3026A and three of the axial frame members 3026 being axial struts 3026B. The lengthened commissure posts 3026A are circumferentially spaced apart and aligned with and attached to a respective commissure of the three leaflets of the prosthetic valve, and the axial struts 3026B are disposed between adjacent commissure posts 3026A. The axial frame members 3026 aid in valve alignment and coaptation. More particularly, the axial frame members 3026 reinforce or strengthen the commissure region of the prosthetic valve by shaping the leaflets and supporting the leaflets during opening and closing thereof, and thus provide more reliable leaflet coaptation.

In this embodiment, the endmost outflow crowns 3020A are not connected to the axial frame members 3026 but rather may be considered to be free or unattached while the remaining outflow crowns 3020 of the outflow portion 3018 are connected to the axial frame members 3026 and disposed closer to the inflow end 3006 than the endmost outflow crowns 3020A. In the embodiment shown, there is a single row of struts 3022 and crowns 3020 coupled to the axial frame members 3026 and defining the outflow end 3016 of the stent 3002. Further, in the embodiment shown, exactly two struts 3022 and a single crown 3020 of the outflow portion 3018 are disposed between adjacent axial frame members 3026. Such an arrangement provides a series of six endmost outflow side openings or cells 3025 formed at the outflow portion 3018 of the stent 3002. Each endmost outflow side opening or cell 3025 defines an open space in the stent 3002, which is formed in any type of shape, in the radially expanded configuration. In an embodiment, each endmost outflow side opening 3025 is defined by two adjacent struts 3022 of the outflow portion 3018, four adjacent struts of the inflow portion 3008, and two adjacent axial frame members 3026 of the transition portion 3024. The endmost outflow side openings 3025 of the outflow portion 3018 are relatively larger than the plurality of side openings 3014 of the inflow portion 3008 to improve access to the coronary arteries. More particularly, the endmost outflow side openings 3025 of the outflow portion 3018 are configured to be of sufficient size to be easily crossed with a coronary guide catheter into either the right coronary artery or the left main coronary artery once the transcatheter valve prosthesis is deployed in situ.

As with the stent 102, the inflow portion 3008 includes exactly three rows of struts 3012 and crowns 3010 between the axial frame members 3026 and the inflow end 3006 of the stent 3002. Further, in this embodiment, four struts 3012 and three crowns 3010 are disposed between adjacent axial frame members 3026. In an embodiment, a height or length of the stent 3002 in the expanded configuration is between 12 and 24 mm, the height being measured from the most proximal part thereof to the most distal part thereof. In an embodiment hereof, a height or length of the stent 3002 in the expanded configuration is between 15 and 24 mm. For example, in an embodiment the stent 3002 has diameter of between 21-24 mm and a height of 17 mm. In another embodiment, the stent 3002 has diameter of between 24-27 mm and a height of 19 mm. In yet another embodiment, the stent 3002 has diameter of between 27-30 mm and a height of 21 mm. The stent 3002 may further include inflow markers and outflow markers as described with respect to FIGS. 38A-41D.

The lengthened commissure posts 3026A of the stent 3002 will now be described in more detail. The axial frame members 3026 include lengthened commissure posts 3026A that are formed to have an axial length greater than the axial struts 3026B. Each lengthened commissure posts 3026A extends into the outflow portion 3018 of the stent 3002 to allow for lengthened commissure posts without increasing the overall height of the transcatheter valve prosthesis 3000. More particularly, each axial struts 3026B is an axial segment having a first end connected to a crown 3020 of the outflow portion 3018 and a second end 3030 connected to a crown 3010 of the inflow portion 3008. Stated another way, a crown 3020 of the outflow portion 3018 may be considered the outflow end of each axial strut 3026B and a crown 3010 of the inflow portion 3008 may be considered the inflow end of each axial strut 3026B. Conversely, each lengthened commissure posts 3026A is a relatively stiff, axial segment or planar bar having a first end 3072 connected to a crown 3010 of the inflow portion 3008 while a second, unattached or free end 3074 of each of the lengthened commissure posts 3026A is disposed within the outflow portion 3018. Stated another way, a crown 3010 of the inflow portion 3008 may be considered the inflow end of each commissure post 3026A such that each commissure post 3026A extends from struts 3012 of the inflow portion 3008 to the outflow end thereof, which is the unattached or free end 3074 thereof. Because the lengthened commissure posts 3026A are longer than the axial struts 3026B, struts 3022 of the outflow portion 3018 intersect the lengthened commissure posts 3026A at a central or mid-portion 3055 thereof. The location of the connection between struts 3022 of the outflow portion 3018 to the mid-portions 3055 of the lengthened commissure posts 3026A is spaced a distance, in the direction of the inflow end 806, from the unattached or free end 3074 of the lengthened commissure posts 3026A and is also spaced a distance from the inflow end of the lengthened commissure posts 3026A. As such, a first or transition portion 3054A of each lengthened commissure post 3026A is disposed in the transition portion 3024 of the stent 3002 between the mid-portion 3055 and a crown 3010 of the inflow portion 3008 while an second or outflow portion 3054B of each lengthened commissure post 3026A is disposed in the outflow portion 3018 of the stent 3002 between the mid-portion 3055 and the unattached or free end 3074.

The outflow portions 3054B function as support features that allow for lengthened commissure posts 3026A to further reinforce or strengthen the commissure region of the transcatheter valve prosthesis 3000. Each outflow portion 3054B extends into the outflow portion 3018 of the stent 3002 to allow for lengthened commissure posts 3026A without increasing the overall height of the transcatheter valve prosthesis 3000. In an embodiment, the stent 3002 can include a total of three lengthened commissure posts 3026A. The lengthened commissure posts 3026A extend substantially parallel to the central longitudinal axis of the stent 3002 and are circumferentially spaced apart from each other. The lengthened commissure posts 3026A may include holes or openings 3071 formed therein configured to attach a respective commissure of the three leaflets of the prosthetic valve to the stent 3002. Additionally, in some embodiments, the lengthened commissure posts 3026A may include one or more holes or openings to support alignment markers, as described further below.

The lengthened commissure posts 3026A reduce stresses observed at the commissure region during valve loading by spreading out such stresses across a larger area. More particularly, as compared to self-expanding valve stents, balloon expandable valves stents are stiffer and stronger but therefore may place more stress on the valve leaflets attached thereto attached to the stent 3002. The valve leaflets, which are often formed from tissue, are more durable when the portion of the stent to which they are attached is more flexible, but such stent flexibility may be detrimental to stent fatigue. As such, the lengthened commissure posts 3026A achieve a balance between stent durability and tissue durability because the stent 3002 maintains its strength and durability while the lengthened commissure posts 3026A improve or increase tissue durability of the valve leaflets attached thereto by stress relief from the lengthened commissure posts.

Further, the performance of the transcatheter valve prosthesis 3000 is enhanced by the lengthened commissure posts 3026A without increasing the overall height of the transcatheter valve prosthesis 3000. Notably, each lengthened commissure posts 3026A does not extend beyond the endmost outflow crowns 3020A of the outflow portion 3018. For example, in the unexpanded or compressed state illustrated in FIG. 32, the outflow portions 3054B of the lengthened commissure posts 3026A extend into the outflow portion 3018, but do not extend beyond the endmost outflow crowns 3020A. In the expanded or uncompressed state illustrated in FIG. 31, the outflow portions 3054B of the lengthened commissure posts 3026A extend into the outflow portion 3018, but do not extend beyond the endmost outflow crowns 3020A. Stated another way, the height of each lengthened commissure posts 3026A is not greater than the height of the endmost outflow crowns 3020A and the overall height of the transcatheter valve prosthesis 3000 is not increased by the addition of the outflow portions 3054B. Further, since each outflow portion 3054B is disposed on the outflow side of outflow crowns 3020, the outflow portions 3054B lengthen the commissure posts without making the transition portion 3024 of the stent 3002 longer. In other words, the commissure posts could alternatively be lengthened along the transition portion 3024, but such additional length along the transition portion 3024 would undesirably increase the overall length of the transcatheter valve prosthesis 3000. Thus, the outflow portions 3054B result in longer commissure posts without adding overall height. A relatively short or minimized overall height is desirable to increase coronary access and improve system deliverability.

In another embodiment hereof (not shown), the axial struts 3026B of the stent 3002 may also be lengthened to include an outflow portion similar to outflow portion 3054B of the lengthened commissure posts 3026A. Lengthening the axial struts 3026B in addition to the lengthened commissure posts 3026A may aid in valve alignment and coaptation. Symmetrical cell expansion ensures that the stent crimps well onto a balloon of a balloon catheter for delivery. Poor crimp quality may lead to portions of the stent overlapping when crimped, which in turn may cause tissue damage to the valve leaflets of the prosthetic valve during the crimping process.

The lengthened commissure posts 3026A may also include a feature to assist the physician with correctly orienting the transcatheter valve prosthesis 3000 in situ. More particularly, as shown in FIG. 33, a directional marker 3380 is formed on a lengthened commissure posts 3326A. In the embodiment of FIG. 33, the directional marker 3380 is a C-shaped element formed at an unattached or free second end 3374 of the lengthened commissure posts 3326A. The directional marker 3380 allows a physician to correctly interpret the circumferential orientation of the transcatheter valve prosthesis and to clock or rotate the transcatheter valve prosthesis relative to the anatomy to correct the circumferential or rotational orientation if necessary. More particularly, when being positioned in situ, it is very important to avoid blocking the ostia of the right coronary artery and/or the left main coronary artery. Proper circumferential or rotational orientation within the native anatomy reduces the risk of blocking coronary access. The transcatheter valve prosthesis 3000 is rotatable in situ by the delivery system to be positioned in a desired orientation. The directional marker 3380 allows the physician to determine the orientation of the stent in situ and rotate the transcatheter valve prosthesis relative to the anatomy if needed to avoid blocking the coronary arteries. The directional marker 3380 may be identified under fluoroscopy simply by virtue of its distinct shape, but the directional marker 3380 may also include a radiopaque coating to enhance visibility thereof under fluoroscopy.

The directional marker 3380 is disposed on at least one lengthened commissure post 3326A of the stent, but may be disposed on more than one lengthened commissure post 3326A of the stent. The C-shape of the directional marker 3380 helps the physician in determining the location of the lengthened commissure post 3326A and also in determining whether the lengthened commissure post 3326A is facing toward or away from the viewing direction to verify the proper placement of the transcatheter valve prosthesis prior to deploying it on the balloon delivery system. More particularly, since the C-shape of the directional marker looks different when viewed from a front view or position as compared to when viewed from a reverse view or position, the physician can determine whether the lengthened commissure post 3326A is facing toward or away from the viewing direction, in other words, the C-shape of the directional marker 3380 is an axially non-symmetrical element such that depending upon the location in situ, the C-shape of the directional marker may be displayed to the physician as a "C" or may be displayed to the physician backwards or as a mirror image of a "C". Since the optimal circumferential or rotational orientation of the transcatheter valve prosthesis relative to the coronary arteries can be verified prior to releasing the transcatheter valve prosthesis from the delivery system, the physician can ensure that the transcatheter valve prosthesis is properly oriented in the native anatomy so as to not block the coronary arteries.

Other configurations of a directional marker may be utilized herein. For example, in FIG. 34, another embodiment of a directional marker 3480 is shown. In this embodiment, the directional marker is a C-shaped opening formed at an unattached or free second end 3474 of a lengthened commissure post 3426A. Similar to the C-shape of the directional marker 3380, the C-shape of the directional marker 3380 helps the physician in determining the location of the lengthened commissure post 3426A and also in determining whether the lengthened commissure post 3426A is facing toward or away from the viewing direction to verify the proper placement of the valve prior to releasing it from the delivery system. More particularly, since the C-shape of the directional marker looks different when viewed from a front view or position as compared to when viewed from a reverse view or position, the physician can determine whether the lengthened commissure post 3426A is facing toward or away from the viewing direction. In other words, the C-shape of the directional marker 3480 is an axially non-symmetrical opening such that depending upon the location in situ, the C-shape of the directional marker may be displayed to the physician as a "C" or may be displayed to the physician backwards or as a mirror image of a "C". The directional marker 3480 may be identified under fluoroscopy simply by virtue of its distinct shape, but the directional marker 3480 may also include a radiopaque coating on the structure defining the C-shaped opening to enhance visibility thereof under fluoroscopy.

Further, the directional marker may be any letter, number, symbol, or shape that looks different when viewed from a front view or position as compared to when viewed from a reverse view or position. For example, in FIG. 35, another embodiment of a directional marker 3580 is shown. In this embodiment, the directional marker is a P-shaped element formed at an unattached or free second end 3574 of a lengthened commissure post 3526A. Similar to the letter "C", the P-shape of the directional marker 3580 helps the physician in determining the location of lengthened commissure posts 3526A and also in determining whether the lengthened commissure post 3526A is facing toward or away from the viewing direction to verify the proper placement of the valve prior to releasing it from the delivery system. More particularly, since the P-shape of the directional marker looks different when viewed from a front view or position as compared to when viewed from a reverse view or position, the physician can determine whether the lengthened commissure posts 3526A is facing toward or away from the viewing direction. In other words, the P-shape of the directional marker 3580 is an axially non-symmetrical element such that depending upon the location in situ, the P-shape of the directional marker may be displayed to the physician as a "P" or may be displayed to the physician backwards or as a mirror image of a "P". Further, although not shown, the directional marker may alternatively be a P-shaped opening formed at the unattached or free second end 3574 of the lengthened commissure post 3526A. The directional marker 3580 may be identified under fluoroscopy simply by virtue of its distinct shape, but the directional marker 3580 may also include a radiopaque coating to enhance visibility thereof under fluoroscopy.

Figure 35:
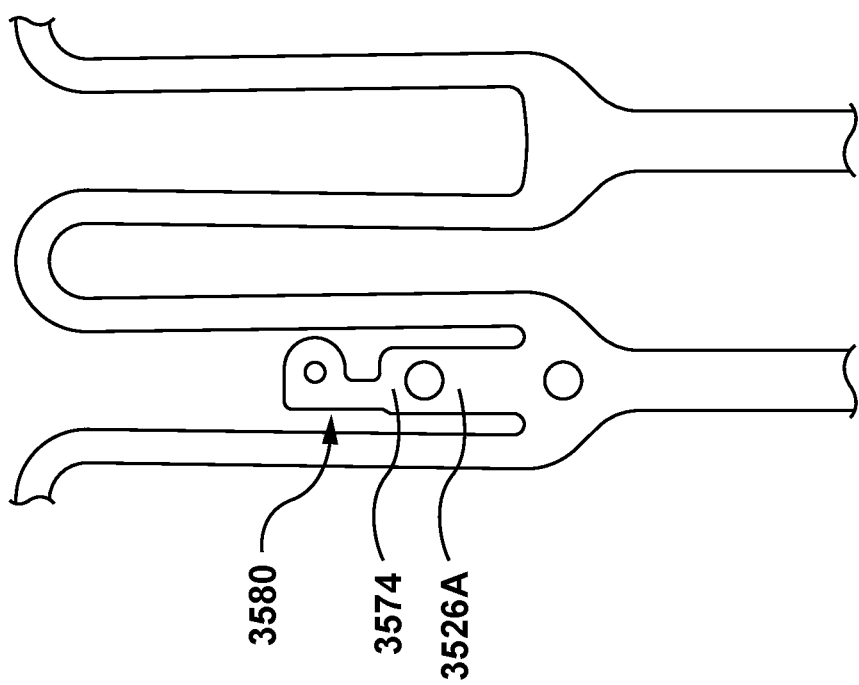
FIG. 35 is an enlarged side view of a portion of a lengthened commissure post according to another embodiment hereof, wherein the lengthened commissure post includes a directional marker and the directional marker is a P-shaped element.

Although the directional markers of FIGS. 33-35 are disposed on the outflow portion of the lengthened commissure post, a directional marker may alternatively be formed at different locations along the length of the lengthened commissure post such as on the transition portion or mid-portion thereof. For example, in FIG. 36, another embodiment of a directional marker 3680 is shown. In this embodiment, the directional marker is a C-shaped opening formed along a length of a lengthened commissure post 3626A. The lengthened commissure post 3626A includes a first or transition portion 3654A disposed in the transition portion of the stent similar to the transition portion 3054A described above while an outflow portion 3654B of each lengthened commissure post 3626A is disposed in the outflow portion of the stent similar to the outflow portion 3054B described above. In this embodiment, the directional marker 3680 is disposed along the transition portion 3654A of the lengthened commissure post 3626A. Similar to the above C-shaped directional markers, the C-shape of the directional marker 3680 helps the physician in determining the location of the lengthened commissure post 3626A and also in determining whether the lengthened commissure post 3626A is facing toward or away from the viewing direction to verify the proper placement of the valve prior to releasing it from the delivery system. More particularly, since the C-shape of the directional marker looks different when viewed from a front view or position as compared to when viewed from a reverse view or position, the physician can determine whether the commissure post 3626A is facing toward or away from the viewing direction. Although shown as a C-shaped opening, the directional marker 3680 may be any letter, number, symbol, or shape that looks different when viewed from a front view or position as compared to when viewed from a reverse view or position. The C-shaped directional marker 3680 is shown as an example as the C-shape is relatively easy to form during manufacture and the front view is readily distinguishable from the reverse view. Although described herein with a C-shape opening, the opening of the directional marker 3680 may be any letter, number, symbol, or shape that looks different when viewed from a front view or position as compared to when viewed from a reverse view or position. The directional marker 3680 may be identified under fluoroscopy simply by virtue of its distinct shape, but the directional marker 3680 may also include a radiopaque coating on the structure defining the C-shaped opening to enhance visibility thereof under fluoroscopy.

Figure 37:
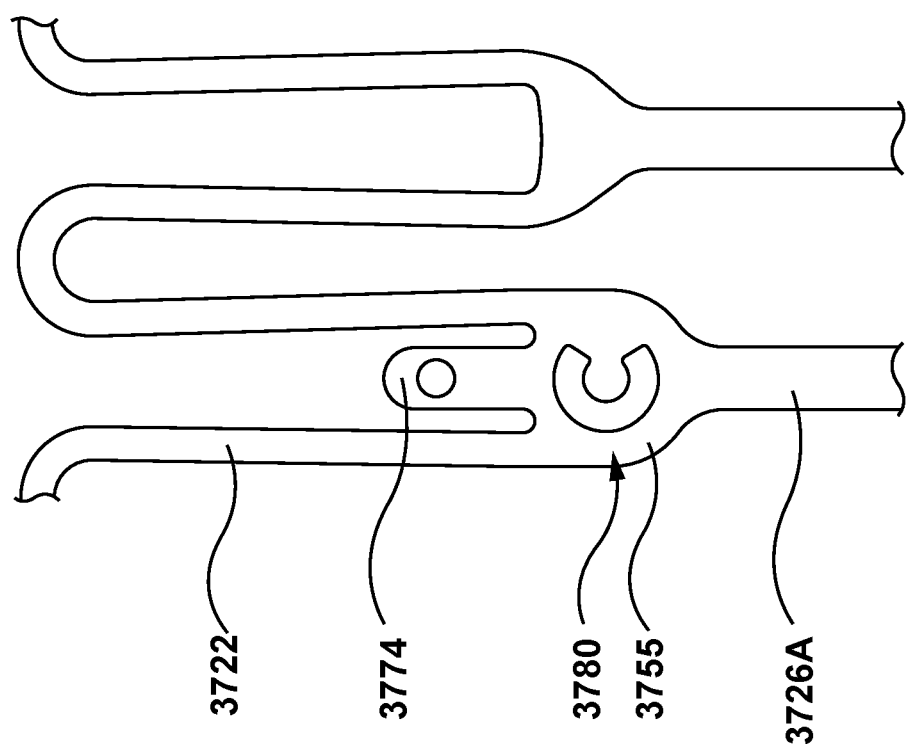
FIG. 37 is an enlarged side view of a portion of a lengthened commissure post according to another embodiment hereof, wherein the lengthened commissure post includes a directional marker and the directional marker is a C-shaped opening.

FIG. 37 depicts another embodiment of a directional marker 3780 is shown. In this embodiment, the directional marker is a C-shaped opening formed at a central or mid-portion 3755 of a lengthened commissure post 3726A where the struts 3722 of the outflow portion of the stent intersect the lengthened commissure posts 3726A. Similar to the above C-shaped directional markers, the C-shape of the directional marker 3780 helps the physician in determining the location of the lengthened commissure post 3726A and also in determining whether the lengthened commissure post 3726A is facing toward or away from the viewing direction to verify the proper placement of the valve prior to releasing it from the delivery system. More particularly, since the C-shape of the directional marker looks different when viewed from a front view or position as compared to when viewed from a reverse view or position, the physician can determine whether the commissure post 3726A is facing toward or away from the viewing direction. Although shown as a C-shaped opening, the directional marker 3780 may be any letter, number, symbol, or shape that looks different when viewed from a front view or position as compared to when viewed from a reverse view or position. The C-shaped directional marker 3780 is shown as an example as the C-shape is relatively easy to form during manufacture and the front view is readily distinguishable from the reverse view. Although described herein with a C-shape opening, the opening of the directional marker 3780 may be any letter, number, symbol, or shape that looks different when viewed from a front view or position as compared to when viewed from a reverse view or position. The directional marker 3780 may be identified under fluoroscopy simply by virtue of its distinct shape, but the directional marker 3780 may also include a radiopaque coating on the structure defining the C-shaped opening to enhance visibility thereof under fluoroscopy.

FIGS. 38A-38E illustrate a transcatheter valve prosthesis 3800 according to another embodiment hereof in which a radially-expandable stent 3802 thereof incudes one or more inflow markers 3860 and an first outflow marker 3870. In embodiments, the inflow markers 3860 and the first outflow marker 3870 can be utilized in orientation (e.g., axial/annular alignment, tilt alignment, circumferential (rotational) alignment, etc.) of the transcatheter valve prosthesis 3800, in situ, as discussed in detail below.

One skilled in the art will realize that FIGS. 38A-38E illustrate one example of an implantable medical device and that existing components illustrated in FIGS. 38A-38E may be removed and/or additional components may be added. Additionally, while the transcatheter valve prosthesis 3800 is described below as including the one or more inflow markers 3860 and the first outflow marker 3870, one skilled in the art will realize that the transcatheter valve prosthesis 3800 can include additional markers, for example, any of the markers described herein. Moreover, while the one or more inflow markers 3860 and the first outflow marker 3870 are described herein with respect to the transcatheter valve prosthesis 3800, one skilled in the art will realize that any embodiment of the transcatheter valve prostheses described herein can include one or more inflow markers 3860 and the first outflow marker 3870.

Figure 38A:
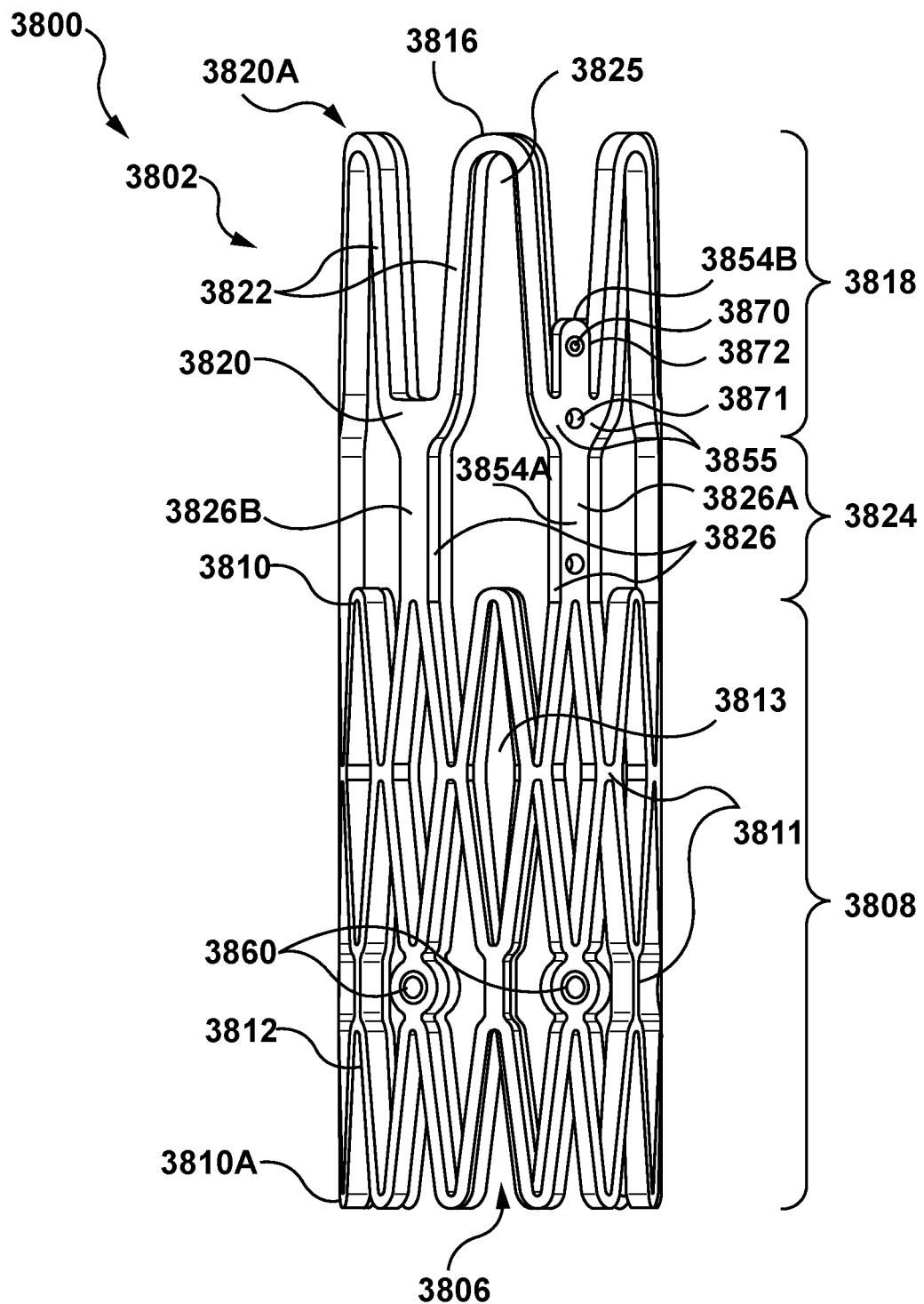
FIGS. 38A-38E illustrate a transcatheter valve prosthesis in accordance with an embodiment hereof.
Figure 38B:
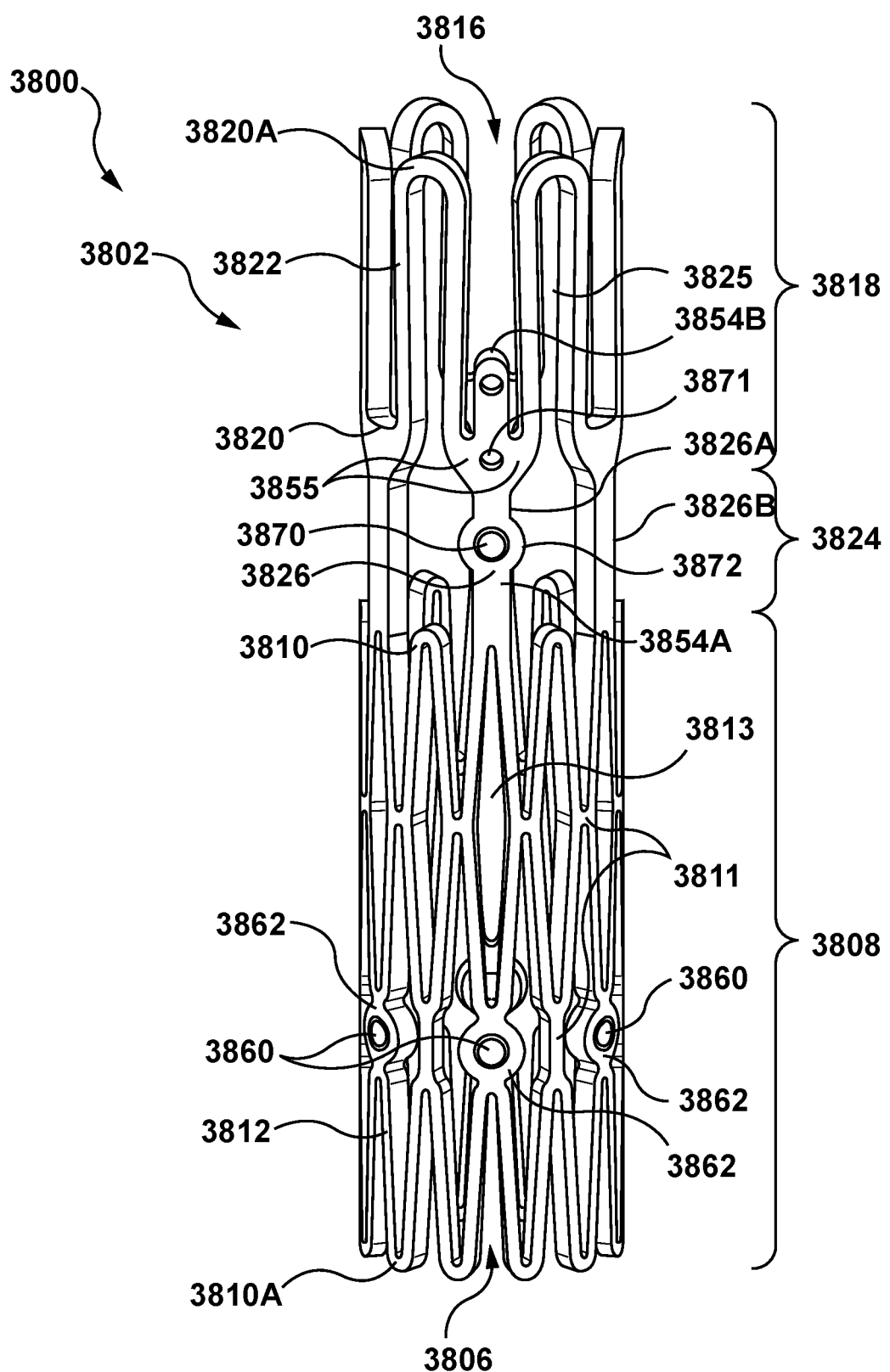
Figure 38C:
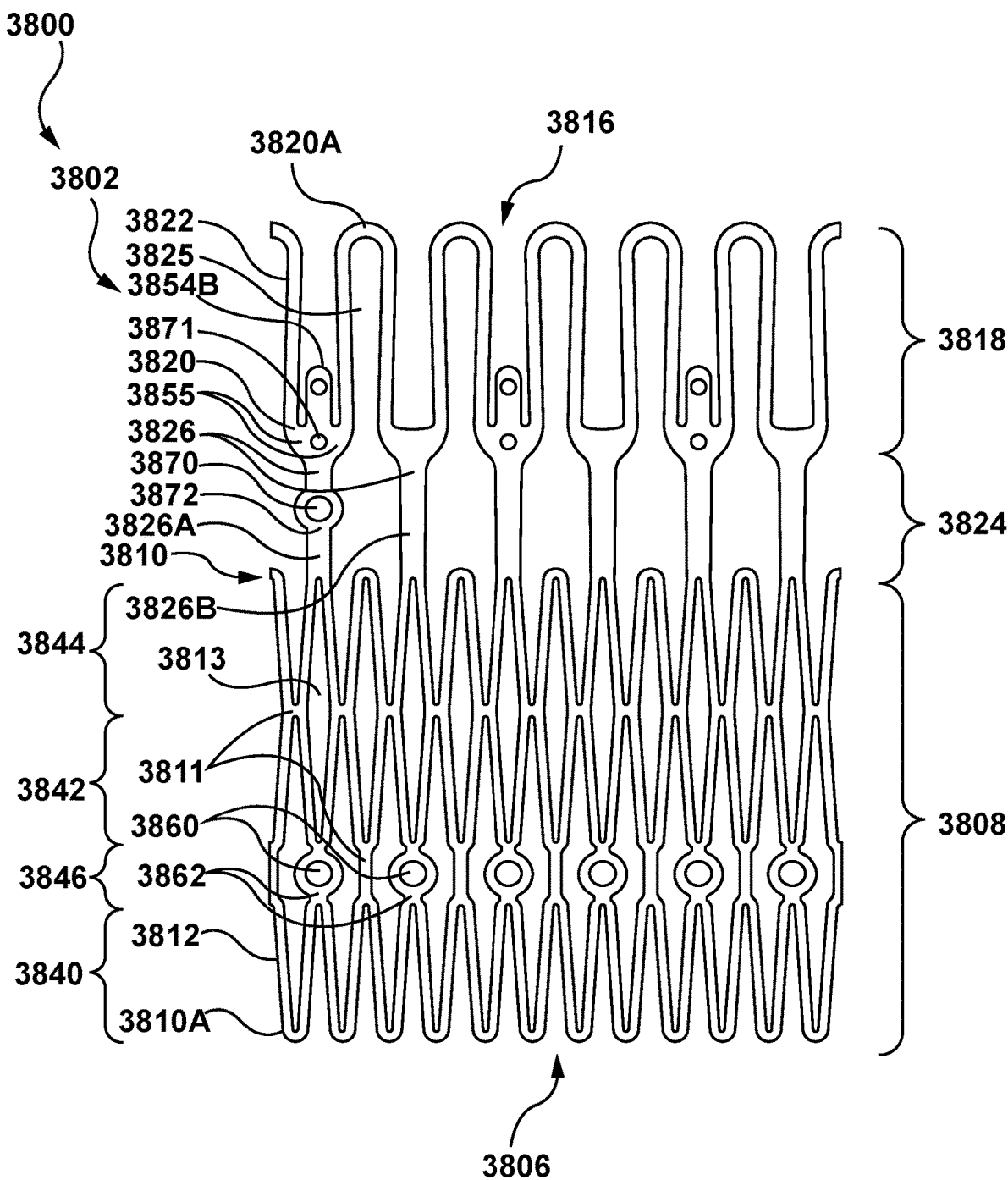
Figure 38D:
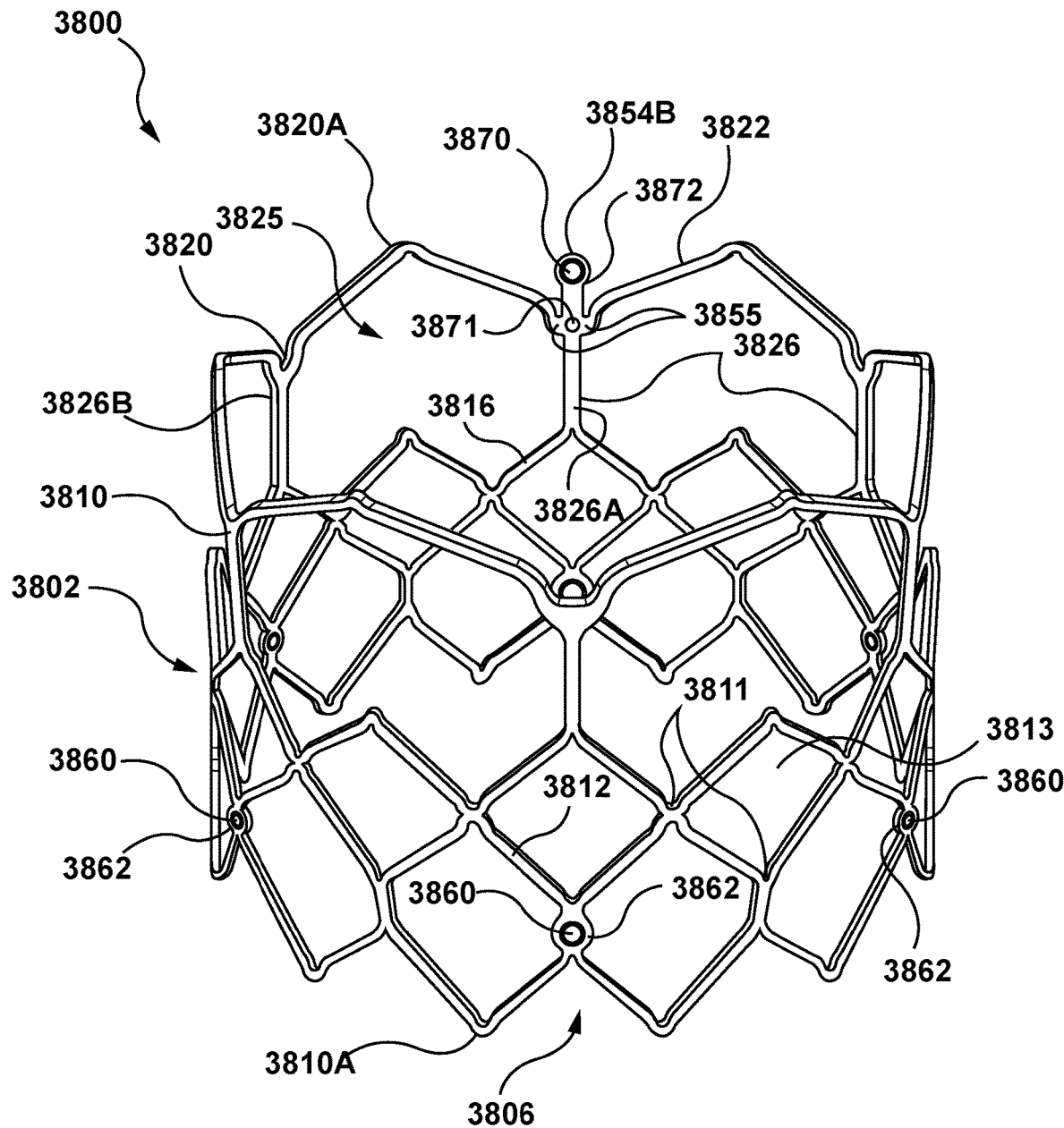
Figure 38E:
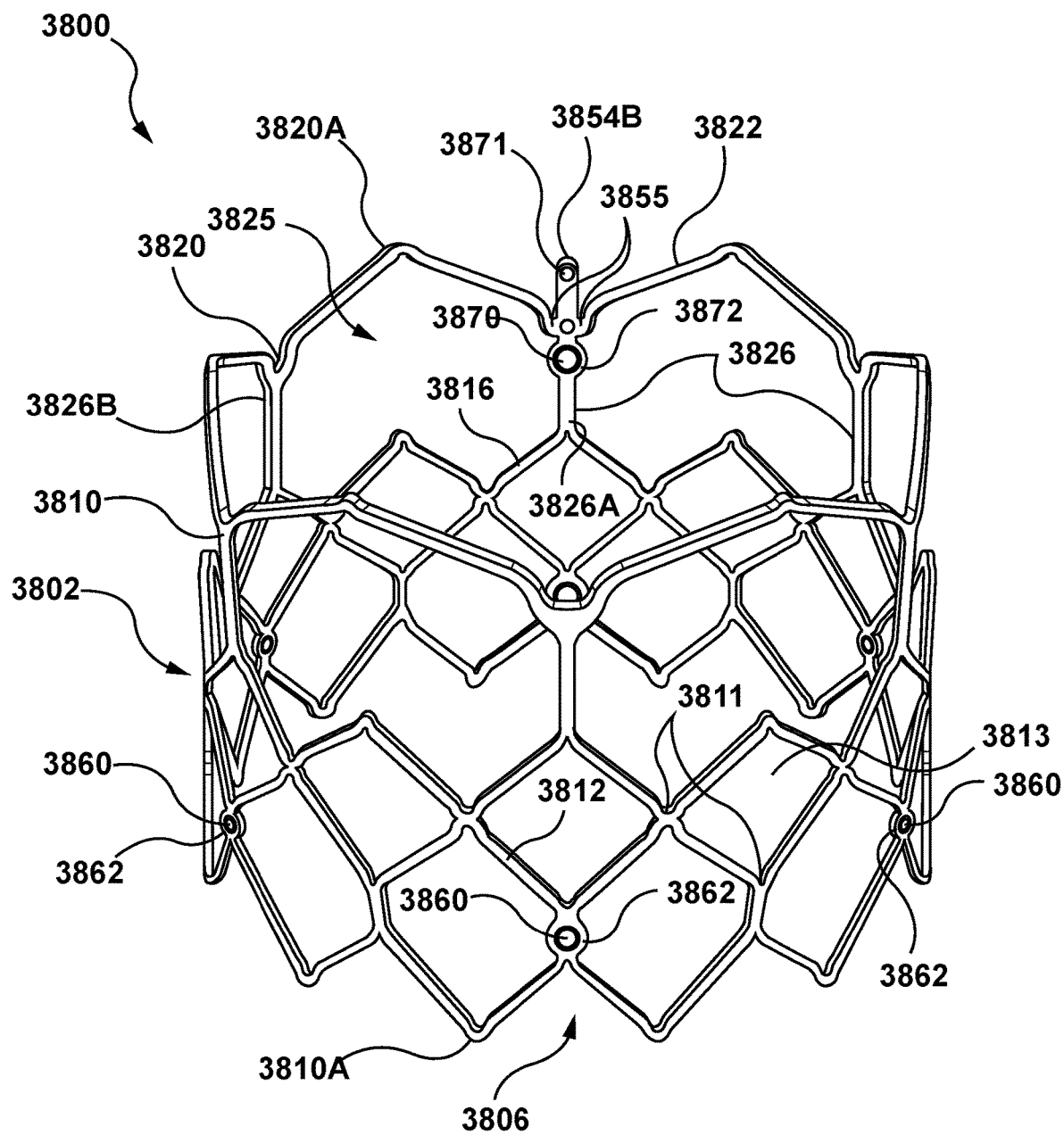

The stent 3802 has a non-expanded or crimped configuration, which is shown in a side view of FIGS. 38A and 38B, and an expanded configuration, which is shown FIGS. 38D and 38E. Non-expanded or crimped configuration as used herein refers to the configuration of the stent 3802 after crimping, for example, onto a balloon of a balloon catheter for delivery. The stent 3802 is mechanically or balloon expandable. As such, the stent 3802 can be made from a plastically deformable material such that, when expanded by a dilatation balloon, the stent 3802 maintains its radially expanded configuration after balloon deflation. The stent 3802 can be formed from stainless steel or other suitable metal, such as platinum iridium, cobalt chromium alloys such as MP35N, or various types of polymers or other materials known to those skilled in the art, including said materials coated with various surface deposits to improve clinical functionality.

The stent 3802 can be configured to be rigid such that it does not deflect or move when subjected to in-vivo forces, or such that deflection or movement is minimized when subjected to in-vivo forces. In an embodiment, the radial stiffness (i.e., a measurement of how much the stent 3802 deflects when subjected to in-vivo forces) of the stent 3802 can be between 80 N/m and 120 N/m, and the radial stiffness of the stent 3802 scaled across the deployed height thereof is approximately 5 N/mm$^2$. In an embodiment, the radial stiffness of the stent 3802 can be greater than 100 N/m. Further, in an embodiment, the device recoil (i.e., a measurement of how much the stent 3802 relaxes after balloon deployment) can below 15% and the approximate recoil after deployment is between 0.5 mm and 2 mm. Further, in an embodiment, the device crush or yield (i.e., the radial force at which the stent 3802 yields) can be approximately 200 N. While the above describes examples of radial stiffness for the stent 3802, one skilled in the art will realize that the stent 3802 may have any radial stiffness as required by a given application and/or governed by the design and construction of the stent 3802.

The stent 3802 can be formed from a unitary frame or scaffold having an inflow portion 3808, an outflow portion 3818, and a transition portion 3824 bridging, connecting, or otherwise extending between the inflow portion 3808 and the outflow portion 3818. The stent 3802 can be a generally tubular component defining a central lumen or passageway and can have an inflow or proximal end 3806 and an outflow or distal end 3816. When expanded, a diameter of the inflow end 3806 of the stent 3802 can be the same as a diameter of the outflow end 3816 of the stent 3802. The stent 3802 can be formed by a laser-cut manufacturing method and/or another conventional stent forming method as would be understood by one of ordinary skill in the art. The cross-section of the stent 3802 can be trapezoidal, circular, ellipsoidal, rectangular, hexagonal, square, or other polygonal shape, although at present it is believed that trapezoidal, circular or ellipsoidal may be preferable when utilized with the replacement of an aortic valve. Similarly, the cross-section of the various struts that form the stent 3802 may be circular, ellipsoidal, rectangular, hexagonal, square, trapezoidal, wedge-shaped, or other polygonal shape. FIG. 38C shows an open, flat view of an example of the stent 3802 with a circular or ellipsoidal example of the unitary frame.

A prosthetic valve (not shown) is disposed within and secured to at least the transition portion 3824 of the stent 3802. In addition, the prosthetic valve can also be disposed within and secured to the inflow portion 3808 of the stent 3802 and/or the outflow portion 3818 of the stent 3802. One skilled in the art will realize that the prosthetic valve can be disposed within and secured to one or more of the inflow portion 3808, outflow portion 3818, or the transition portion 3824, for example, depending on the design and construction of the prosthetic valve and/or the design and construction of the stent 3802. The prosthetic valve is the same as prosthetic valve 132 described above.

The inflow portion 3808 can be formed proximate to the inflow end 3806 of the stent 3802. The inflow portion 3808 of the stent 3802 may be formed with crowns 3810, struts 3812, and nodes 3811 formed at an intersection of pairs of struts 3812. The inflow end 3806 of the tubular stent 3802 can include a total of twelve endmost inflow crowns 3810A. Pairs of the struts 3812, coupled at the nodes 3811, form cell 3813 that define an open space in the stent 3802.

The outflow portion 3818 can be formed proximate to the outflow end 3816 of the stent 3802. The outflow portion 3818 can be configured in a shape that forms a central lumen or passageway, for example, a ring. The outflow portion 3818 can include a plurality of crowns 3820 and a plurality of struts 3822 with each crown 3820 being formed between a pair of opposing struts 3822. Each crown 3820 can be a curved segment or bend extending between opposing struts 3822. A series of endmost outflow crowns 3820A are formed at the outflow end 3816 of the stent 3802. For example, the outflow end 3816 of the stent 3802 can have a total of six endmost outflow crowns 3820A. In an embodiment hereof, the total of the endmost inflow crowns 3810A are twice a total of the endmost outflow crowns 3820A.

The transition portion 3824 bridges, connects, or otherwise extends between the inflow portion 3808 and the outflow portion 3818. The transition portion 3824 can includes a minimum of three axial frame members 3826, each axial frame member 3826 extending between an outflow crown 3820 of the outflow portion 3818 and a crown 3810 of the inflow portion 3808. Each axial frame member 3826 can be connected to a crown 3820 of the outflow portion 3818 and connected to a crown 3810 of the inflow portion 3808. The axial frame members 3826 can be substantially parallel to the central longitudinal axis of the stent 3802. Each axial frame member 3826 can be disposed approximately halfway between a pair of adjacent endmost outflow crowns 3820A. While the stent 3824 has been described as including a transition portion 3824, one skilled in the art will realize that the transition portion 3824 may form a portion of the inflow portion 3808 and/or the outflow portion 3818.

In an embodiment, the transition portion 3824 can include up to six axial frame members 3826, with three of the axial frame members 3826 being commissure posts 3826A and three of the axial frame members 3826 being axial struts 3826B being alternatingly positioned, as illustrated, for example, in FIG. 38C. The commissure posts 3826A can be circumferentially spaced apart and aligned with and attached to a respective commissure of the three leaflets of the prosthetic valve, and the axial struts 3826B can be disposed between adjacent commissure posts 3826A. The axial frame members 3826 aid in valve alignment and coaptation. More particularly, the axial frame members 3826 reinforce or strengthen the commissure region of the prosthetic valve by shaping the leaflets and supporting the leaflets during opening and closing thereof, and thus provide more reliable leaflet coaptation. In addition, the axial frame members 3826 maximize symmetrical cell expansion.

In this embodiment, the endmost outflow crowns 3820A are not connected to the axial frame members 3826 but rather may be considered to be free or unattached while the remaining outflow crowns 3820 of the outflow portion 3818 are connected to the axial frame members 3826 and disposed closer to the inflow end 3806 than the endmost outflow crowns 3820A. In the embodiment shown, the stent 3802 includes a single row of struts 3822 and crowns 3820 coupled to the axial frame members 3826 and defining the outflow end 3816 of the stent 3802. Further, in the embodiment shown, exactly two struts 3822 and a single crown 3820 of the outflow portion 3818 are disposed between adjacent axial frame members 3826. Such an arrangement can provide a series of six endmost cells 3825 formed at the outflow portion 3818 of the stent 3802. Each endmost cells 3825 can define an open space in the stent 3802, which is formed in any type of shape, in the radially expanded configuration (see FIGS. 38D-38E). More particularly, each endmost cells 3825 can be defined by two adjacent struts 3822 of the outflow portion 3818, four adjacent struts 3812 of the inflow portion 3808, and two adjacent axial frame members 3826 of the transition portion 3824. The endmost cells 3825 of the outflow portion 3818 are relatively larger than the cells 3813 of the inflow portion 3808 to improve access to the coronary arteries. More particularly, the endmost cells 3825 of the outflow portion 3818 can be configured to be of sufficient size to be easily crossed with a coronary guide catheter into either the right coronary artery or the left main coronary artery once the transcatheter valve prosthesis 3800 is deployed, in situ.

In one embodiment, the inflow portion 3808 can include exactly three rows of struts 3812 and crowns 3810 between the axial frame members 3826 and the inflow end 3806 of the stent 3802. Further, in this embodiment, the four struts 3812 and three crowns 3810 can be disposed between adjacent axial frame members 3826. In an embodiment, a height or length of the stent 3802 in the expanded configuration can be between 14 and 23 mm. the height being measured from the most proximal part thereof to the most distal part thereof, and a diameter of the stent 3802 in the expanded configuration can be between 18 and 31 mm. For example, an expanded 21 mm diameter device would be 15 mm in height. An expanded 30 mm diameter device would have a 21 mm height. One skilled in the art will realize that the above configuration of the inflow portion 3808 is one example of a configuration of the inflow portion 3808 and that the inflow portion 3808 can include fewer or additional rows of struts 3812 and crowns 3810. Likewise, one skilled in the art will realize that each row can include fewer or additional numbers of struts 3812 and crowns 3810. Additionally, one skilled in the art will realize that the ranges of the height and diameter of the stent 3802 are examples and that the height and diameter of the stent 3802 may vary based on an amount of expansion of the stent 3802, for example, as required by a given application and/or governed by the design and construction of the stent 3802.

The lengthened commissure posts 3826A of the stent 3802 will now be described in more detail. The axial frame members 3826 include lengthened commissure posts 3826A that are formed to have an axial length greater than the axial struts 3826B. Each lengthened commissure posts 3826A extends into the outflow portion 3818 of the stent 3802 to allow for lengthened commissure posts without increasing the overall height of the transcatheter valve prosthesis 3800. More particularly, each axial struts 3826B is an axial segment having a first end connected to a crown 3820 of the outflow portion 3818 and a second end 3838 connected to a crown 3810 of the inflow portion 3808. Stated another way, a crown 3820 of the outflow portion 3818 may be considered the outflow end of each axial strut 3826B and a crown 3810 of the inflow portion 3808 may be considered the inflow end of each axial strut 3826B. Conversely, each lengthened commissure posts 3826A is a relatively stiff, axial segment or planar bar having a first end 3872 connected to a crown 3810 of the inflow portion 3808 while a second, unattached or free end 3874 of each of the lengthened commissure posts 3826A is disposed within the outflow portion 3818. Stated another way, a crown 3810 of the inflow portion 3808 may be considered the inflow end of each commissure post 3826A such that each commissure post 3826A extends from struts 3812 of the inflow portion 3808 to the outflow end thereof, which is the unattached or free end 3874 thereof. Because the lengthened commissure posts 3826A are longer than the axial struts 3826B, struts 3822 of the outflow portion 3818 intersect the lengthened commissure posts 3826A at a central or mid-portion 3855 thereof. The location of the connection between struts 3822 of the outflow portion 3818 to the mid-portions 3855 of the lengthened commissure posts 3826A is spaced a distance, in the direction of the inflow end 806, from the unattached or free end 3874 of the lengthened commissure posts 3826A. As such, a first or transition portion 3854A of each lengthened commissure post 3826A is disposed in the transition portion 3824 of the stent 3802 between the mid-portion 3855 and a crown 3810 of the inflow portion 3808 while an second or outflow portion 3854B of each lengthened commissure post 3826A is disposed in the outflow portion 3818 of the stent 3802 between the mid-portion 3855 and the unattached or free end 3874.

The outflow portions 3854B function as support features that allow for lengthened commissure posts 3826A to further reinforce or strengthen the commissure region of the transcatheter valve prosthesis 3800. Each outflow portion 3854B extends into the outflow portion 3818 of the stent 3802 to allow for lengthened commissure posts 3826A without increasing the overall height of the transcatheter valve prosthesis 3800. In an embodiment, the stent 3802 can include a total of three lengthened commissure posts 3826A. The lengthened commissure posts 3826A extend substantially parallel to the central longitudinal axis of the stent 3802 and are circumferentially spaced apart from each other. The lengthened commissure posts 3826A may include holes or openings 3871 formed therein configured to attach a respective commissure of the three leaflets of the prosthetic valve to the stent 3802. Additionally, in some embodiments, the lengthened commissure posts 3826A may include one or more holes or openings to support alignment markers, as described further below. One skilled in the art will realize that the above configuration of the outflow portion 3818 is one example of a configuration of the outflow portion 3818 and that the outflow portion 3818 can include fewer or additional numbers of commissure posts 3826A, axial struts 3826B, crowns 3820, and struts 3822.

The lengthened commissure posts 3826A reduce stresses observed at the commissure region during valve loading by spreading out such stresses across a larger area. More particularly, as compared to self-expanding valve stents, balloon expandable valves stents are stiffer and stronger but therefore may place more stress on the valve leaflets attached thereto attached to the stent 3802. The valve leaflets, which are often formed from tissue, are more durable when the portion of the stent to which they are attached is more flexible, but such stent flexibility may be detrimental to stent fatigue. As such, the lengthened commissure posts 3826A achieve a balance between stent durability and tissue durability because the stent 3802 maintains its strength and durability while the lengthened commissure posts 3826A improve or increase tissue durability of the valve leaflets attached thereto by stress relief from the lengthened commissure posts.

Further, the performance of the transcatheter valve prosthesis 3800 is enhanced by the lengthened commissure posts 3826A without increasing the overall height of the transcatheter valve prosthesis 3800. Notably, each lengthened commissure posts 3826A does not extend beyond the endmost outflow crowns 3820A of the outflow portion 3818. For example, in the unexpanded or compressed state illustrated in FIG. 38A, the outflow portions 3854B of the lengthened commissure posts 3826A extend into the outflow portion 3818, but do not extend beyond the endmost outflow crowns 3820A. In the expanded or uncompressed state illustrated in FIG. 38D, the outflow portions 3854B of the lengthened commissure posts 3826A extend into the outflow portion 3818, but do not extend beyond the endmost outflow crowns 3820A. Stated another way, the height of each lengthened commissure posts 3826A is not greater than the height of the endmost outflow crowns 3820A and the overall height of the transcatheter valve prosthesis 3800 is not increased by the addition of the outflow portions 3854B. Further, since each outflow portion 3854B is disposed on the outflow side of outflow crowns 3820, the outflow portions 3854B lengthen the commissure posts without making the transition portion 3824 of the stent 3802 longer. In other words, the commissure posts could alternatively be lengthened along the transition portion 3824, but such additional length along the transition portion 3824 would undesirably increase the overall length of the transcatheter valve prosthesis 3800. Thus, the outflow portions 3854B result in longer commissure posts without adding overall height. A relatively short or minimized overall height is desirable to increase coronary access and improve system deliverability.

In another embodiment hereof (not shown), the axial struts 3826B of the stent 3802 may also be lengthened to include an outflow portion similar to outflow portion 3854B of the lengthened commissure posts 3826A. Lengthening the axial struts 3826B in addition to the lengthened commissure posts 3826A may aid in valve alignment and coaptation. Symmetrical cell expansion ensures that the stent crimps well onto a balloon of a balloon catheter for delivery. Poor crimp quality may lead to portions of the stent overlapping when crimped, which in turn may cause tissue damage to the valve leaflets of the prosthetic valve during the crimping process.

In embodiments, to ensure the proper placement in the native anatomy of a subject, the transcatheter valve prosthesis 3800 can include the one or more inflow markers 3860 and the first outflow marker 3870. In embodiments, the inflow markers 3860 can be positioned towards the inflow end 3806 of the stent 3802 in the inflow portion 3808. As illustrated in FIG. 38C, the stent 3802 can include three rows of the struts 3812: a first row 3840 of the struts 3812 formed proximate to the inflow end 3806, a second row 3842 of the struts 3812 formed between the first row 3842 and a third row 3844, and the third row 3844 of struts 3812 formed proximate to the transition portion 3824. In an embodiment, the inflow markers 3860 can be positioned at the intersection 3846 of the first row 3840 and the second row 3842. For example, as illustrated in FIG. 38C, the inflow markers 3860 can be positioned at every other intersection of a pair of the struts 3812 of the first row 3840 and the second row 3842. The inflow markers 3840 are circumferentially aligned with each other around a circumference of the stent 3802.

While FIG. 38C illustrates one example of the positioning and number of inflow markers 3860, one skilled in the art will realize that the stent 3802 can include any number of inflow markers 3860, positioned at any location within the inflow portion 3808. For example, the inflow markers 3860 can be portioned on the struts 3812. Likewise, for example, the inflow markers 3860 can be asymmetrically aligned, circumferentially, around a circumference of the stent 3802, e.g., with different circumferential distances between the inflow markers 3860. Additionally, for example, the inflow markers 3860 can be positioned at different distances from the inflow end 3806.

In embodiments, the inflow markers 3860 can be formed in any shape to assist in the alignment of the transcatheter valve prosthesis 3800. In embodiments, as illustrated in FIGS. 38A-38E, the inflow markers 3860 can be formed having a circular cross-sectional shape. In other embodiments, the inflow markers 3860 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the inflow markers 3860 may be provided to provide a benefit for a given application.

In embodiments, the inflow markers 3860 include radiopaque or other material that allow the inflow markers 3860 to be detected and/or viewed during the installation of the transcatheter valve prosthesis 3800. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc.

In embodiments, the inflow markers 3860 can be attached to the stent 3802 within a containment member 3862. The containment member 3862 can be configured as a hollow structure or opening in the stent 3802 which can receive the inflow markers 3860. In an embodiment, the containment member 3862 can be open to the interior and exterior of the stent 3802, thereby allowing the inflow markers 3860 to be exposed to the interior and exterior of the stent 3802 and increasing visibility at multiple angles. In some embodiments, the containment member 3862 can be open only to the interior or exterior of the stent 3802, thereby forming a cavity or depression in the stent 3802.

The containment member 3862 can be configured in a shape that matches a shape of the inflow markers 3860. For example, as illustrated in FIGS. 38A-38C, if the inflow markers 3860 have a circular cross-sectional shape, the containment member 3862 can be define a cavity that is circular, e.g., a hollow ring. In some embodiments, the containment member 3862 need not extend from an exterior or an interior of the stent 3802 such that the containment member 3862 includes a surface aligned with the exterior surface or interior surface of the stent 3802. In some embodiments, the containment member 3862 may extend from an exterior or an interior surface of the stent 3802.

In some embodiments, when placed in the containment member 3862, one or more the inflow markers 3860 may be contained within the containment member 3862 and may be recessed from an exterior and/or an interior surface of the stent 3802. In some embodiments, when placed in the containment member 3862, one or more the inflow markers 3860 may be contained within the containment member 3862 and may be flush with an exterior and/or an interior surface of the stent 3802. In some embodiments, when placed in the containment member 3862, one or more the inflow markers 3860 may be extend from the containment member 3862 and may be extend from an exterior and/or an interior surface of the stent 3802.

In embodiments, the inflow marker 3860 can be attached to, positioned in, and/or formed in the containment member 3862 utilizing any type of processes and/or procedure. In an embodiment, radiopaque beads or spheres (or lines of radiopaque beads or spheres) may be press fit, swaged, interference fit, etc. into the containment member 3862. In an embodiment, the stent 3802 may not include a containment member 3862. In this embodiment, the inflow markers 3860 may be attached and/or applied to the stent 3802. For example, the inflow markers 3860 may comprise radiopaque bands that are attached to the stent 3802. Likewise, for example, the inflow markers 3860 may be formed by applying radiopaque materials to the stent 3802 in any shape. One skilled in the art will realize that the inflow markers 3860 may be attached to or formed on the stent 3802 utilizing any processes as required by the design of the stent 3802 and/or application of the transcatheter valve prosthesis 3800.

In any embodiment, the inflow markers 3860 can be formed to dimensions such that the inflow markers 3860 do not affect the operation of the transcatheter valve prosthesis 3800. For example, the inflow markers 3860 can be formed to not extend beyond the exterior diameter of the stent 3802 or extend into the central lumen of the stent 3802, e.g., having a radial depth that is equal to or less than the radial depth of the struts 3812. In an embodiment, the inflow markers 3860 can have a circular cross-sectional shape with a diameter ranging between approximately 0.5 mm and 1.0 mm, for example, approximately 0.8 mm. In this embodiment, the containment member 3862 can have a circular cross-sectional shape with a diameter ranging between approximately 0.5 mm and 1.0 mm, for example, approximately 0.8 mm. In another embodiment, the inflow markers 3860 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm. In this embodiment, the containment member 3862 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm.

In embodiments, the stent 3802 can include any number of the inflow markers 3860. In an embodiment, the stent 3802 can include one or more inflow markers 3860 positioned at different locations of the intersection 3846 of the first row 3840 of struts 3812 and the second row 3842 of the struts 3812. In another embodiment, the stent 3802 can include six (6) inflow markers 3860 positioned at alternating locations of the intersection 3846 of the first row 3840 of struts 3812 and the second row 3842 of struts 3812. In the embodiment, the inflow markers 3860 form a ring of distinct marker points around the circumference of the stent 3802, wherein each distinct marker point is equal distance from the inflow end 3806. One skilled in the art will realize that the stent 3802 may include any number of the inflow markers 3860, which are positioned at any location within the inflow portion 3808. The inflow markers 3860 are preferably located at the lengthwise location of the stent 3802 that is desired to be aligned with the annulus of the native heart valve when the transcatheter valve prosthesis 3800 is deployed at the native heart valve. For example, inflow markers 3860 allows for better depth positioning of the transcatheter valve prosthesis 3800, in a crimped or compressed state, such that it can be more accurately deployed and reduce the incidence rate of permanent pacemaker (PPM) post-implantation.

In embodiments, the transcatheter valve prosthesis 3800 can also include the first outflow marker 3870 to assist with the alignment of the commissure posts 3826A. The first outflow marker 3870 can operate to assist in rotational orientation of the stent 3802, as described below. Additionally, the first outflow marker 3870 can operate as a guide for determining a front or rear location the first outflow marker 3870 in 2D image during implantation, as described below. The first outflow marker 3870 can be positioned towards the outflow end 3816 of the stent 3802 in the outflow portion 3818 or the transition portion 3824.

In an embodiment, the first outflow marker 3870 can be circumferentially aligned with one of the inflow markers 3860, as illustrated in FIG. 38A or 38B. In an embodiment, the first outflow marker 3870 can be positioned on one of the outflow portions 3854B of a commissure post 3826A in the outflow portion 3818. As illustrated in FIGS. 38A and 38D, the first outflow marker 3870 can be attached to the stent 3802 within a containment member 3872 formed in one of the outflow portions 3854. In embodiments, the first outflow marker 3870 can be attached to the outflow portion 3854B within a containment member 3872. The containment member 3872 can be configured as a hollow structure or opening in the outflow portion 3854B which can receive the first outflow marker 3870.

In another embodiment (not shown), the first outflow marker 3870 can be attached to an exterior surface of the commissure post 3856A at a location that does not affect the operation of the transcatheter valve prosthesis 3800. For example, the first outflow marker 3870 can be attached to a top surface of the outflow portion 3854, proximal to the outflow end 3816. In this example, the first outflow marker 3870 can be configured not to extend beyond the exterior diameter of the stent 3802 or extend into the central lumen of the stent 3802, e.g., having a radial depth that is equal to or less than the radial depth of the outflow portion 3854.

In another embodiment, the first outflow marker 3870 can be positioned on the commissure posts 3826A. As illustrated in FIGS. 38B, 38C, and 38E, the first outflow marker 3870 can be attached to the stent 3802 within a containment member 3872 formed in a commissure post 3826A. In this embodiment, the containment member 3872 can be positioned at any location along the commissure post 3826A, for example, proximal to the outflow portion 3854, in the center of the commissure post 3826, biased towards the inflow end 3806, or at any location with the transition portion 3824, and the like.

In any embodiment, the containment member 3872 can be configured in a shape that matches a shape of the first outflow marker 3870. For example, as illustrated in FIGS. 38A-38E, if the first outflow marker 3870 have a circular cross-sectional shape, the containment member 3872 can be define a cavity that is circular, e.g., a hollow ring. In some embodiments, the containment member 3872 need not extend from an exterior or an interior of the outflow portion 3854B and/or any location on the commissure post 3826A such that the containment member 3872 includes a surface aligned with the exterior surface or interior surface of the stent 3802. In some embodiments, the containment member 3872 may extend from an exterior or an interior surface of the outflow portion 3854B and/or any location on the commissure post 3826A. In some embodiment, the containment member 3872 can be open to the interior and exterior of the stent 3802, thereby allowing the first outflow marker 3870 to be exposed to the interior and exterior of the stent 3802 and increasing visibility at multiple angles. In some embodiments, the containment member 3872 can be open only to the interior or exterior of the stent 3802, thereby forming a cavity or depression in the outflow portion 3854.

In some embodiments, when placed in the containment member 3872, the first outflow marker 3870 may be contained within the containment member 3872 and may be recessed from an exterior and/or an interior surface of the outflow portion 3854B and/or any location on the commissure post 3826A. In some embodiments, when placed in the containment member 3872, the first outflow marker 3870 may be contained within the containment member 3872 and may be flush with an exterior and/or an interior surface of the outflow portion 3854B and/or any location on the commissure post 3826A. In some embodiments, when placed in the containment member 3872, the first outflow marker 3870 may be extend from the containment member 3872 and may be extend from an exterior and/or an interior surface of the outflow portion 3854B and/or any location on the commissure post 3826A.

In any embodiment, the first outflow marker 3870 can be attached to, positioned in, and/or formed in the containment member 3872 utilizing any type of processes and/or procedure. In an embodiment, radiopaque beads or spheres (or lines of radiopaque beads or spheres) may be press fit, swaged, interference fit, etc. into the containment member 3872. In any embodiment, the stent 3802 may not include a containment member 3872. In this embodiment, the first outflow marker 3870 may be attached and/or applied to the outflow portion 3854B and/or any location on the commissure post 3826A. For example, the first outflow marker 3870 may comprise radiopaque bands that are attached to the outflow portion 3854B and/or any location on the commissure post 3826A. Likewise, for example, the first outflow marker 3870 may be formed by applying radiopaque materials to the outflow portion 3854B and/or any location on the commissure post 3826A in any shape. One skilled in the art will realize that the first outflow marker 3870 may be attached to or formed on the stent 3802 utilizing any processes as required by the design of the stent 3802 and/or application of the transcatheter valve prosthesis 3800.

In any embodiment, the first outflow marker 3870 can be formed in any shape to assist in the alignment of the transcatheter valve prosthesis 3800. In embodiments, as illustrated in FIGS. 38A-38C, the first outflow marker 3870 can be formed in a circular cross-sectional shape. In other embodiments, the first outflow marker 3870 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the outflow marker may be provided to provide a benefit for a given application.

In any embodiment, the first outflow marker 3870 include radiopaque or other material that allow the first outflow marker 3870 to be detected and/or viewed during the installation of the transcatheter valve prosthesis 3800. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc.

In any embodiment, the first outflow marker 3870 can be formed to dimensions such that the first outflow marker 3870 does not affect the operation of the transcatheter valve prosthesis 3800. For example, the first outflow marker 3870 can be formed to not extend beyond the exterior diameter of the stent 3802 or extend into the central lumen of the stent 3802, e.g., having a radial depth that is equal to or less than the radial depth of the commissure post 3826A. In an embodiment, the first outflow marker 3870 can have a circular cross-sectional shape with a diameter ranging between approximately 0.5 mm and 1.0 mm, for example, approximately 0.8 mm. In this embodiment, the containment member 3872 can have a circular cross-sectional shape with a diameter ranging between approximately 0.5 mm and 1.0 mm, for example, approximately mm. In another embodiment, the first outflow marker 3870 can have an elliptical cross-sectional shape with an axial diameter ranging between approximately 0.5 mm and 1.0 mm, for example, approximately 0.8 mm, and a circumferential diameter ranging between approximately mm and 1.0 mm, for example, approximately 0.9 mm. In this embodiment, the containment member 3872 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm.

Figure 39C:
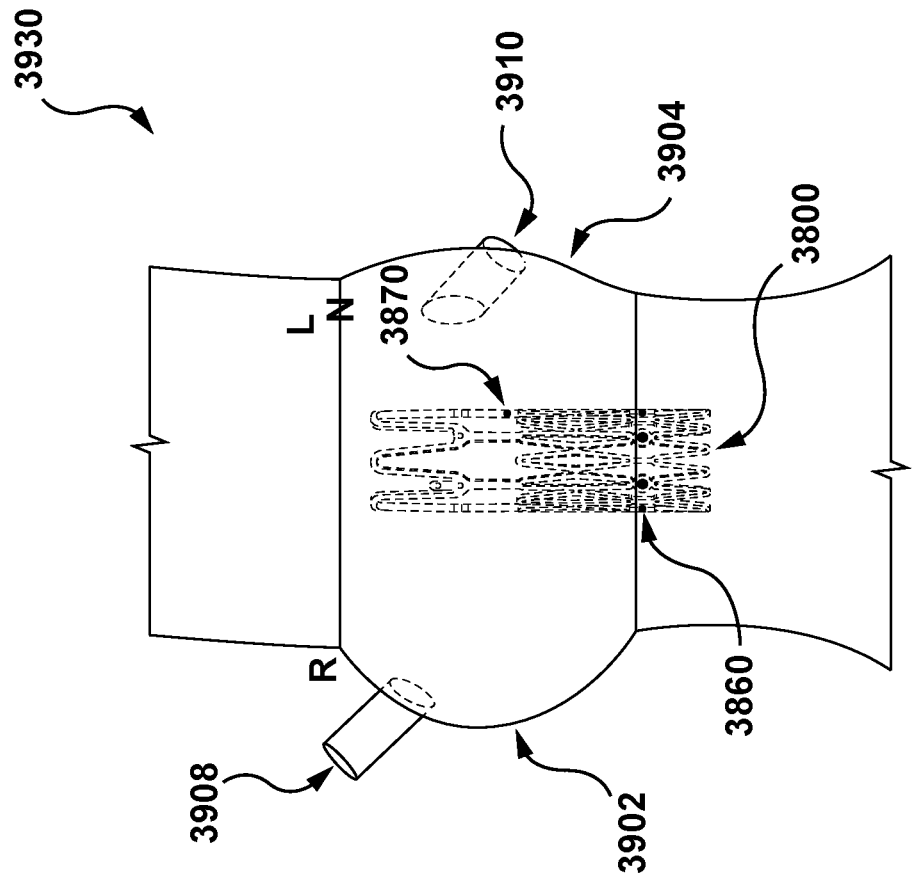

In embodiments, the inflow markers 3860 and the first outflow marker 3870 can be utilized in orientation (e.g., axial/annular alignment, tilt alignment, circumferential (rotational) alignment, etc.) of the transcatheter valve prosthesis 3800, in situ, during installation as described below with reference to FIGS. 39A-39E. FIGS. 39A-39C illustrate various views of a target site, e.g., an aortic heart valve, of the transcatheter valve prosthesis 3800. As illustrated in FIG. 39A, which is an annular view of the target site taken perpendicular to an annulus 3901, the target site includes three valve cusps of the aortic root, the right coronary cusp 3902, the left coronary cusp 3904 and the non-coronary cusp 3906. The region of the right coronary cusp 3902 includes ostia of the right coronary artery 3908. Likewise, the region of the left coronary cusp 3904 includes ostia of the left main coronary artery 3910.

When installing the transcatheter valve prosthesis 3800, it is desirable to properly align the stent 3802 within the target site. For example, the transcatheter valve prosthesis 3800 needs to be properly aligned, axially/annularly, so that the transcatheter valve prosthesis 3800 properly engages the native leaflets/tissue of the target site, e.g., the aortic annulus without causing conduction blockages by implanting too deep or causing an embolization of the transcatheter valve prosthesis 3800 because it was implanted too high. Likewise, the transcatheter valve prosthesis 3800 needs to be aligned circumferentially or rotationally. When being positioned, in situ, it is very important to avoid blocking the ostia of the right coronary artery 3908 and/or the left main coronary artery 3910. Proper circumferential or rotational orientation within the target site reduces the risk of blocking coronary access.

As illustrated in FIG. 39A, the right coronary cusp 3902, the left coronary cusp 3904, and the non-coronary cusp 3906 include commissure regions: right/left commissure 3920, right/non-coronary commissure 3922, and left/non-coronary commissure 3924. FIG. 39B illustrates a 2-D side view of the target site taken in an image plane 3932 (represented as a line in FIG. 39A). The image plane 3932 is approximately perpendicular to an image plane 3930 (represented as a line in FIG. 39A) in an x-direction and y-direction, and the image plane 3932 extends in the z-direction (a direction normal to the 2D view of FIG. 39A). FIG. 39C illustrates a 2-D side view of the target site taken in the image plane 3930. The image plane 3930 approximately bisects the right coronary cusp 3902 in the x-direction and y-direction (e.g., approximately perpendicular to the image plane 3932) and extends in the z-direction.

Figure 39F:
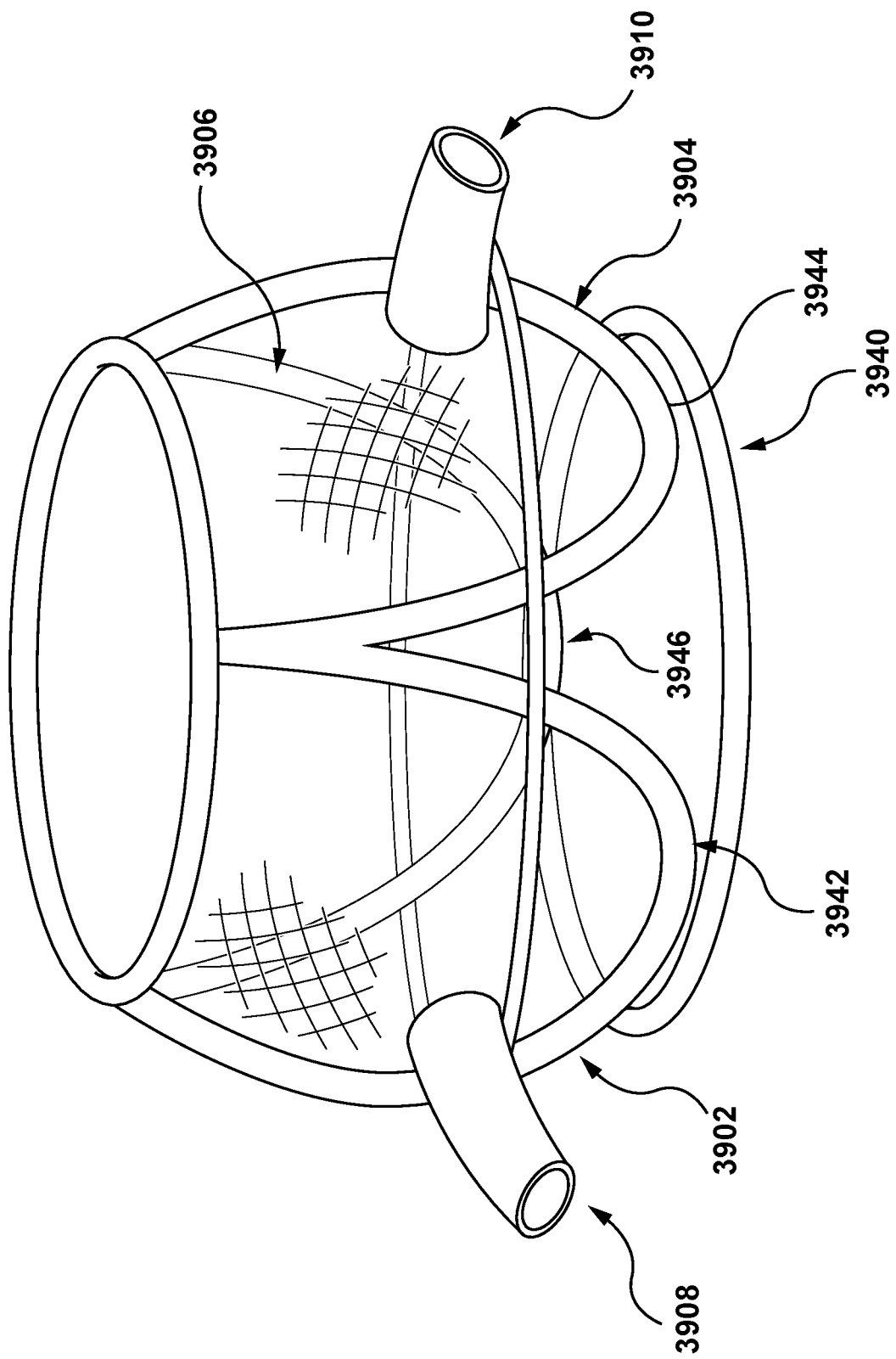

As illustrated in FIG. 39B, the inflow markers 3860 can be utilized to axially align the stent 3802 with features in the target site, e.g., basal plane 3940 of the right coronary cusp 3902, the left coronary cusp 3904 and the non-coronary cusp 3906. For example, as illustrated in FIG. 39F, which is a three dimension view of the target site, the basal plane 3940 can be defined as a plane that intersects a nadir 3942 of the right coronary cusp 3902, a nadir 3944 of the left coronary cusp 3904, and a nadir 3946 of the non-coronary cusp 3906. To align the transcatheter valve prosthesis 3800, the stent 3802, a delivery system (not shown) can be manipulated (e.g., advanced, retracted, etc.) until the inflow markers 3860 align with the basal plane 3940, as illustrated in FIG. 39B. As such, the transcatheter valve prosthesis 3800 can be positioned at a proper depth within the target site, thereby ensuring proper engagement with the native tissue.

Additionally, the inflow markers 3860 can be utilized to align the tilt and/or rotation of the stent 3802. For example, to align the transcatheter valve prosthesis 3800, the stent 3802, the delivery system can be manipulated (e.g., rotated, tilted, etc.) until the inflow markers 3860 form a predetermined pattern visible in the image captured in the image plane 3930 and/or 3932. For example, as illustrated in FIGS. 39D and 39E, the stent 3802 may include six (6) inflow markers 3860. As the stent 3802 is rotated, different numbers of the inflow markers 3860 may be visible in the 2D image, e.g., 6 markers in image 2 and 6 markers in image 3. In this example, to align the transcatheter valve prosthesis 3800, the delivery system can be manipulated (e.g., rotated, tilted, etc.) until all 6 of the inflow markers 3860 form a predetermined pattern, e.g., only 3 inflow markers 3860, that is visible in the image captured in the image plane 3932. In other words, 3 of the inflow markers 3860 overlap and obscure the other 3 of the inflow markers 3860 in the 2D image. If the image plane 3932 is aligned with the native anatomy as desired, the appearance of the predetermined pattern, e.g., only 3 inflow markers 3860, indicates the transcatheter valve prosthesis 3800 is approximately perpendicular to image plane 3932 indicating proper orientation (e.g., indicating proper tilt, proper rotation, etc.) of the transcatheter valve prosthesis 3800, as shown in FIG. 39D and FIGS. 39E, image 3.

In embodiments, the first outflow marker 3870 can be utilized to align circumferential or rotational orientation of the transcatheter valve prosthesis 3800. More particularly, the first outflow marker 3870 can allow a physician to correctly interpret the circumferential orientation of the transcatheter valve prosthesis 3800 and to clock or rotate the transcatheter valve prosthesis 3800 relative to the anatomy to correct the circumferential or rotational orientation, if necessary, to avoid blocking the ostia of the right coronary artery 3908 and/or the left main coronary artery 3910. In addition, first outflow marker 3870 clocks the commissures of the transcatheter valve prosthesis 3800 so they rotationally align with the native valve commissures. Commissure to commissure alignment (transcatheter valve prosthesis 3800 commissure to native commissure) may improve transcatheter valve prosthesis 3800 hemodynamics and leaflet durability. To align the transcatheter valve prosthesis 3800, the stent 3802 can rotated, in situ, by the delivery system to be positioned in a desired circumferential or rotational alignment.

For example, to avoid blocking the ostia of the left main coronary artery 3910, the first outflow marker 3870 can be positioned on the stent 3802 such that for proper rotational orientation of the stent 3802, the first outflow marker 3870 is aligned with the left/non-coronary commissure 3924 of the left coronary cusp 3904 and the non-coronary cusp 3906. As illustrated in FIG. 39B, if viewed in the image plane 3932 (parallel to the annulus 3901 and bisecting the right coronary cusp 3902), the first outflow marker 3870 can be rotated until the first outflow marker 3870 is centered in the image, thereby indicating alignment with the left/non-coronary commissure 3924. Likewise, for example, as illustrated in FIG. 39C, if viewed in the image plane 3930 (parallel to the annulus 3901 and is perpendicular to the image plane 3932), the first outflow marker 3870 can be rotated until the first outflow marker 3870 appears in the right of the image, thereby indicating alignment with the left/non-coronary commissure 3924. This alignment ensures that the commissure post 3826A does not block the ostia of the left main coronary artery 3910. Likewise, this alignment can allow the additional commissure post 3826A to be aligned with the right/left commissure 3920 and the right/non-coronary commissure 3920. While the above describes, the first outflow marker 3870 being aligned with the left/non-coronary commissure 3924, the first outflow marker 3870 can be aligned with other structure at the target site, e.g., right/left commissure 3920, right/non-coronary commissure 3922, etc.

In embodiments, the first outflow marker 3870 can also be used as a guide to a front or rear location of the first outflow marker 3870 appearing in 2D image. That is, the first outflow marker 3870 can be utilized to determine whether the first outflow marker 3870 is positioned on a side of the stent 3802 closest to the imaging apparatus (front location) or positioned on a side of the stent 3802 furthest from the imaging apparatus (rear location). FIGS. 39D and 39E illustrate several sequential images 3960 captured in the image plane 3932 as the transcatheter valve prosthesis 3800 is rotated in different directions using a handle 3950 of the delivery system.

As illustrated in FIG. 39D and FIG. 39E, as the handle 3950 is rotated in a clockwise direction (thereby rotating the stent 3802 counter-clockwise), the first outflow marker 3870 moves in the images 3960 to the right or left depending on the front or rear location of the first outflow marker 3870. That is, based on the transcatheter approach to the target site, a tip of the delivery system may be point in a direction opposite the direction of the handle 3950 (e.g., in a direction back towards the handle 3950), thereby causing the stent 3802 to rotate in a direction opposite a direction of rotation of the handle 3950, when viewed in a 2D image. For example, as illustrated in FIG. 39D, as the handle 3950 is rotated clockwise (thereby rotating the stent 3802 counter-clockwise), the first outflow marker 3870 moves from right to left in the images 3960, thereby indicating that the first outflow marker 3870 is in the front (where an emitter of the imaging device is positioned on the front side of the stent 3802 and the detector being is on a back side of the stent 3802). As illustrated in FIG. 39E, as the handle 3950 is rotated clockwise (thereby rotating the stent 3802 counter-clockwise), the first outflow marker 3870 moves from left to right in the images 3960, thereby indicating that the first outflow marker 3870 is in the rear (on the back side of the stent 3802 relative to positioning of the imaging device). If the handle 3950 is rotated counter-clockwise (thereby rotating the stent 3802 clockwise), the above movements would be reversed, e.g., left to right movement in the images would indicate front and right to left would indicate rear. While the particular movement of the first outflow marker 3870 is discussed above in reference to transcatheter approach, one skilled in the art will realize that the relative movement of the first outflow marker 3870 may change based on a different approach.

Figure 40A:
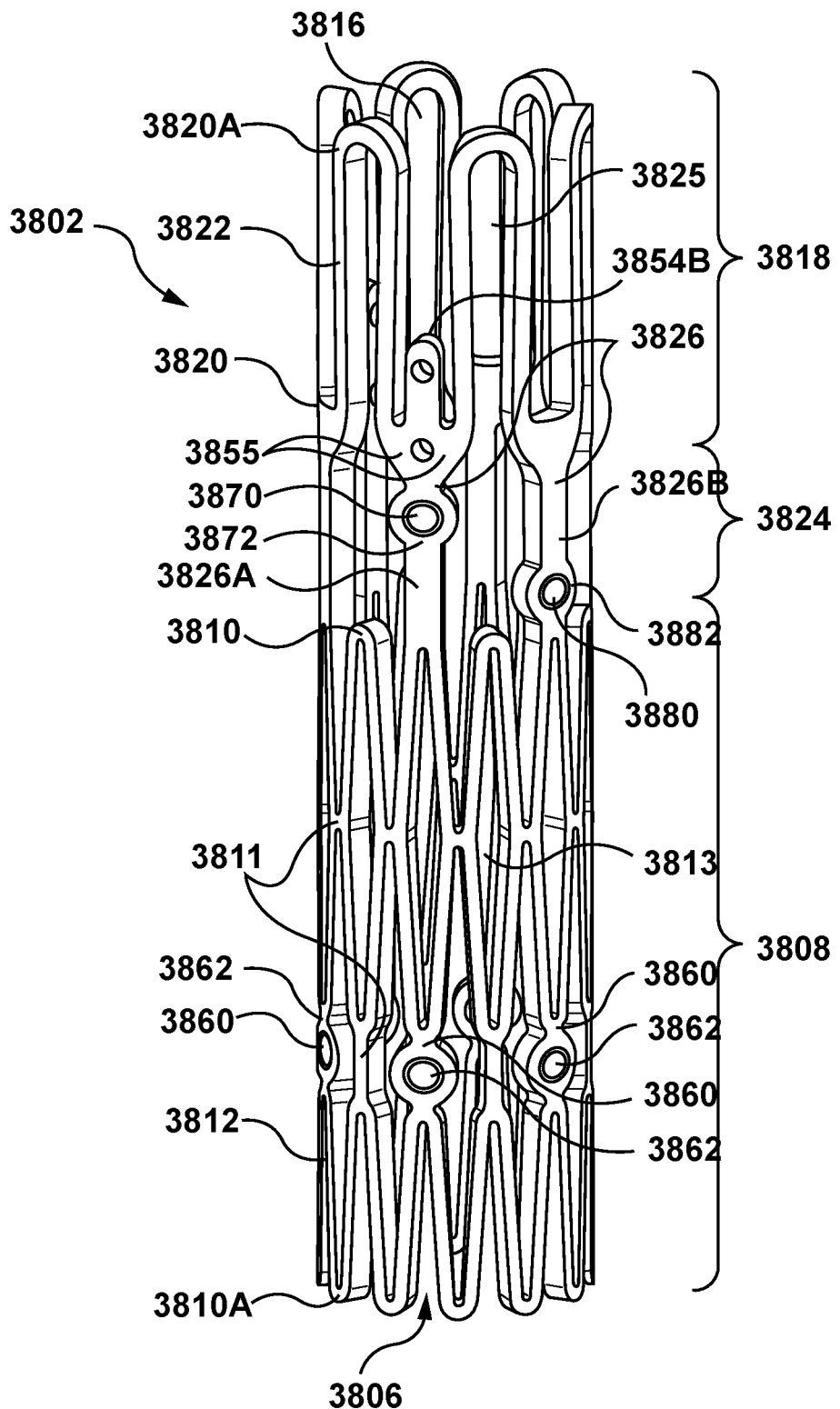
FIGS. 40A-40C illustrate another transcatheter valve prosthesis in accordance with an embodiment hereof.
Figure 40B:
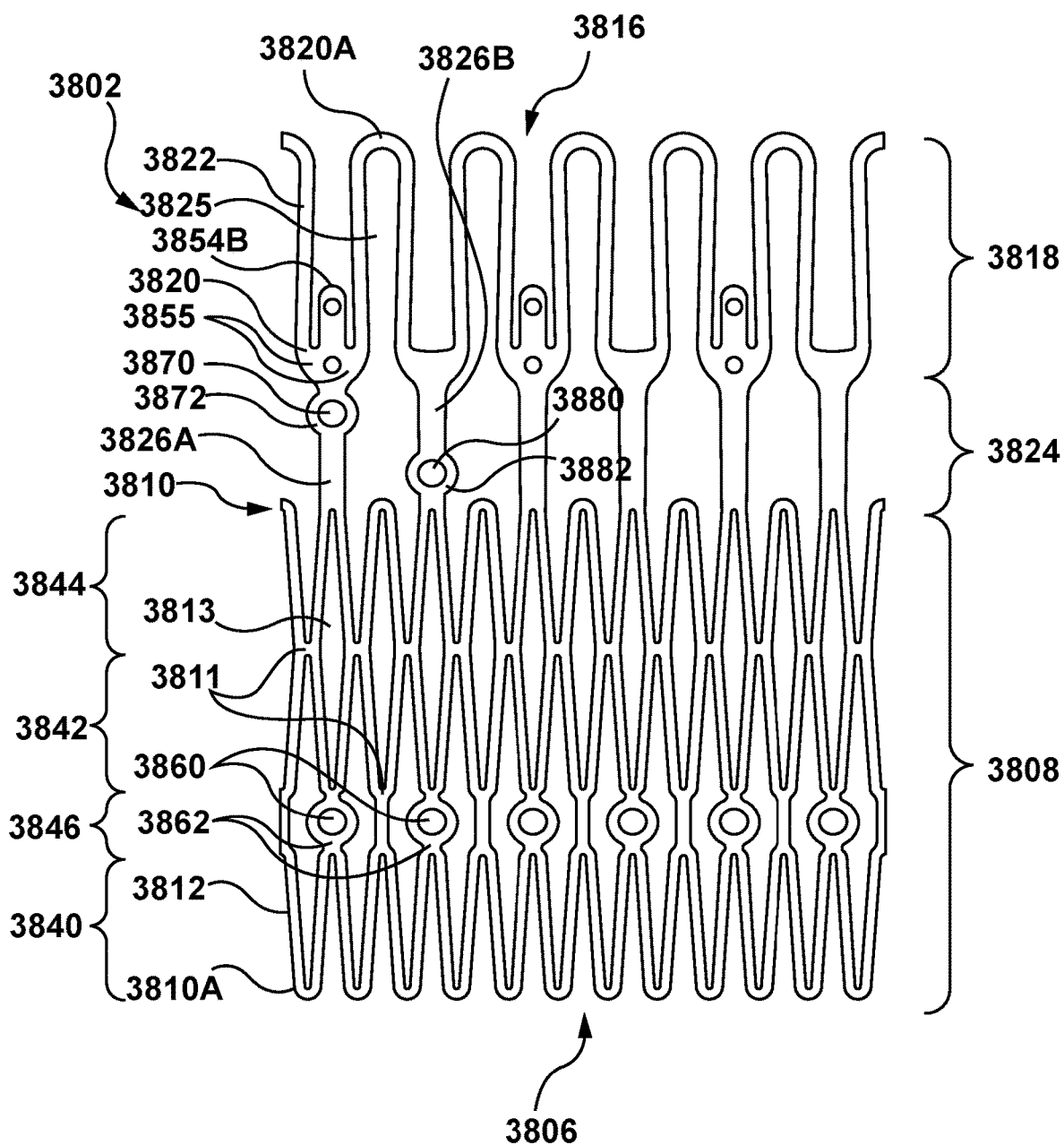
Figure 40C:
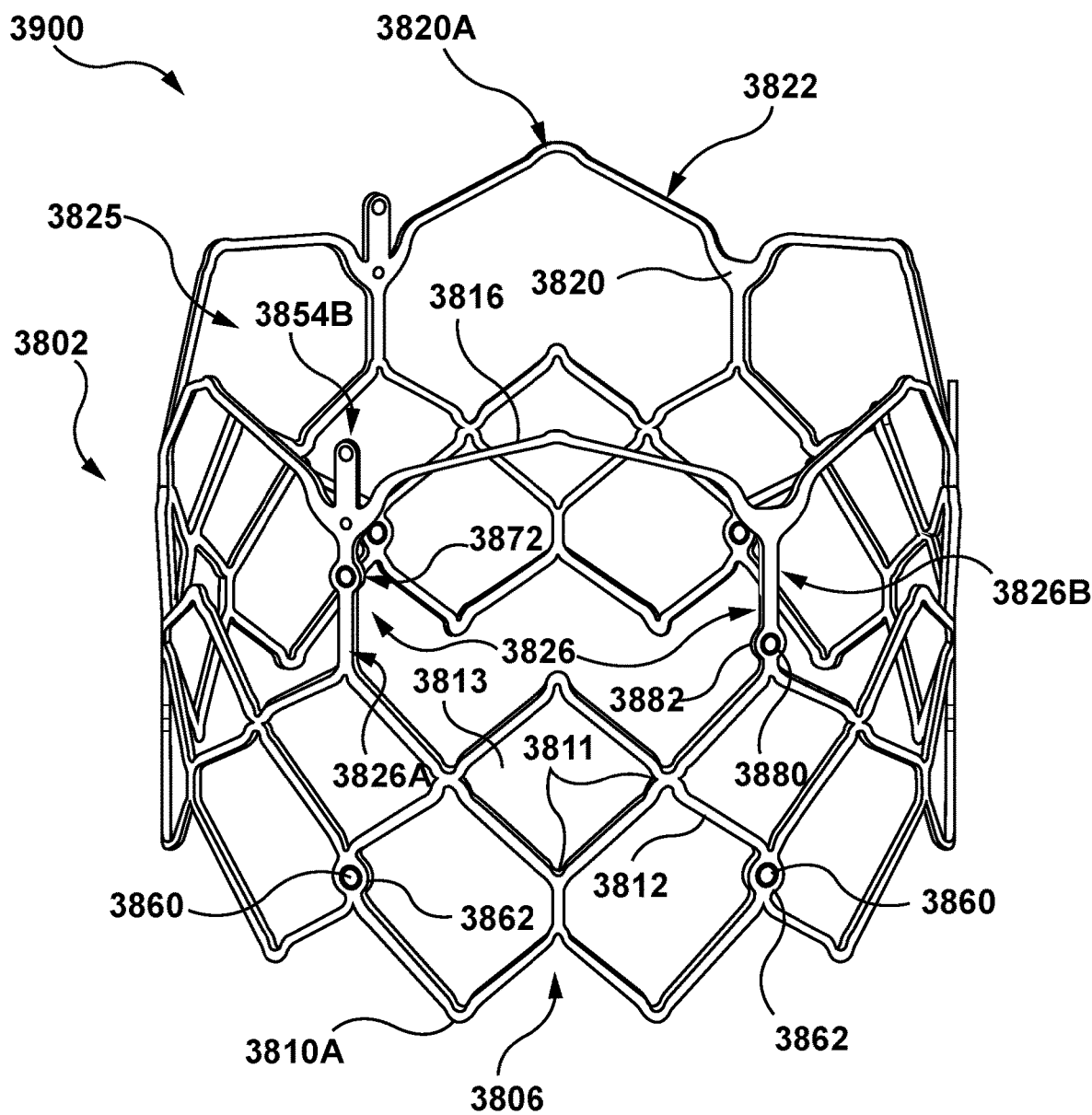

FIGS. 40A-40C illustrate a transcatheter valve prosthesis 3900 according to another embodiment herein in which a radially-expandable stent 3802 thereof includes one or more inflow markers 3860, the first outflow marker 3870, and a second outflow marker 3880. In embodiments, the inflow markers 3860, the first outflow marker 3870, and the second outflow marker 3880 can be utilized in orientation (e.g., axial/annular alignment, tilt alignment, circumferential (rotational) alignment, etc.) of the transcatheter valve prosthesis 3900, in situ, as discussed in detail below.

One skilled in the art will realize that FIGS. 40A-40C illustrate one example of an implantable medical device and that existing components illustrated in FIGS. 40A-40C may be removed and/or additional components may be added. Additionally, while the transcatheter valve prosthesis 3900 is described below as including the one or more inflow markers 3860, the first outflow marker 3870, and the second outflow marker 3880, one skilled in the art will realize that the transcatheter valve prosthesis 3900 can include additional markers, for example, any of the markers described herein. Moreover, while the one or more inflow markers 3860, the first outflow marker 3870, and the second outflow marker 3880 are described herein with respect to the transcatheter valve prosthesis 3900, one skilled in the art will realize that any embodiment of the transcatheter valve prostheses described herein can include one or more inflow markers 3860, the first outflow marker 3870, and the second outflow marker 3880.

As discussed above, the stent 3802 of the transcatheter valve prosthesis 3900 has a non-expanded or crimped, which is shown in a side view of FIG. 40A, and an expanded configuration, which is shown FIG. 40C. FIG. 40B shows an open, flat view of an example of the stent 3802 with a circular or ellipsoidal example of the unitary frame. As illustrated in FIGS. 40A-40C, the transcatheter valve prosthesis 3900 can include similar components to the transcatheter valve prosthesis 3800, a description of which can be found above in the discussion of FIGS. 38A-38E. Additionally, the transcatheter valve prosthesis 3900 can include the second outflow marker 3880. The second outflow marker 3880 can be utilized in combination with the first outflow marker 3870 to align the circumferential or rotation orientation of the stent 3802, as discussed below.

In embodiments, the second outflow marker 3880 can be positioned on an axial strut 3826B. In an embodiment, the second outflow marker 3880 can be positioned on an axial strut 3826B that is adjacent (e.g., adjacent in a clockwise direction or adjacent in a counter-clockwise direction) to the commissure post 3826A containing the first outflow marker 3870. As illustrated in FIG. 40A-40C, the second outflow marker 3880 can be attached to the stent 3802 within a containment member 3882 formed in an axial strut 3826B. The containment member 3882 can be configured as a hollow structure or opening in the axial strut 3826B which can receive the second outflow marker 3880. In an embodiment, the containment member 3882 can be open to the interior and exterior of the stent 3802, thereby allowing the second outflow marker 3880 to be exposed to the interior and exterior of the stent 3802 and increasing visibility at multiple angles. In some embodiments, the containment member 3882 can be open only to the interior or exterior of the stent 3802, thereby forming a cavity or depression in the stent 3802. While the above discloses an example of the positioning of the first outflow marker 3870 and the second outflow marker 3880, one skilled in the art will realize that the first outflow marker 3870 and the second outflow marker 3880 can be positioned on any component of the outflow portion 3818 and/or transition portion 3824.

The containment member 3882 can be configured in a shape that matches a shape of the second outflow marker 3880. For example, as illustrated in FIGS. 38A-38C, if the second outflow marker 3880 have a circular cross-sectional shape, the containment member 3882 can be define a cavity that is circular, e.g., a hollow ring. In some embodiments, the containment member 3882 need not extend from an exterior or an interior of the axial strut 3826B such that the containment member 3882 includes a surface aligned with the exterior surface or interior surface of the stent 3802. In some embodiments, the containment member 3882 may extend from an exterior or an interior surface of the axial strut 3826B.

In some embodiments, when placed in the containment member 3882, the second outflow marker 3880 may be contained within the containment member 3882 and may be recessed from an exterior and/or an interior surface of the axial strut 3826B. In some embodiments, when placed in the containment member 3882, the second outflow marker 3880 may be contained within the containment member 3882 and may be flush with an exterior and/or an interior surface of the axial strut 3826B. In some embodiments, when placed in the containment member 3882, the second outflow marker 3880 may be extend from the containment member 3882 and may be extend from an exterior and/or an interior surface of the axial strut 3826B.

In embodiments, the second outflow marker 3880 can be attached to, positioned in, and/or formed in the containment member 3882 utilizing any type of processes and/or procedure. In an embodiment, radiopaque beads or spheres (or lines of radiopaque beads or spheres) may be press fit, swaged, interference fit, etc. into the containment member 3882. In an embodiment, the axial strut 3826B may not include a containment member 3882. In this embodiment, the second outflow marker 3880 may be attached and/or applied to the axial strut 3826B. For example, the second outflow marker 3880 may comprise radiopaque bands that are attached to the axial strut 3826B. Likewise, for example, the second outflow marker 3880 may be formed by applying radiopaque materials to the axial strut 3826B in any shape. One skilled in the art will realize that the second outflow marker 3880 may be attached to or formed on the axial strut 3826B utilizing any processes as required by the design of the stent 3802 and/or application of the transcatheter valve prosthesis 3900.

In any embodiment, the second outflow marker 3880 can be formed in any shape to assist in the alignment of the transcatheter valve prosthesis 3800. In embodiments, as illustrated in FIGS. 40A-40C, the second outflow marker 3880 can be formed in a circular cross-sectional shape. In other embodiments, the second outflow marker 3880 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the outflow marker may be provided to provide a benefit for a given application.

In any embodiment, the second outflow marker 3880 include radiopaque or other material that allow the second outflow marker 3880 to be detected and/or viewed during the installation of the transcatheter valve prosthesis 3900. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc.

In any embodiment, the second outflow marker 8380 can be formed to dimensions such that the second outflow marker 3880 do not affect the operation of the transcatheter valve prosthesis 3800. For example, the second outflow marker 3880 can be formed to not extend beyond the exterior diameter of the stent 3802 or extend into the central lumen of the stent 3802, e.g., having a radial depth that is equal to or less than the radial depth of the axial strut 3826B. In an embodiment, the second outflow marker 3880 can have a circular cross-sectional shape with a diameter ranging between approximately 0.5 mm and 1.0 mm, for example, approximately 0.8 mm. In this embodiment, the containment member 3882 can have a circular cross-sectional shape with a diameter ranging between approximately 0.5 mm and 1.0 mm, for example, approximately mm. In another embodiment, the second outflow marker 3880 can have an elliptical cross-sectional shape with an axial diameter ranging between approximately 0.5 mm and 1.0 mm, for example, approximately 0.8 mm, and a circumferential diameter ranging between approximately mm and 1.0 mm, for example, approximately 0.9 mm. In this embodiment, the containment member 3882 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm.

Figure 41B:
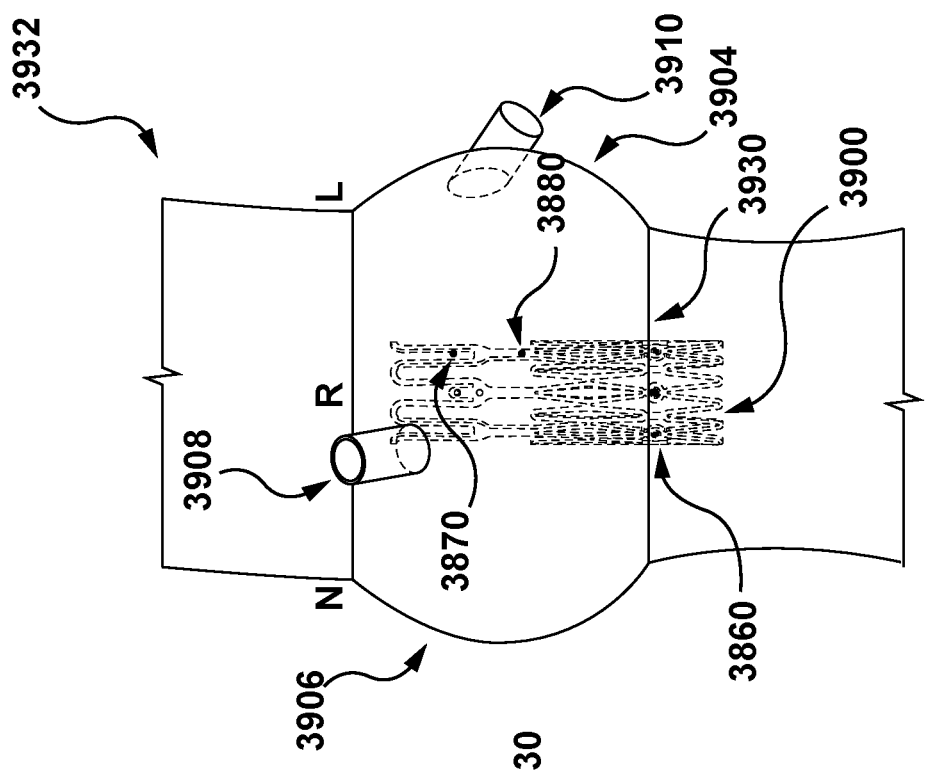
Figure 41A:
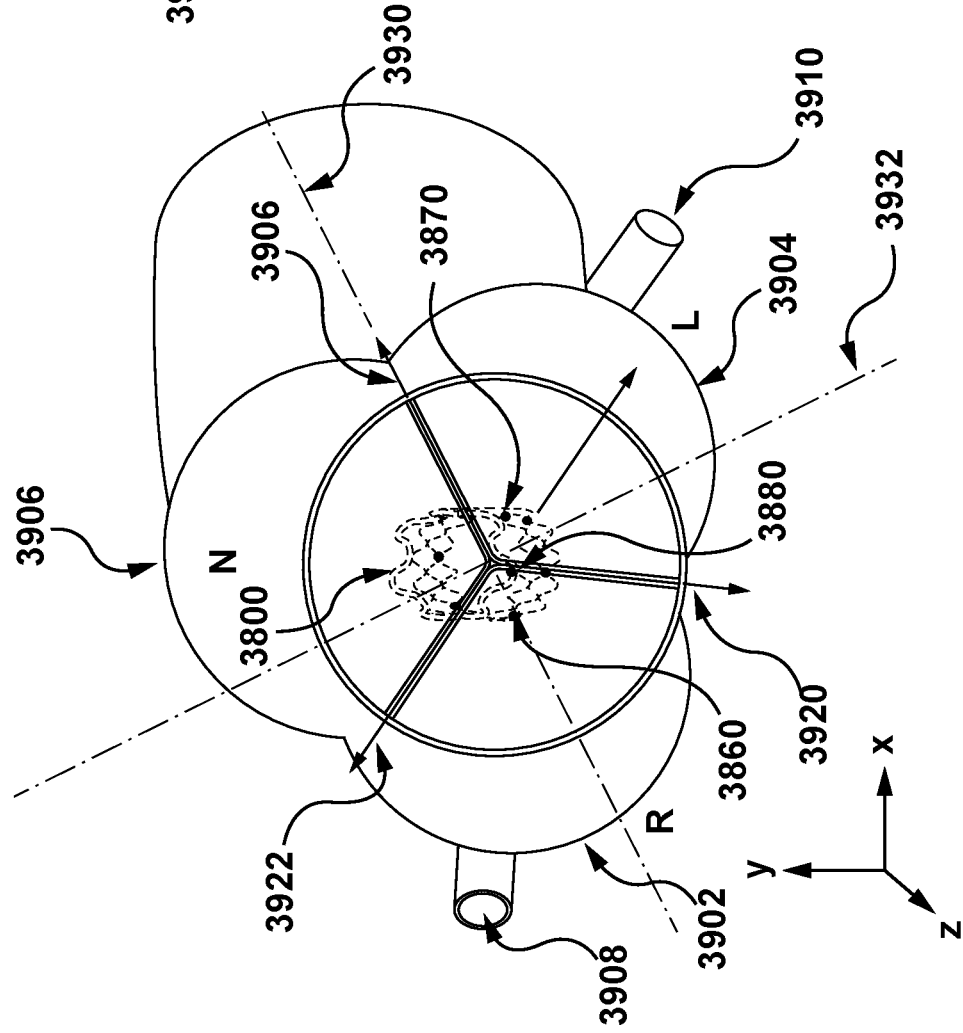

In embodiments, the inflow markers 3860, the first outflow marker 3870, and the second outflow marker 3880 can be utilized in orientation (e.g., axial/annular alignment, tilt alignment, circumferential (rotational) alignment, etc.) of the transcatheter valve prosthesis 3900, in situ, during installation as described below with reference to FIGS. 41A-41D. FIGS. 41A-41D illustrate various views of a target site e.g., an aortic heart valve, for the transcatheter valve prosthesis 3900. As illustrated in FIG. 41A, which is an annular view of the target site taken perpendicular to an annulus 3901, the target site includes three valve cusps of the aortic root, the right coronary cusp 3902, the left coronary cusp 3904 and the non-coronary cusp 3906. The region of the right coronary cusp 3902 includes ostia of the right coronary artery 3908. Likewise, the region of the left coronary cusp 3904 includes ostia of the left main coronary artery 3910.

When installing the transcatheter valve prosthesis 3900, it is desirable to properly align the stent 3802 with the target site, as discussed above. For example, the transcatheter valve prosthesis 3900 needs to be properly aligned, axially/annularly, so that the transcatheter valve prosthesis 3900 properly engages the native tissue of the target site. Likewise, the transcatheter valve prosthesis 3900 needs to be aligned circumferentially or rotationally. When being positioned, in situ, it is very important to avoid blocking the ostia of the right coronary artery 3908 and/or the left main coronary artery 3910. Proper circumferential or rotational orientation within the target site may reduce the risk of blocking coronary access and may enhance hemodynamics and valve durability because of commissure-to-commissure alignment. As illustrated in FIG. 41A, the right coronary cusp 3902, the left coronary cusp 3904, and the non-coronary cusp 3906 include commissure regions: right/left commissure 3920, right/non-coronary commissure 3922, and left/non-coronary commissure 3924. FIG. 41B illustrates a 2-D side view of the target site taken in an image plane 3932 (represented as a line in FIG. 41A). The image plane 3932 is approximately perpendicular to an image plane 3930 (represented as a line in FIG. 41A) in an x-direction and y-direction, and the image plane 3932 extends in the z-direction (a direction normal to the 2D view of FIG. 41A). FIG. 41C illustrates a 2-D side view of the target site taken in the image plane 3930. The image plane 3930 approximately bisects the right coronary cusp 3902 in the x-direction and y-direction (e.g., approximately perpendicular to the image plane 3932) and extends in the z-direction.

As illustrated in FIG. 41B, the inflow markers 3860 can be utilized to axially align the stent 3802 with features in the target site, e.g., basal plane 3940 of the right coronary cusp 3902, the left coronary cusp 3904 and the non-coronary cusp 3906. For example, as discussed above with reference to FIG. 39F, which is a three dimension view of the target site, the basal plane 3940 can be defined as a plane that intersects a nadir 3942 of the right coronary cusp 3902, a nadir 3944 of the left coronary cusp 3904, and a nadir 3946 of the non-coronary cusp 3906. To align the transcatheter valve prosthesis 3800, the stent 3802, the delivery system can be manipulated (e.g., advanced, retracted, etc.) until the inflow markers 3860 align with the basal plane 3940, as illustrated in FIG. 41B. As such, the transcatheter valve prosthesis 3800 can be positioned at a proper depth within the target site, thereby ensuring proper engagement with the native tissue.

In embodiments, as described above with reference to FIGS. 39A-39E, the first outflow marker 3870, alone, can be utilized to align circumferential or rotational orientation of the transcatheter valve prosthesis 3900. For example, the first outflow marker 3870 can be aligned to the right/left commissure 3920, right/non-coronary commissure 3922, or left/non-coronary commissure 3924, thereby aligning the commissure post 3826A to the right/left commissure 3920, right/non-coronary commissure 3922, or left/non-coronary commissure 3924, respectively. The second outflow marker 3880, alone, can similarly be utilized to align circumferential or rotational orientation of the transcatheter valve prosthesis 3900. For example, the second outflow marker 3880 can be aligned to the right/left commissure 3920, right/non-coronary commissure 3922, or left/non-coronary commissure 3924, thereby aligning the axial strut 3826B to the right/left commissure 3920, right/non-coronary commissure 3922, or left/non-coronary commissure 3924, respectively. One skilled in the art will realize that the first outflow marker 3870 and/or the second outflow marker 3880 can be aligned to any feature at the target site.

In embodiments, the combination of the first outflow marker 3870 and the second outflow marker 3880 can be utilized to align circumferential or rotational orientation of the transcatheter valve prosthesis 3900. That is, the relative appearance and/or location in a 2D image can be utilized to align circumferential or rotational orientation of the transcatheter valve prosthesis 3900. In particular, the relative radial appearance in 2D image can indicate the relative positioning of the outflow markers 3870 and 3880 when an image plane is aligned to a desired feature at the target site. For example, to avoid blocking the ostia of the left main coronary artery 3910, the commissure post 3826A, containing the first outflow marker 3870, can be aligned with the right/left commissure 3920 of the right coronary cusp 3902 and the left coronary cusp 3904, as illustrated in FIG. 41A. Because the second outflow marker 3880 positioned adjacent to the first outflow marker 3870, the axial strut 3826B will be aligned near the left main coronary artery 3910.

The first outflow marker 3870 and the second outflow marker 3880 can be utilized in combination for circumferential or rotational alignment by setting up an image plane to be approximately parallel to the desired alignment feature and rotating the stent 3802 until the first outflow marker 3870 and the second outflow marker 3880 appear with no radial offset. When aligning the second outflow marker 3880, the image plane can be aligned with a desired feature of the target site. For example, to align the axial strut 3826B, containing the second outflow marker 3880, to the left coronary artery, the imaging device can be positioned to produce an image in the image plane 3932, which is normal to the left/non-coronary commissure 3924. The relative radial appearance in a 2D image from the image plane 3932 can indicate the relative positioning of the first outflow marker 3870 and the second outflow marker 3880 can be utilized to indicate proper alignment. That is, proper alignment can be indicated by both the first outflow marker 3870 and the second outflow marker 3880 appearing on the right side of the image, as illustrated in FIG. 41B.

As illustrated in FIG. 41B, when the axial strut 3826B, containing the second outflow marker 3880, is aligned with the left coronary, the first outflow marker 3870 and the second outflow marker 3880 appear to be in a straight line (e.g., no radial offset) in the 2D image. This is due to the first outflow marker 3870 and the second outflow marker 3880 lying in the image plane 3932 or being perpendicular, along an axial line, to the image plane 3932 relative to the imaging device. As illustrated in FIG. 41C, when the first outflow marker 3870 and the second outflow marker 3880 do not approximately lie in or are perpendicular, along an axial line, to an image plane, e.g., image plane 3930, the first outflow marker 3870 and the second outflow marker 3880 appear radially offset.

Figure 41D:
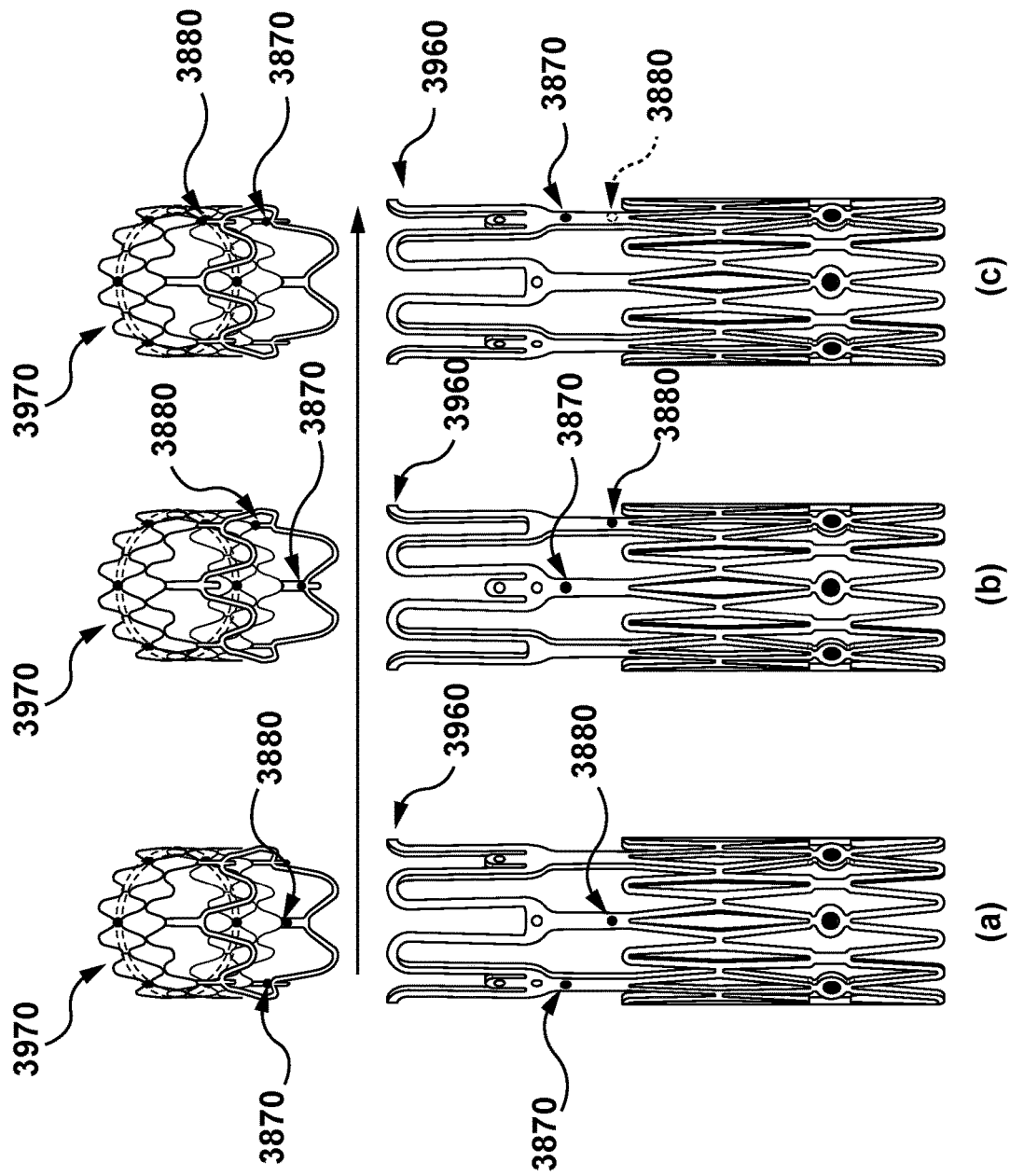

To align the transcatheter valve prosthesis 3900, the stent 3802 can be rotated, in situ, by the delivery system until the first outflow marker 3870 and the second outflow marker 3880 do not appear radially offset, as illustrated in FIG. 41D. FIG. 41D illustrates several sequential images 3960 captured in the image plane 3930, and corresponding images 3970 captured in the annular image plane, as the transcatheter valve prosthesis 3900 is rotated using a handle 3950 of the delivery system. For example, in FIG. 41D, panel (a), the first outflow marker 3870 and the second outflow marker 3880 appear radially offset. To align the transcatheter valve prosthesis 3800, the stent 3802 can rotated, in situ, by the delivery system until the first outflow marker 3870 and the second outflow marker 3880 do not appear radially offset (e.g., in a straight line) as illustrated in FIG. 41D, and panel (c), thereby indicating the first outflow marker 3870 and the second outflow marker 3880 lying in the image plane 3930 or being perpendicular to the image plane 3930 relative to the imaging device.

In embodiments, the first outflow marker 3870 and/or the second outflow marker 3880, alone, can also be used as a guide to the front or rear location of the first outflow marker 3870 appearing in 2D image, as described above. The relative motion of the first outflow marker 3870 and the outflow markers 3880, when rotated, can be used to indicate the front or rear location of the first outflow marker 3870 appearing in 2D image. In particular, the right or left location of the first outflow marker 3870 relative to the outflow markers 3880, during rotation of the stent 3802, can indicate the front or rear location. For example, if the second outflow marker 3880 is placed on an axial strut 3826B to the left of the commissure post 3826A containing the first outflow marker 3870, the appearance of the outflow marker to the left of the first outflow marker 3870, during rotation, would indicate a front location, as shown in FIG. 41D, panel (a). Likewise, the appearance of the outflow marker to the right of the first outflow marker 3870 would indicate a rear location. While the particular movement of the first outflow marker 3870 is discussed above in reference to transcatheter approach, one skilled in the art will realize that the relative movement of the first outflow marker 3870 may change based on a different approach.

In any embodiment described above, the inflow markers 3860, the first outflow marker 3870, and/or the second outflow marker 3880 include radiopaque or other material that allow the inflow markers 3860, the first outflow marker 3870, the second outflow marker 3880 during the installation of the transcatheter valve prosthesis 3800 and 3900 as described above in further detail.

In any embodiment described above, the inflow markers 3860, the first outflow marker 3870, and/or the second outflow marker 3880 can be formed as a directional marker that assists in the circumferential (rotational) orientation based on the shape of the directional marker. For example, the inflow markers 3860, the first outflow marker 3870, and/or the second outflow marker 3880 include formed in and/or can include an element that appears differently based on the rotational orientation, e.g., "C-shaped," "P-shaped," etc. The directional marker can assist a physician with correctly orienting the transcatheter valve prosthesis 3800 and/or 3900, in situ. The directional marker can allow a physician to correctly interpret the circumferential orientation of the transcatheter valve prosthesis 3800 and/or 3900 and to clock or rotate the transcatheter valve prosthesis 3800 and/or 3900 relative to the anatomy to correct the circumferential or rotational orientation if necessary. As discussed above, when being positioned in situ, it is very important to avoid blocking the ostia of the right coronary artery and/or the left main coronary artery and attaining commissure-to-commissure alignment. Proper circumferential or rotational orientation within the native anatomy reduces the risk of blocking coronary access. The transcatheter valve prosthesis 3800 and/or 3900 is rotatable, in situ, by the delivery system to be positioned in a desired orientation. When formed as a direction marker, the inflow markers 3860, the first outflow marker 3870, and/or the second outflow marker 3880 can further assist the physician to determine the orientation of the stent 3802, in situ, and rotate the transcatheter valve prosthesis relative to the anatomy if needed to avoid blocking the coronary arteries and attaining commissure-to-commissure alignment.

For example, the inflow markers 3860, the first marker 3870, and/or the second outflow marker 3880 can be formed as directional marker that includes a C-shaped feature. Because the C-shape of the directional marker looks different when viewed from a front view or position as compared to when viewed from a reverse view or position, the physician can determine whether a particular portion of the stent 3802, a commissure post 3826A, etc., is facing toward or away from the viewing direction. In other words, the C-shape of the directional marker can be an axially non-symmetrical element such that depending upon the location, in situ, the C-shape of the directional marker may be displayed to the physician as a "C" or may be displayed to the physician backwards or as a mirror image of a "C". Since the optimal circumferential or rotational orientation of the transcatheter valve prosthesis 3800 and/or 3900 relative to the coronary arteries can be verified prior to releasing the transcatheter valve prosthesis 3800 and/or 3900 from the delivery system, the physician can ensure that the transcatheter valve prosthesis 3800 and/or 3900 is properly oriented in the native anatomy so as to not block the coronary arteries and commissure-to-commissure alignment. In embodiments, the inflow markers 3860, the first outflow marker 3870, and/or the second outflow marker 3880 can be formed as directional marker that is formed as or includes any letter, number, symbol, or shape that looks different when viewed from a front view or position as compared to when viewed from a reverse view or position, e.g., a letter "P," a letter "S," a number "7," etc.

Figure 42:
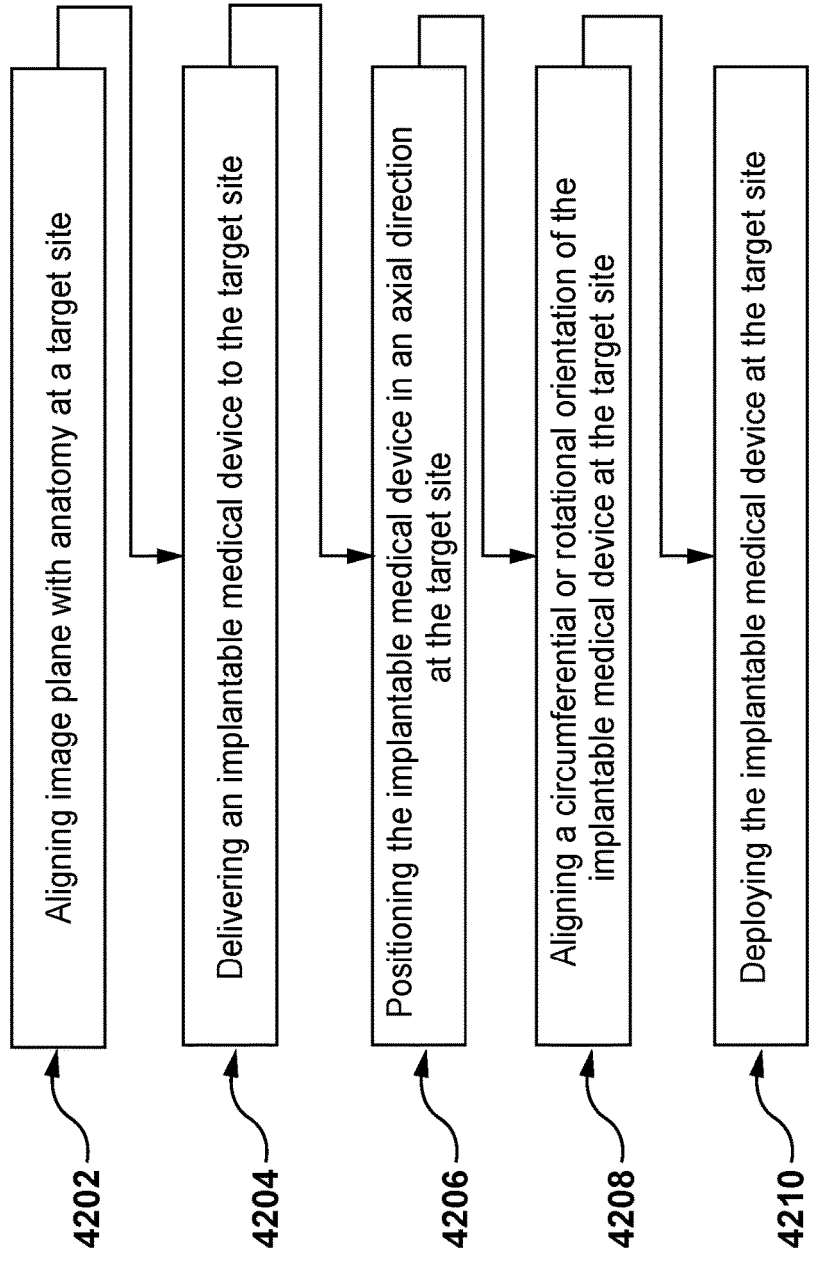
FIG. 42 depicts a flow of a method for delivering the transcatheter valve prosthesis of FIGS. 38A-38E or FIGS. 40A-40C in accordance with an embodiment hereof.

FIG. 42 illustrates a method 4200 of operating of a delivery system utilizing the inflow markers 3860, the first outflow marker 3870, and/or the second outflow marker 3880 in accordance with an embodiment hereof. One skilled in the art will realize that FIG. 42 illustrates one example of steps that can be performed and that existing steps illustrated in FIG. 42 may be removed and/or additional steps may be added to the method 4200.

In step 4202, an image plane of an imaging device is aligned with anatomy at a target site. For example, as discussed above with reference to FIGS. 41A-41D, the imaging device 200, producing images, can be aligned with the anatomy of the patient (e.g., an annulus) to produce images in an image plane 3930 and/or 3932. One skilled in the art will realize that the images in the image plane 3930 and/or 3932 are examples and that the operations and procedures described herein can be performed using 2D image produced in any image plane of the target site and/or using 3D images of the target site.

In step 4204, an implantable medical device is delivered to the target site. In embodiments, the transcatheter valve prosthesis 3800 and/or 3900 can be loaded onto a delivery system (not shown), which is then utilized to deliver the implantable medical device to the target site. Delivery of the transcatheter valve prosthesis 3800 and/or 3900 can be accomplished via any type of procedure utilized to install medical devices in patients. For example, delivery of the transcatheter valve prosthesis 3800 and/or 3900 by the delivery system can be accomplished via a percutaneous transfemoral approach or a transapical approach directly through the apex of the heart via a thoracotomy, or may be positioned within the desired area of the heart via different delivery methods known in the art for accessing heart valves. During delivery, the stent 3802 of the transcatheter valve prosthesis 3800 and/or 3900 remains compressed (in a crimped state) until it reaches a target site, e.g., a diseased native heart valve.

In step 4206, the implantable medical device is positioned in an axial direction at the target site. In embodiments, the inflow markers 3860 of the transcatheter valve prosthesis 3800 and/or 3900 can be utilized to position the stent 3802 in the axial direction relative to native annulus. This may ensure a correct implant depth of the transcatheter valve prosthesis 3800 and/or 3900.

For example, the inflow markers 3860 can be utilized to axially/annularly align the stent 3802 with features in the target site, e.g., edge or terminus 3940 of the right cusp 3902, the left cusp 3904 and the non-coronary cusp 3906. For example, the inflow markers 3860 can be aligned with the edge 3940 of the right cusp 3902, the left cusp 3904 and the non-coronary cusp 3906. To align the transcatheter valve prosthesis 3800 and/or 3900, the stent 3802, the delivery system can be manipulated (e.g., advanced, retracted, etc.) until the inflow markers 3860 align with the edge 3940 of the right coronary cusp 3902, the left coronary cusp 3904 and the non-coronary cusp 3906.

In step 4208, a circumferential or rotational orientation of the implantable medical device is aligned at the target site. In embodiments, the outflow markers 3870 and outflow markers 3880 operate solely or in combination to provide visual references to an orientation of the transcatheter valve prosthesis 3800 and/or 3900 relative to the native structure of the target site of the transcatheter valve prosthesis 3800 and/or 3900 is being installed.

For example, the first outflow marker 3870 or the second outflow marker 3880 can be utilized to align circumferential or rotational orientation of the transcatheter valve prosthesis 3800 and/or 3900. More particularly, the first outflow marker 3870 or the second outflow marker 3880 can allow a physician to correctly interpret the circumferential orientation of the transcatheter valve prosthesis 3800 and to clock or rotate the transcatheter valve prosthesis 3800 and/or 3900 relative to the anatomy to correct the circumferential or rotational orientation, if necessary, to avoid blocking the ostia of the right coronary artery 3908 and/or the left main coronary artery 3910 and attain commissure-to-commissure alignment. To align the transcatheter valve prosthesis 3800 and/or 3900, the stent 3802 can rotated, in situ, by the delivery system to be positioned in a desired circumferential or rotational alignment using the first outflow marker 3870 or the second outflow marker 3880 as a visual reference, as described above.

Likewise, for example, the first outflow marker 3870 and the second outflow marker 3880 can be utilized in combination for circumferential or rotational alignment by rotating the stent 3802 until the first outflow marker 3870 and the second outflow marker 3880 appear with no radial offset. For instance, to align the axial strut 3826B, containing the second outflow marker 3880, to the left coronary, the imaging device can be positioned (in step 4202) to produce an image in the image plane 3932, which is parallel to the annulus 3901 and perpendicular to the left/non-coronary commissure 3924. As illustrated in FIG. 41B (as discussed above), when the axial strut 3826B, containing the second outflow marker 3880, is aligned with the left coronary, the first outflow marker 3870 and the second outflow marker 3880 appear to be in a straight line (e.g., no radial offset) in the 2D image. This is due to the first outflow marker 3870 and the second outflow marker 3880 lying in the image plane 3932 or being perpendicular to the image plane 3932 relative to the imaging device. To align the transcatheter valve prosthesis 3900, the stent 3802 can be rotated, in situ, by the delivery system until the first outflow marker 3870 and the second outflow marker 3880 do not appear radially offset, as illustrated in FIG. 41D (described above).

Additionally, for example, the inflow markers 3860 can be utilized to align the tilt and/or rotation of the stent 3802. For example, to align the transcatheter valve prosthesis 3800 and/or 3900, the stent 3802, the delivery system, can be manipulated (e.g., rotated, tilted, etc.) until the inflow markers 3860 form a predetermined pattern visible in the image captured in the image plane 3930 and/or 3932, for example, as described above with reference to FIGS. 39A-39E.

In step 4210, the implantable medical device is deployed at the target site. In embodiments, the transcatheter valve prosthesis 3800 and/or 3900 can be deployed. In embodiments, the transcatheter valve prosthesis 3800 and/or 3900 can be deployed using an expansion device (e.g., a balloon or mechanical expansion device) of the delivery system. For example, the operator of the delivery system can activate the expansion device (e.g., inflate the balloon or expand the mechanical expansion device) in order to radially expand the stent 3802 in situ. The delivery system is then removed and the transcatheter valve prosthesis 3800 and/or 3900 remains deployed within the native target heart valve.

In some embodiments, if the transcatheter valve prosthesis 3800 and/or 3900 is a replacement heart valve, the transcatheter valve prosthesis 3800 and/or 3900 is configured to block flow in one direction to regulate flow therethrough via valve leaflets that may form a bicuspid or tricuspid replacement valve. When the transcatheter valve prosthesis 3800 and/or 3900 is deployed within the valve annulus of a native heart valve, the stent 3802 of the transcatheter valve prosthesis 3800 and/or 3900 is configured to be radially expanded within native valve leaflets of the defective valve, to thereby retain the native valve leaflets in a permanently open state. In some embodiments, the transcatheter valve prosthesis 3800 and/or 3900 is configured for replacement for an aortic valve such that an inflow end of the transcatheter valve prosthesis 3800 and/or 3900 extends into and anchors within the aortic annulus of a patient's left ventricle, while an outflow end of the transcatheter valve prosthesis 3800 and/or 3900 is positioned within the aortic sinuses.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
   a stent having a crimped configuration for delivery within a vasculature and an expanded configuration for deployment within a native heart valve, the stent including
   an inflow portion formed proximate to an inflow end of the stent, the inflow portion including a plurality of crowns and a plurality of struts with each crown being formed between a pair of opposing struts, a plurality of side openings being defined by the plurality of crowns and the plurality of struts, wherein endmost inflow side openings and endmost inflow crowns are formed at the inflow end of the stent, an outflow portion formed proximate to an outflow end of the stent, the outflow portion including a plurality of crowns and a plurality of struts with each crown being formed between a pair of opposing struts, wherein endmost outflow crowns are formed at the outflow end of the stent, and wherein a total of the endmost inflow crowns are greater than a total of the endmost outflow crowns, a transition portion extending between the inflow portion and the outflow portion, the transition portion including a plurality of axial frame members, wherein at least two axial frame members of the plurality of axial frame members are commissure posts having a first end connected to a single crown at an outflow end of the inflow portion and an unattached second end disposed within the outflow portion such that a pair of struts of the outflow portion intersect each commissure post at a mid-portion thereof, and a prosthetic valve disposed within and secured to at least the transition portion of the stent, the prosthetic valve being configured to substantially block blood flow in one direction to regulate blood flow through a central lumen of the stent.

2. The transcatheter valve prosthesis of claim 1, wherein the prosthetic valve includes three leaflets, and wherein the transition portion includes a total of six axial frame members, with three of the six axial frame members being commissure posts, each axial frame member disposed approximately halfway between a pair of adjacent endmost outflow crowns, and wherein the commissure posts are aligned with and attached to a respective commissure of the three leaflets of the prosthetic valve.

3. The transcatheter valve prosthesis of claim 1, wherein the transition portion includes a total of six axial frame members and a total of six endmost outflow side openings are formed at the outflow end of the stent, each endmost outflow side opening being defined by two struts of the outflow portion, four struts of the inflow portion, and two axial frame members of the transition portion.

4. The transcatheter valve prosthesis of claim 1, wherein the unattached second end of each commissure post does not extend beyond the endmost outflow crowns of the outflow portion.

5. The transcatheter valve prosthesis of claim 1, wherein each commissure post extends substantially parallel to a central longitudinal axis of the stent.

6. The transcatheter valve prosthesis of claim 1, wherein a directional marker is formed on at least one commissure post, the directional marker being an axially non-symmetrical element or opening.

7. The transcatheter valve prosthesis of claim 1, wherein the total of the endmost inflow crowns is twice the total of the endmost outflow crowns.

8. The transcatheter valve prosthesis of claim 1, further comprising:

a plurality of radiopaque inflow markers disposed on the inflow portion of the stent, wherein the radiopaque inflow markers are circumferentially aligned with each other around a circumference of the stent; and a first outflow marker and a second outflow marker, wherein the first outflow marker is disposed on a first commissure post of the commissure posts of the stent and the second outflow marker is positioned on a first axial frame member of the axial frame members of the stent, the first axial frame member being directly adjacent to the first commissure post.

9. The transcatheter valve prosthesis of claim 8, wherein one of the first outflow marker and the second outflow marker is positioned closer to an outflow end of the stent relative to the other of the first outflow marker and the second outflow marker.

10. The transcatheter valve prosthesis of claim 8, wherein only the first commissure post of the commissure posts includes a marker disposed thereon and only the first axial frame member of the axial frame members includes a marker disposed thereon.

11. The transcatheter valve prosthesis of claim 8, wherein the plurality of radiopaque inflow markers comprises six plurality of radiopaque inflow markers positioned at distinct locations around the circumference of the stent.

12. A transcatheter valve prosthesis comprising:

a stent having a crimped configuration for delivery within a vasculature and an expanded configuration for deployment within a native heart valve, the stent including an inflow portion including at least three rows of struts and crowns formed between adjacent pairs of said struts, an outflow portion including a single row of struts and crowns formed between adjacent pair of said struts, and a plurality of axial frame members, wherein the at least three rows of the inflow portion are formed between an inflow end of the axial frame members and an inflow end of the stent, and wherein the outflow portion is coupled to an outflow end of the axial frame members, wherein exactly two struts of the plurality of struts of the outflow portion are disposed between adjacent axial frame members, at least two axial frame members of the plurality of axial frame members being commissure posts having a first end connected to a single crown at an outflow end of the inflow portion and an unattached second end disposed within the outflow portion such that a pair of struts of the outflow portion intersect each commissure post at a mid-portion thereof, wherein a directional marker is formed on at least one commissure post, the directional marker being an axially non-symmetrical element or opening.

13. The transcatheter valve prosthesis of claim 12, wherein the plurality of axial frame members includes exactly six axial frame members, wherein three of the six axial frame members are commissure posts and three of the six axial frame members are axial struts, and wherein each of the axial struts is disposed between adjacent commissure posts.

14. The transcatheter valve prosthesis of claim 13, wherein one of the at least three rows of struts and crowns of the inflow portion includes crowns coupled to inflow end of the axial frame member, wherein the one row includes at least four struts between adjacent axial frame members.

15. The transcatheter valve prosthesis of claim 12, wherein the plurality of axial frame members includes a plurality of axial struts and a plurality of commissure posts, wherein there are the same number of axial struts and commissure posts, wherein each of the axial struts is disposed between adjacent commissure posts.

16. The transcatheter valve prosthesis of claim 12, wherein the unattached second end of each commissure post does not extend beyond endmost outflow crowns of the outflow portion.

17. A transcatheter valve prosthesis comprising:
a stent having a crimped configuration for delivery within a vasculature and an expanded configuration for deployment within a native heart valve, the stent including
an inflow portion including at least three rows of struts and crowns formed between adjacent pairs of said struts,
an outflow portion including a single row of struts and crowns formed between adjacent pair of said struts, and
a plurality of axial frame members, wherein the at least three rows of the inflow portion are formed between an inflow end of the axial frame members and an inflow end of the stent, and wherein the outflow portion is coupled to an outflow end of the axial frame members, at least two axial frame members of the plurality of axial frame members being commissure posts having a first end connected to a single crown at an outflow end of the inflow portion and an unattached second end disposed within the outflow portion such that a pair of struts of the outflow portion intersect each commissure post at a mid-portion thereof, wherein each commissure post is a planar bar that is substantially straight between the first end and the unattached second end thereof and each commissure post extends substantially parallel to a central longitudinal axis of the stent, and
a prosthetic valve disposed within and secured to the stent, the prosthetic valve being configured to substantially block blood flow in one direction to regulate blood flow through a central lumen of the stent, wherein each commissure post is aligned with and attached to a commissure of the prosthetic valve.

18. The transcatheter valve prosthesis of claim 17, wherein the plurality of axial frame members includes a total of six axial frame members, with three of the six axial frame members being commissure posts, each axial frame member disposed approximately halfway between a pair of adjacent endmost outflow crowns.

19. The transcatheter valve prosthesis of claim 17, wherein the plurality of axial frame members includes a total of six axial frame members and a total of six endmost outflow side openings are formed at the outflow end of the stent, each endmost outflow side opening being defined by two struts of the outflow portion, four struts of the inflow portion, and two axial frame members.

20. The transcatheter valve prosthesis of claim 17, wherein endmost outflow crowns are formed at the outflow end of the stent and wherein the unattached second end of each commissure post does not extend beyond the endmost outflow crowns of the outflow portion.

21. The transcatheter valve prosthesis of claim 17, wherein a directional marker is formed on at least one commissure post, the directional marker being an axially non-symmetrical element or opening.

22. The transcatheter valve prosthesis of claim 17, wherein endmost outflow crowns are formed at the outflow end of the stent, endmost inflow crowns are formed at the inflow end of the stent, and a total of the endmost inflow crowns is twice a total of the endmost outflow crowns.

23. The transcatheter valve prosthesis of claim 17, wherein each commissure post has a consistent width along a length thereof between the first end and the unattached second end thereof.

24. The transcatheter valve prosthesis of claim 17, wherein each commissure post has an opening formed therein at the mid-portion thereof where the pair of struts of the outflow portion intersect the commissure post.

* * * * *